United States Patent
Ben et al.

(10) Patent No.: US 12,060,573 B2
(45) Date of Patent: *Aug. 13, 2024

(54) STABILIZED AMORPHOUS CALCIUM CARBONATE AS A SUPPLEMENT FOR CELL CULTURE MEDIA

(71) Applicant: AMORPHICAL LTD., Ness Ziona (IL)

(72) Inventors: Yosef Ben, Arava (IL); Abraham Shahar, Rehovot (IL); Amir Arav, Tel Aviv (IL)

(73) Assignee: AMORPHICAL LTD., Ness Ziona (IL)

(*) Notice: Subject to any disclaimer, the term of this patent is extended or adjusted under 35 U.S.C. 154(b) by 411 days.

This patent is subject to a terminal disclaimer.

(21) Appl. No.: 16/069,774

(22) PCT Filed: Jan. 17, 2017

(86) PCT No.: PCT/IL2017/050058
§ 371 (c)(1),
(2) Date: Jul. 12, 2018

(87) PCT Pub. No.: WO2017/125917
PCT Pub. Date: Jul. 27, 2017

(65) Prior Publication Data
US 2019/0048313 A1  Feb. 14, 2019

Related U.S. Application Data

(60) Provisional application No. 62/279,843, filed on Jan. 18, 2016, provisional application No. 62/279,844, filed on Jan. 18, 2016, provisional application No. 62/279,845, filed on Jan. 18, 2016, provisional application No. 62/376,428, filed on Aug. 18, 2016, provisional application No. 62/434,453, filed on Dec. 15, 2016.

(51) Int. Cl.
*C12N 5/00* (2006.01)
*C12N 5/073* (2010.01)
*C12N 5/075* (2010.01)
*C12N 5/076* (2010.01)
*C12N 5/077* (2010.01)
*C12N 5/0775* (2010.01)
*C12N 5/0793* (2010.01)

(52) U.S. Cl.
CPC ......... *C12N 5/0018* (2013.01); *C12N 5/0604* (2013.01); *C12N 5/0609* (2013.01); *C12N 5/061* (2013.01); *C12N 5/0619* (2013.01); *C12N 5/0658* (2013.01); *C12N 5/0663* (2013.01); *C12N 2500/14* (2013.01)

(58) Field of Classification Search
CPC .... C12N 5/0018; C12N 5/061; C12N 5/0609; C12N 2500/14
See application file for complete search history.

(56) References Cited

U.S. PATENT DOCUMENTS

| | | | |
|---|---|---|---|
| 4,757,017 A | 7/1988 | Cheung | |
| 5,460,803 A | 10/1995 | Tung | |
| 5,562,895 A | 10/1996 | Tung | |
| 7,666,673 B2 * | 2/2010 | Shinohara | C12N 5/061 435/373 |

FOREIGN PATENT DOCUMENTS

| | | |
|---|---|---|
| CN | 102604895 A | 7/2012 |
| EP | 0628017 A1 | 12/1994 |
| RU | 94022264 A | 5/1996 |
| WO | 2005026324 A2 | 3/2005 |
| WO | 2005/115414 A2 | 12/2005 |
| WO | 2008/041236 A2 | 4/2008 |
| WO | 2009/053967 A1 | 4/2009 |
| WO | 2013/088440 A1 | 6/2013 |
| WO | 2014/024191 A1 | 2/2014 |
| WO | 2014/122658 A1 | 8/2014 |
| WO | 2016/016893 A1 | 2/2016 |
| WO | 2016/016895 A1 | 2/2016 |
| WO | 2016/193982 A1 | 12/2016 |
| WO | 2016/193983 A1 | 12/2016 |
| WO | 2017/125918 A1 | 7/2017 |

OTHER PUBLICATIONS

Marín-Briggiler et al. Calcium requirements for human sperm function in vitro, 2003, Fertility and Sterility 79(6): 1396-1403 (Year: 2003).*
Qi et al ("ATP-Stabilized Amorphous Calcium Carbonate Nanospheres and Their Application in Protein Adsorption,." Small 2014, 10, No. 10, 2047-2056) (Year: 2014).*
Popper et al ("Calcium mobilization and cell proliferation activated by extracellular ATP in human ovarian tumour cells," Cell Calcium 14(3): 209-218, 1993). (Year: 1993).*
Johnson et al ("Maintenance of Motility in Mouse Sperm Permeabilized with Streptolysin O," Biology of Reproduction 60, 683-690 (1999)) (Year: 1999).*
Brusentsev et al., (2014) Traditional and Modern Approaches to Culture of Preimplantation Mammalian Embryos In Vitro. Russian Journal of Developmental Biology 45(2): 73-88; English abstract on p. 88.
Agarwal and Sekhon (2010) The role of antioxidant therapy in the treatment of male infertility. Hum Fertil (Camb) 13(4): 217-225.

(Continued)

*Primary Examiner* — Allison M Fox
*Assistant Examiner* — Jennifer S Spence
(74) *Attorney, Agent, or Firm* — Dorsey & Whitney LLP

(57) ABSTRACT

Stabilized amorphous calcium carbonate (ACC) as a supplement of cell culture media and the cell culture medium supplements comprising stabilized ACC are provided. In particular the stabilized ACC is useful for enhancing the growth of cell and tissue cultures, gametes and embryos in vitro.

19 Claims, 9 Drawing Sheets

(56) References Cited

OTHER PUBLICATIONS

Amann and Waberski (2014) Computer-assisted sperm analysis (CASA): capabilities and potential developments. Theriogenology 81(1): 5-17.

Bentov et al., (2010) Stabilization of amorphous calcium carbonate by phosphate rich organic matrix proteins and by single phosphoamino acids. J Struct Biol 171(2): 207-215.

Bhoumik et al., (2014) Optimum calcium concentration: a crucial factor in regulating sperm motility in vitro. Cell Biochem Biophys 70(2): 1177-1183.

Bursac et al., (2015) Synergizing Engineering and Biology to Treat and Model Skeletal Muscle Injury and Disease. Annu Rev Biomed Eng 17: 217-242.

Culligan and Ohlendieck (2002) Abnormal Calcium Handling in Muscular Dystrophy. Basic Appl Myol 12(4): 147-157.

Datta et al., (2015) Add-ons in IVF programme—Hype or Hope? Facts Views Vis Obgyn 7(4): 241-250.

Joyce et al., (2012) Bone health and associated metabolic complications in neuromuscular diseases. Phys Med Rehabil Clin N Am 23(4): 773-799.

Kevenaar and Hoogenraad (2015) The axonal cytoskeleton: from organization to function. Front Mol Neurosci 8: 44; 12 pages.

Kumar and Singh (2015) Trends of male factor infertility, an important cause of infertility: A review of literature. J Hum Reprod Sci 8(4): 191-196.

Meiron et al., (2011) Solubility and bioavailability of stabilized amorphous calcium carbonate. J Bone Miner Res 26(2): 364-372.

Nasiri and Eftekhari-Yazdi (2015) An overview of the available methods for morphological scoring of pre-implantation embryos in in vitro fertilization. Cell J 16(4): 392-405.

Rahman et al., (2014) Calcium influx and male fertility in the context of the sperm proteome: an update. Biomed Res Int 2014: 841615; 13 pages.

Shaltiel et al., (2013) Bone loss prevention in ovariectomized rats using stable amorphous calcium carbonate. Health 5 (7A2): 18-29.

Shechter et al., (2008) A gastrolith protein serving a dual role in the formation of an amorphous mineral containing extracellular matrix. Proc Natl Acad Sci U S A 105(20): 7129-7134.

Shin et al., (2013) Wasting mechanisms in muscular dystrophy. Int J Biochem Cell Biol 45(10): 2266-2279.

Tolba et al., (2016) High biocompatibility and improved osteogenic potential of amorphous calcium carbonate/vaterite. J Mater Chem B 4: 376-386.

Vaisman et al., (2014) Increased calcium absorption from synthetic stable amorphous calcium carbonate: double-blind randomized crossover clinical trial in postmenopausal women. J Bone Miner Res 29(10): 2203-2209.

DMD_M.2.1.005 (SOP (ID) Number): "The use of four limb hanging tests to monitor muscle strength and condition over time"; George Carlson (Author), Maaike van Putten (Official reviewer). Issued: Aug. 3, 2011 and Last reviewed: Jun. 29, 2016; 11 pages.

"Testing the Effect of Crustacean's Gastrolith Nutraceutical on Mineralization Rate During Distraction Osteogenesis"; Amorfical (Collaborator), Ron Lamdan, Hadassah Medical Organization (Responsible Party). Study NCT01087437, last updated Mar. 30, 2014 (v6). Retrieved from https://clinicaltrials.gov/ct2/history/NCT01087437?V_6=View#StudyPageTop on Jan. 24, 2019; 4 pages.

Wagner et al., (2007) Current treatment of adult Duchenne muscular dystrophy. Biochim Biophys Acta 1772(2): 229-237.

Caglar Aytac et al., (2015) Can calcium ionophore "use" in patients with diminished ovarian reserve increase fertilization and pregnancy rates? A randomized, controlled study. Fertil Steril 104(5): 1168-1174.

Eftekhar et al., (2013) Effect of oocyte activation with calcium ionophore on ICSI outcomes in teratospermia: A randomized clinical trial. Iran J Reprod Med 11(11): 875-882.

Sfontouris et al., (2015) Artificial oocyte activation to improve reproductive outcomes in women with previous fertilization failure: a systematic review and meta-analysis of RCTs. Hum Reprod 30(8): 1831-1841.

"Animal Reproduction Biotechnology", Sang Yun Zi editor. China Agriculture Press, Jul. 31, 2006. pp. 343-344.

Calcium in Cell Culture; Importance and uses of calcium in serum-free eucaryotic, including hybridoma and Chinese Hamster Ovary (CHO) cell cultures. Sigma-Aldrich. Retrieved from: https://web.archive.org/web/20150524020552/ https://www.sigmaaldrich.com/life-science/cell-culture/learning-center/media-expert/calcium.html May 24, 2015. 2 pages.

Ackerman et al., (1985) Toxicity testing for human in vitro fertilization programs. J In Vitro Fert Embryo Transf 2(3): 132-137.

Fleetham et al., (1993) The mouse embryo culture system: improving the sensitivity for use as a quality control assay for human in vitro fertilization. Fertil Steril 59(1): 192-196.

Flinck et al., (2018) Roles of pH in control of cell proliferation. Acta Physiol (Oxf) 223(3): e13068; 17 pages.

Glacken et al., (1986) Reduction of waste product excretion via nutrient control: Possible strategies for maximizing product and cell yields on serum in cultures of mammalian cells. Biotechnol Bioeng 28(9): 1376-1389.

Hentemann et al., (2011) Differential pH in embryo culture. Fertil Steril 95(4): 1291-1294.

Michl et al., (2019) Evidence-based guidelines for controlling pH in mammalian live-cell culture systems. Commun Biol 2: 144; 12 pages.

Naciri et al., (2008) Monitoring pH and dissolved oxygen in mammalian cell culture using optical sensors. Cytotechnology 57(3): 245-250.

Pradhan et al., (2012) In situ pH maintenance for mammalian cell cultures in shake flasks and tissue culture flasks. Biotechnol Prog 28(6): 1605-1610.

Rossi et al., (2019) Calcium, mitochondria and cell metabolism: A functional triangle in bioenergetics. Biochim Biophys Acta Mol Cell Res 1866(7): 1068-1078.

Van der Valk et al., (2010) Optimization of chemically defined cell culture media-replacing fetal bovine serum in mammalian in vitro methods. Toxicol In Vitro 24(4): 1053-1063.

Durand-Smet et al., (2014) A comparative mechanical analysis of plant and animal cells reveals convergence across kingdoms. Biophys J 107(10): 2237-2244. With correction.

Homa et al., (1993) The role of calcium in mammalian oocyte maturation and egg activation. Hum Reprod 8(8): 1274-1281.

Tester et al., (2013) Time-Resolved Evolution of Short- and Long-Range Order During the Transformation of Amorphous Calcium Carbonate to Calcite in the Sea Urchin Embryo. Advanced Functional Materials 23(34): 4185-4194.

\* cited by examiner

FIG. 8
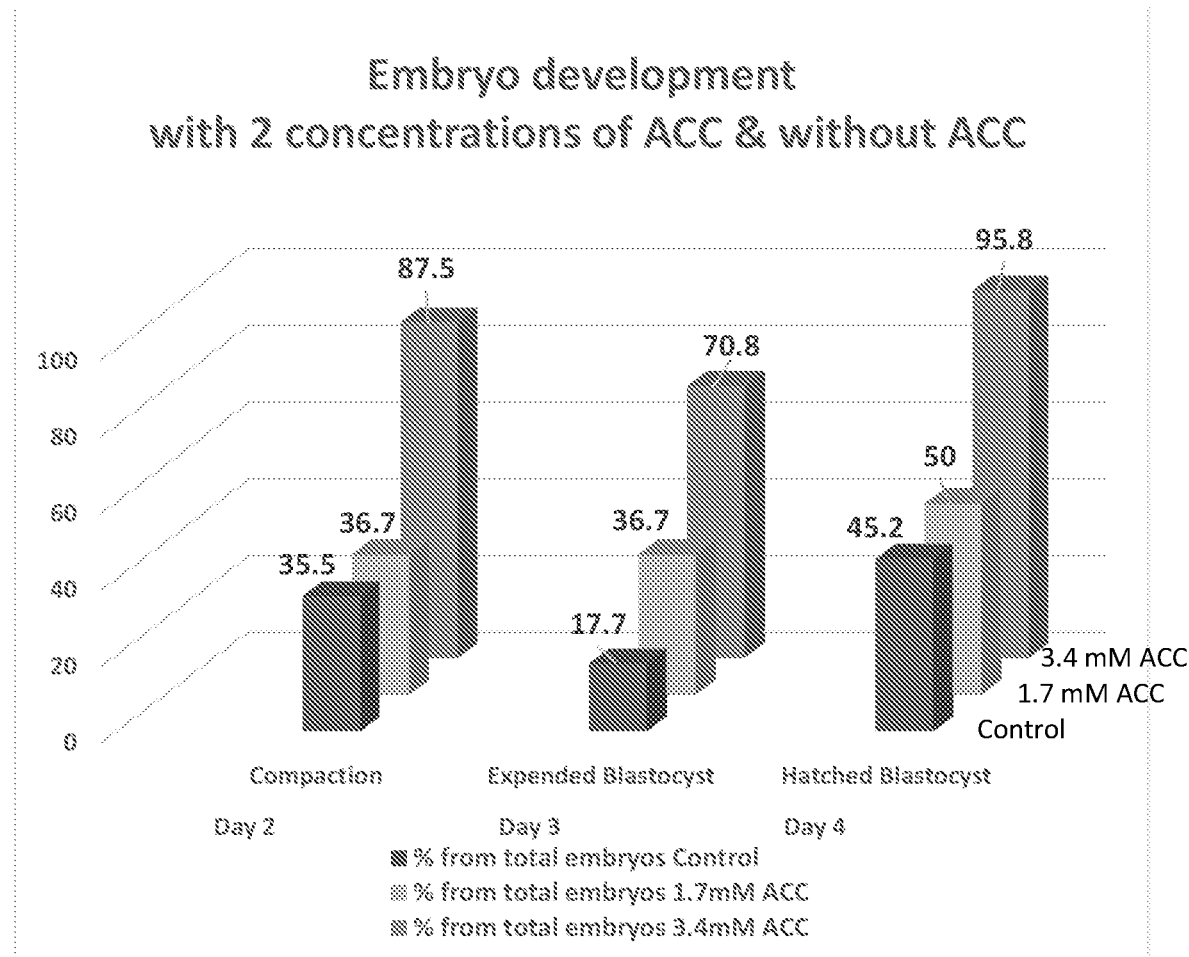
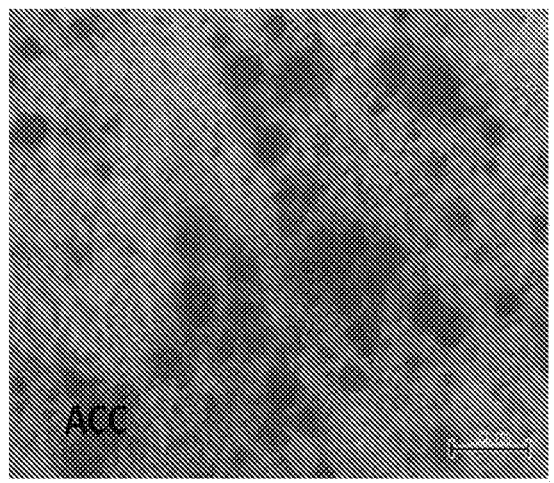
FIG. 9 A
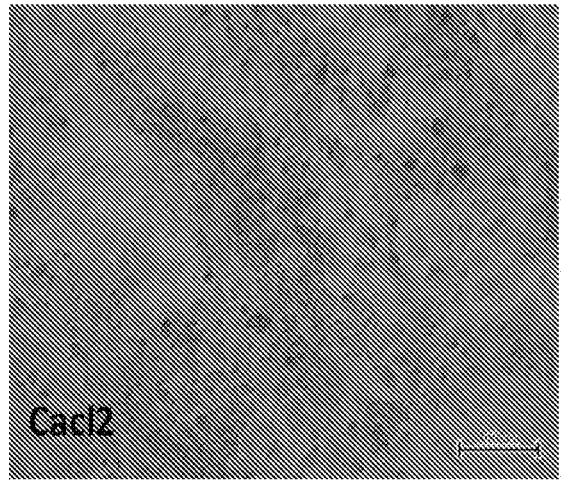
FIG. 9B

STABILIZED AMORPHOUS CALCIUM CARBONATE AS A SUPPLEMENT FOR CELL CULTURE MEDIA

FIELD OF THE INVENTION

The present invention provides stabilized amorphous calcium carbonate as a supplement of cell culture media. In particular the ACC is useful for enhancing the growth of cell and tissue cultures in vitro. In additional aspects of the invention, cell culture media supplement comprising stabilized ACC are provided.

BACKGROUND OF THE INVENTION

Cell culture techniques allow growing in vitro animal, plant or insect cells removed from tissues, when supplying the appropriate nutrients and conditions. Cell culture techniques have a number of applications including investigation of cellular processes, assessing the effect of various chemical compounds or drugs on specific cell types, synthesizing valuable biologics in the industrial scale and generation of expanded cells for transplantation purposes. Cell culture techniques are used for in vitro fertilization, stem cell research and vaccine production.

One of the most important uses of cell culture techniques is mass production of biologics including specific proteins such as monoclonal antibodies. The number of such commercially valuable biologics has increased rapidly over the last decades and has led to the present widespread interest in mammalian cell culture technology.

The composition of media used to culture cells is of a great importance because of its influence on cell survival, proliferation and production of the biologics of interest. Many different cell culture media, having different levels of specificity to cell cultures, were developed. While some of the media are basal media that may be supplemented according to the requirements of different cell cultures, other are more complex media. Hundreds of individual compounds can be added to cell culture media so as to obtain the desired effect. But the concept of media supplementation is usually limited to addition of materials that generally promote establishment and maintenance of a cell culture. Among most used supplements are minerals, vitamins, amino acids, hormones and serum, most often fetal bovine serum, horse serum or human serum. However, since the use of serum may be undesirable in many case, growth media with reduced content of serum or serum-free media are used.

There is an ongoing research and development of media and in particular supplements to media allowing supporting and proliferation of cell and tissue cultures, particularly providing beneficial large-scale manufacturing culture conditions.

SUMMARY OF THE INVENTION

It has been surprisingly found that cell culture media supplemented with stabilized amorphous calcium carbonate (ACC) provide enhanced growth of various cells, in comparison to cells grown in media supplemented with other sources of calcium. In particular it has been observed that stabilized ACC enhanced myotubes formation in mdx cells, being a model of Duchenne muscular dystrophy. In addition, an enhanced in-vitro development of embryos was observed in the media comprising stabilized ACC, either a monoculture medium of "one step" or to the "sequential" (Cleavage medium). It has been surprisingly found that embryos, that were grown in cleavage medium supplemented with stabilized ACC showed a rapid cleavage and higher hatching rate. In other cases, neural cells grown in the media supplemented with ACC showed an enhance neural filaments regeneration, and stem cells grown in ACC supplemented media demonstrated faster expansion and differentiation. It was further surprisingly found, that sperm, incubated in the presence of ACC, demonstrated much higher motility following swim-up procedure, and the concentration of sperm cell incubated with ACC in the upper phase (the motile sperm) was up to 7 times higher than the concentration in the untreated sample. Moreover, it has been shown that ACC did not have the bi-phasic effect on sperm motility which has been observed upon addition of $Ca^{2+}$ ions to sperm samples. All these observation indicate that stabilized ACC being a supplement to a cell culture media enhance and promotes cells growth and provides better functionality.

In one aspect the present invention provides a cell culture medium, wherein the cell culture medium is supplemented with amorphous calcium carbonate (ACC) stabilized by at least one stabilizing agent and wherein said cell culture medium is suitable for growth of a biological culture. According to some embodiments, the medium is suitable for growing culture of cells, tissue culture, organ culture or organs. According to other embodiments, the cell culture medium supplemented with stabilized ACC is capable of enhancing or promoting the growth, e.g. enhancing the proliferation, maturation, propagation, regeneration, development, preservation such as cryopreservation and/or differentiation of cells, tissues and organs. According to one embodiment, the cells are animal, plant or insect cells. According to one embodiment, the cell culture medium supplemented with stabilized ACC is suitable for growth and optionally capable of enhancing the growth of cell culture, tissue culture, organ culture, wherein said cultures are animal, plant or incest cell, tissue or organ culture. According to one embodiment, the cell culture medium supplemented with stabilized ACC is suitable for growth of stem cell such as embryonic, chorionic, amniotic, hematopoietic, mesenchymal, neural, glial, Nasal Olfactory Mucosa (NOM), adult tissue specific and induced pluripotent stem cells or for growth of embryos, such as human or non-human mammal embryos. In other embodiments, such cell culture medium is capable of enhancing stem cells proliferation, expansion and/or differentiation, capable of enhancing gametes maturation or capable of enhancing development of embryos. According to some embodiments, the cell culture medium supplemented with stabilized ACC is suitable for growth and optionally capable of enhancing the growth of yeast or bacteria. In some embodiments, the bacteria is *E. coli* or probiotic bacteria such bacteria of *Bifidobacterium* and *Lactobacillus* genera. According to any one of the above embodiments, the cell culture medium of the present invention may be any medium suitable for growth of cells, e.g. natural medium comprising biological fluid or artificial medium such as balanced salt solution, basal medium or complex medium. The cell culture medium of the present invention may be further supplemented as known in art. According to the present invention, the cell culture medium is supplemented with ACC stabilized by at least one stabilizing agent. The stabilizing agent may be any agent known in art. In particular embodiments, the stabilizer is selected from a polyphosphate, such as inorganic polyphosphate, phosphorylated amino acid, bisphosphonate, organic acid and any combination thereof. According to some embodiments, the stabilizing agent is a combination of said stabilizers, e.g. combination of inorganic polyphosphate with organic acid such as citric acid or a combination of a phosphorylated amino acid with an organic acid.

According to another aspect the present invention provides amorphous calcium carbonate (ACC) stabilized by at least one stabilizing agent, for use as a supplement to a cell culture medium. According to one embodiment, the stabilized ACC is added to the medium during the preparation of the medium. According to another embodiment, the ACC is added to the medium before use.

According to yet another aspect, the present invention provides a cell culture medium supplement comprising amorphous calcium carbonate (ACC) stabilized by at least one stabilizing agent. According to one embodiment, the cell culture medium supplement comprising ACC stabilized the stabilized ACC is added to the medium during the preparation of the medium. According to another embodiment, the supplement is added to the medium prior use. The cell culture medium supplement may be a solid, liquid or semi-liquid supplement. According to any one of the above embodiments, the ACC is stabilized by at least one stabilizing agent. Such cell culture medium supplement is capable of enhancing growth e.g. enhancing the proliferation, maturation, propagation, regeneration, development and/or differentiation of cells, tissues and organs.

According to a further aspect, the present invention provides amorphous calcium carbonate (ACC) stabilized by at least one stabilizer and formulated as a supplement for cell culture medium, wherein said ACC is stabilized by at least one stabilizing agent.

According to another aspect, the present invention provides a method for enhancing cell growth of a biological culture, comprising exposing the biological culture to ACC stabilized by at least one stabilizer. According to some embodiments, the biological culture is selected from a culture of cells, cell culture, tissue culture, organ culture and bacterial culture. In one embodiment, the method comprises enhancing cell growth and in particular enhancing formation of myotubes, enhancing embryo development, enhancing nerve cells regeneration and enhancing maturation and/or preservation of gametes.

According to one aspect, the present invention provides a kit comprising ACC for use as a supplement for cell culture medium of the present invention, or a cell culture medium supplement comprising stabilized ACC, and instructions for use of said ACC or said supplement in combination with cell culture medium. According to certain aspects, the present invention provides a kit comprising amorphous calcium carbonate (ACC) stabilized by at least one stabilizer and instructions for use of said ACC in combination with cell culture medium. According to one embodiment, the ACC is for use as a cell culture medium supplement. According some embodiments, the kit comprises cell culture medium supplement comprising ACC stabilized by at least one stabilizer and instruction for use of said ACC in combination with cell culture medium. The kit of the present invention may further comprise any know medium suitable for growth of cells, tissues or organs.

BRIEF DESCRIPTION OF THE FIGURES

FIG. 8 shows the effect of stabilized ACC on mice embryos development in vitro.

DETAILED DESCRIPTION OF THE INVENTION

Figure 1:
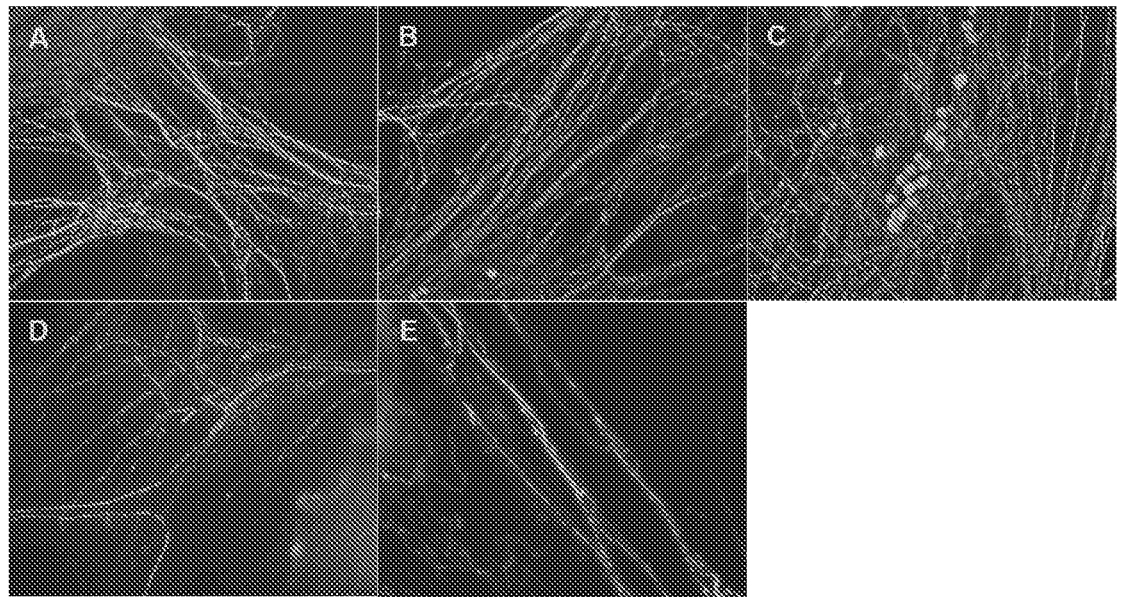
FIG. 1 shows the effect of different calcium sources on neuronal sprouting from cultured spinal cord-dorsal root ganglia (SC-DRG) slices. Immunofluorescent staining (anti neurofilament antibody) of nerve fibers grown from SC-DRG slices exposed to the following calcium compounds ($Ca^{2+}$ concentration of 2 mM): (A) ACC-Etidronic Acid; (B) ACC-phosphoserine; (C) gastrolith; (D) crystalline calcium carbonate (CCC); and (E) $CaCl_2$) solution (control). Original magnification ×100.

It has been surprisingly found that addition of ACC to cell culture medium enhances growth of various types of cell. According to one aspect, the present invention provides a cell culture medium supplemented with amorphous calcium carbonate (ACC), wherein said ACC is stabilized by at least one stabilizing agent. According to other aspects, the present invention provides stabilized ACC for use as a supplement to a cell culture medium. In certain aspects, the present invention provides a cell culture supplement comprising stabilized ACC.

For each aspect of the present invention individually and collectively the following terminology is used and the specific parameters are as defined hereinbelow:

The term "cell culture medium", "growth medium" and "culture medium" are used herein interchangeably and refer to a medium used for, suitable for or capable of supporting the growth of a biological culture such as cells, tissues or organs and providing said cells, tissue or organ with a proper environment. Different cell culture media may have different properties and comprise different components, however almost all media are isotonic media and have an osmotic pressure suitable for cell growth. Thus, the cell culture medium is an isotonic cell culture medium. The term "isotonic" as used herein refers a cell culture medium having the osmolality of an aqueous solution at 37° C. is in the range of 270-300 mOsmol/kg. Thus, in one embodiment, water or more particular de-ionized water per se is not considered as a cell culture medium. According to some embodiments, the tissue culture comprises sodium chloride, potassium chloride and a source of phosphorous such as sodium phosphate mono or di basic. According to some embodiments, the medium is suitable for growing cell culture, tissue culture, organ culture or organs. The cells may be eukaryotic or prokaryotic. In particular the cell culture medium refers to a medium suitable for growth eukaryotic culture of cell, tissue culture or organ culture. In some particular embodiments, the medium may be a complete medium, a basal medium, a basal medium supplemented with cell culture medium supplement, medium with various amounts of serum or chemically defined medium.

The term "supplemented" as used herein refers to a medium to which the ACC stabilized with at least one stabilizer is added, thus the medium comprises ACC stabilized with at least one stabilizer. The term encompasses medium prepared with ACC and medium to which the ACC is added before use.

Thus in one embodiment, the present invention provides a cell culture medium, wherein the cell culture medium is supplemented with amorphous calcium carbonate (ACC) stabilized by at least one stabilizing agent and wherein said cell culture medium is suitable for growth of a biological culture.

The terms "culture", "biological culture" and "culture of cells" are used herein interchangeably and refer to cells, tissues, organs culture or organ grown in vitro in a pre-defined conditions. In some embodiments, the biological culture is selected from a animal, plant or insect cell culture; animal, plant or insect tissue culture, animal, plant or insect organ culture, yeast culture and bacterial culture.

The term "cell culture" as used herein refers to cells of a multicellular eukaryote which are maintained, cultivated or grown in an artificial in vitro environment. The cell culture may be a suspension culture, in which the cells are cultured in a liquid medium by constant agitation or on micro carriers, or an adherent or monolayer culture.

The term "tissues culture" as used herein refers to a tissue maintained or grown in vitro.

The term "organ culture" as used herein refers to part(s) of an organ or a whole organ cultured in vitro.

The term "stem cells" refers to cells which have the capacity to proliferate and differentiate into different cell types.

The term "amorphous calcium carbonate" and "ACC" are used herein interchangeably and refer to non-crystalline form of calcium carbonate stabilized by at least one stabilizing agent. ACC may be obtained from a natural source or chemically synthesized. The terms also include naturally stabilized ACC such as ACC obtained from gastrolith.

The term "natural ACC" as used herein refers to any ACC isolated or derived from a natural source. Non-limiting examples of natural sources of ACC include gastroliths of freshwater crustaceans.

The term "synthetic ACC" as used herein refers to any ACC produced and/or derived by man ex-vivo.

According to some embodiments, the cell culture medium according to the present invention is suitable for growth of a biological culture. According to one embodiment, the biological culture is a culture of eukaryote or prokaryote cells. The term "growth" as used herein encompass any of the following: proliferation, maturation, propagation, regeneration, support, differentiation, development, preservation, cryopreservation and any combination thereof and may be used differently in accordance to the type of cells. According to one embodiment, the cell culture medium is suitable for supporting, for proliferation or propagation of cells. In one exemplary embodiment, the cell culture medium is suitable for proliferation or propagation of eukaryotic cells, e.g. unicellular organisms or cells of a multicellular organism. According to another exemplary embodiment, the cell culture medium is suitable for proliferation or propagation of prokaryotic cells. According to other embodiments, the cell culture medium is suitable for maturation and/or development of cells, e.g. development of embryos or maturation of gamete cells. The term "embryo" as used herein refers to a fertilized mammalian oocyte, i.e. a zygote, and to a multi-cellular organism developing from said zygote at its earliest stages of the development. The terms "gamete" or "gamete cells" are used herein interchangeably and refers to any male or female germ cell that is capable of initiating formation of a new diploid individual. Examples of gametes are sperm and oocytes. The term "sperm" and "spermatozoa" as used herein interchangeably refers to male reproductive cells. The term "sperm sample" refers to one or more samples comprising sperm. The sperm sample may be semen obtained from a subject or processed semen, liquefied semen, sedimented and optionally resuspended sperm, etc. According to some embodiments, the cell culture medium is suitable for regeneration of cells, e.g. regeneration of nerve cells. The terms "neuronal regeneration" and "nerve regeneration" as used herein may be used interchangeably and refer to recovery of functions of a damaged nerve. Specifically, it includes recovery of signaling via the nerve by repairing a damaged site, regrowth of axonal and dendritic neuronal fibers, of the peripheral or the central nervous system. In some embodiments, nerve regeneration refers to sprouting from damaged neuronal fibers. In some embodiments, nerve regeneration refers to sprouting from damaged neuronal fibers. Therefore, the cell culture medium according to the present invention is capable of promoting profound nerve fiber regeneration. According to another embodiment, the cell culture medium is suitable for differentiation of cells, e.g. differentiation of stem cells and in particular differentiation of stem cells to osteoblasts. According to some embodiments, the cell culture medium is suitable for supporting a proliferation of a tissue culture and organ culture. According to some embodiments, the cell culture medium is suitable for in vitro preservation of an organ.

According to some embodiments, the cell culture medium supplemented with stabilized ACC according to the present invention is capable of enhancing the growth as defined herein above of a biological culture. The term "enhancing" as used herein refers to promoting, improving, augmenting, ameliorating, typically increasing the growth parameters. According to some embodiments, of the present invention, the terms "capable of enhancing" and "enhances" are used interchangeably. The enhancement may be measured relatively to a control sample grown in identical conditions but without the ACC. Thus in one embodiment, the cell culture medium supplemented with stabilized ACC according to the present invention is capable of enhancing proliferation, maturation, propagation, regeneration, development, cryopreservation and/or differentiation of cells, tissues or organs. According to one embodiment, the cell culture medium is capable of enhancing differentiation of stem cells. According to another embodiment, the cell culture medium supplemented with stabilized ACC is capable of enhancing proliferation of cells. According to yet another embodiment, the cell culture medium supplemented with stabilized ACC is capable of enhancing maturation of cells. According to a further embodiment, the cell culture medium supplemented with stabilized ACC is capable of enhancing development of cells or tissues. According to certain embodiments, the cell culture medium supplemented with stabilized ACC is capable of enhancing regeneration of cell. The enhancement of proliferation, maturation, propagation, regeneration, development and/or differentiation of cells, tissues or organs may be measured as percent of enhancement in comparison to the control as defined hereinabove. Therefore, according to one embodiment, the cell culture medium supplemented with stabilized ACC is capable of enhancing the growth parameters by about 10% to about 600%, about 20% to about 500%, about 30% to about 400%, about 40% to about 300%, about 50% to about 200, about 60% to about 150% or about 70% to about 100%. Enhancement by 100% meaning that the parameter, e.g. proliferation in increased 2 times; enhancement by 200% means that the parameter, e.g. embryo development, in increased 3 times, and so on. According to some embodiments, the growth parameters are enhanced by about 100% to about 500%, about 120% to about 400%, about 150% to about 300%.

According to some embodiments, the cell culture medium supplemented with stabilized ACC is suitable for growth and optionally enhancing growth of a culture of eukaryote cells, e.g. eukaryote cell, tissue or organ culture. According to some embodiments, cell culture medium supplemented with stabilized ACC is for growth of eukaryote cells. According to some embodiments, the culture of eukaryote cells is selected from a culture of animal, plant, and insect cells.

According to one embodiment, the culture of eukaryote cell, tissue or organ culture is animal cell, tissue or organ culture, stem cells, embryos and an organ. According to some embodiments, the animal is human or non-human mammal. Thus according to one embodiment, the cell culture medium supplemented with stabilized ACC is suitable for growth and optionally enhancing growth of mammal cell, tissue or organ culture, mammal stem cells, mammal embryos or a mammal organ.

According to one embodiment, the mammal is human, thus according to one embodiment, the cell culture medium according to the present invention is suitable for growth of a culture of human cell, tissue or organ culture, stem cells, embryos or an organ.

According to other embodiments, the mammal is a non-human mammal. According to one embodiment, the non-human mammal is livestock animals such as cattle, pigs, sheep, goats, horses, mules, asses, buffalo, or camels. In another embodiment, the non-human mammal is a domestic pet e.g. a cat or dog; a rodent such as a mouse, rat, guinea pig or hamster; a lagomorpha such as a rabbit; or a primate such as a monkey (e.g. macaques) or an ape (e.g. chimpanzee).

According to some embodiments, the cell culture medium according to the present invention is suitable for growth of a mammal cell culture. According to some embodiments, the mammal cell culture, either human or non-human mammal cell culture is selected from a cell culture of nerve, muscle, epithelial, bone, adipose, stem cells, gametes, and blood cell. According to one embodiment, the cell culture is a muscle cell culture. According to another embodiment, the cell culture is a nerve cell culture. According to further embodiment, the cell culture is a bone or osteocyte cell culture. According to one embodiment, the cell culture is bone marrow cell culture. According to another embodiment, the cell culture is tumor or cancer cells. According to some embodiments, the cell culture medium supplemented with ACC according to the present invention is capable of enhancing the growth of said cell culture. According to some embodiments, the cell culture is suspension or adherent cell culture.

According to some embodiments, the cell culture is a primary culture. The term "primary culture" as used herein refers to cells which were isolated from the tissue and proliferated under the appropriate conditions.

According to another embodiment, the cell culture is a cell line. The term "secondary culture" and "cell line" are used herein interchangeably and refer to a sub-cultured primary culture, i.e. primary culture transferred from one culture vessel to another culture vessel. According to some embodiments, the cell line is a finite cell lines, i.e. the cell lines which have a limited life span and go through a limited number of cell generations. According to another embodiments, the cell line is a continuous cell line, i.e. immortal cell line acquired the ability to divide indefinitely.

According to one particular embodiment, the cell line is selected from FM3, HeLa, 293, A-549, ALC, CHO, HB54, HL60, COS-7, HEK293, VERO, BHK, CV1, MDCK, 3T3, C127 MRC-5, BAE-1, SH-SY5Y, L-929, HEP G2, NSO, U937, NAMALWA, WEHI 231, YAC 1, and U 266B1 cell line. According to some embodiments, the cell culture medium supplemented with stabilized ACC is capable of enhancing growth of said cell line.

According to some embodiments, the cell culture medium of the present invention is suitable for growth of a mammal tissue culture. According to one embodiment, the mammal tissue culture is a human tissue culture. According to another embodiment, the tissue culture is a non-human mammal tissue culture. According to one embodiment, the tissue culture is selected from epithelial, connective, muscular and nervous tissue culture. According to one embodiment, the tissue culture is a nervous tissue culture. According to another embodiment, the tissue culture is a muscular tissue culture. According to yet another embodiment, the tissue culture is an epithelial tissue culture, such as nasal olfactory mucosa. According to a further embodiment, the tissue culture is a bone tissue culture.

According to some more particular embodiment, the tissue culture is selected from kidney, hepatic, glandular, brain, bone, ocular and muscle tissue culture. According to one embodiment, the epithelial tissue culture is selected from skin, stomach and intestinal lining, kidney and glands tissue culture, the muscular tissue culture is selected from smooth, skeletal and cardiac muscle tissue culture the, the nervous tissue culture is selected from brain, spinal cord and nerves tissue.

According to some embodiments, the cell culture medium supplemented with stabilized ACC is capable of enhancing growth of said tissue culture. In one embodiment, such medium is capable of enhancing regeneration of nervous tissue culture. In some embodiments, the medium is capable of enhancing regeneration of nervous culture by about 10% to about 200%, about 20% to about 150%, about 30% to about 120% or about 40% to about 100%. In other embodiments, such medium is capable of enhancing myotube formation and/or enhancing or promoting the onset of contractility of muscle cells such as also reducing the time to the onset of spontaneous contractile activity of myotubes. In one embodiment, the medium is capable of enhancing myotube formation by about 10% to about 600%, about 20% to about 500%, about 30% to about 400%, about 40% to about 300%, about 50 to about 200, about 60% to about 150% or about 70% to about 100%. The term "myotube formation" as used herein refers to a process in which myoblasts fuse into multi-nucleated fibers, myotube.

According to some embodiments, the cell culture medium of the present invention is suitable for growth of stem cells. According to some embodiments, the stem cells are human stem cells. According to another embodiment, the stem cells are non-human mammal stem cells. According to some embodiments, the stem cells are selected from embryonic, chorionic, amniotic, hematopoietic, mesenchymal, neural, glial, adult and induced pluripotent stem cells. According to one embodiment, the stem cells are embryonic stem cells. According to another embodiment, the stem cells are hematopoietic stem cells. According to a further embodiment, the stem cells are mesenchymal stem cells. According to yet another embodiment, the stem cells are pluripotent stem cells stem cells. According to some embodiments, the stem cells are adult stem cells, e.g. mesenchymal stem cells, epidermal stem cells, epithelial stem cells, hematopoietic stem cells or neural stem cells According to one embodiment, the cell culture medium of the present invention is suitable for proliferation, expansion and/or differentiation of stem cells. According to another embodiment, the cell culture medium of the present invention is capable of enhancing proliferation and/or differentiation of stem cells. According to one particular embodiment, the cell culture medium of the present invention is capable of enhancing differentiation of stem cells to osteoblast, i.e. enhancing osteoblastic differentiation.

According to some embodiments, the cell culture medium of the present invention is suitable for growth of embryos. According to one embodiment, the cell culture medium of the present invention is suitable for development of the embryos. According to another embodiment, the cell culture medium of the present invention is capable of enhancing the development of embryos. According to one embodiment, the medium is capable of enhancing embryo development by about 10% to about 300%, about 20% to about 250%, about 30% to about 200%, about 40% to about 150%, about 60% to about 100% or about 70% to about 90%. The terms "embryogenesis" and "embryo development" are used herein interchangeably and refer to the process by which the embryo forms and develops from the stage of a zygote to become an embryo, as known in the art, and includes the stages of reaching the stage of cleavage, compaction, blastocyst formation or blastocyst hatching. The terms "cleavage", "compaction", blastocyst" and "hatching" as used herein refer to the terms routinely used in embryology. The term "cleavage" is the division of cells in the early embryo. Producing a cluster of cells the same size as the original zygote. The different cells derived from cleavage are called blastomeres. The term "compaction" as used herein refers to the stage in which the dividing cells originated from a zygote maximize their contact with each other by polarization and adhesion, forming a compact ball that is held together by tight junctions. The term "blastocyst" as used herein, refers to a structure which is developed after the compaction stage and comprising an inner cell mass, which subsequently forms the embryo, and the outer layer of the blastocyst, which surrounds the inner cell mass and a fluid-filled cavity called blastocoele. The term "hatching" as used herein refers to a stage at which the embryo emerges through its outer shell (zona pellucida).

The term "enhancing embryo development" as used herein refers to promoting, enhancing or improving the rate and/or the efficacy of development process as well as to the proportion of the successfully grown and developed embryos. The enhancement is measured relatively to a control sample undergoing the same procedure but without the ACC in the growth media. According to one embodiment, the embryos are human embryos. According to another embodiment, the embryos are non-human mammal embryos. In some embodiments, the non-human mammal is selected from cattle, pigs, sheep, goats, horses, mules, donkey, buffalo, or camels. In some other embodiments, the non-human mammal is selected from a cat, dog, mouse, rat, guinea pig, hamster, rabbit, monkey or ape.

According to some embodiments, the cell culture medium is capable of improving or prolonging cryopreservation of embryos or gametes, as describe hereinabove. As used herein, the term "cryopreservation" refers to the storage of cells, such as gametes of embryos, at ultra-low temperatures, usually in liquid nitrogen (−196° C.).

According to some embodiments, the cell culture medium of the present invention is suitable for growth of gamete cells. According to one embodiment, the cell culture medium supplemented with stabilized ACC is suitable for maturation and/or preservation of gamete cells. According to one embodiment, gamete cells are oocytes. According to another embodiments, gamete cells are sperm cells. According to any one of the above embodiments, the gamete cells are gamete cells of a human or non-human mammal. According to some embodiments the non-human mammal is selected from the group consisting of livestock animals, domestic pets, rodents, wild animals and primate. In one embodiment, the livestock animals is selected from cattle, pigs, sheep, goats, horses, mules, asses, buffalo, and camels. In some other embodiments, the domestic pet is a cat or dog, the rodent is rat, mice guinea pig or hamster, the lagomorpha is a rabbit, and the primate is monkey such as macaques or ape embryo such as chimpanzee.

According to another embodiment, the gamete cells are a gamete cells of a non-mammal animal. According some embodiments, the non-mammal animal is selected from the group consisting fish, insects and birds.

According to one embodiment, the gamete cells are human sperm cells or oocytes.

According to some embodiments, cell culture medium supplemented with stabilized ACC is capable of enhancing the maturation of oocytes or sperm. According to one embodiment, the cell culture medium supplemented with stabilized ACC is capable of ameliorating the quality of sperm. The terms "enhancing maturation of sperm" and "ameliorating the quality of sperm" are used herein interchangeably and refer to improving the quality of sperm, e.g.

enhancing sperm motility, enhancing sperm progressive motility, increasing sperm count, and any combination thereof. Thus in one embodiment, the cell culture medium supplemented with stabilized ACC is capable of enhancing sperm motility, enhancing sperm progressive motility, increasing sperm count, and any combination thereof. The term "sperm motility" as used herein refers to the fraction of sperm moving among all the sperms in a given specimen sample. The term "progressive motility" as used herein refers to the fraction of sperm moving in an approximately constant direction. The terms "enhancing sperm motility" and "enhancing sperm progressive motility" as used herein, refer to increasing the fraction of motile sperm and of sperm having progressive motility, respectively. Therefore, in one embodiment, the present invention provides a method for enhancing sperm motility. According to another embodiment, the present invention provides a method for enhancing sperm progressive motility. The sperm motility, progressive motility and sperm maturation stage may be assessed by any known method in the art. For example the motility may be assessed by computer-assisted sperm analysis (CASA) method (Amann & Waberski, 2014, Theriogenology, 81: 5-17). The term "sperm sample" refers to one or more samples comprising sperm. The sperm sample may be semen obtained from a subject or processed semen, liquefied semen, sedimented and optionally resuspended sperm, etc. According to some embodiments, increasing sperm count comprises increasing the sperm count in motility or progressive motility procedure. According to one embodiments, the motility or progressive motility procedure is a swim up procedure.

According to some embodiments, the cell culture medium of the present invention is suitable for growth of organ tissue or organ. According to some embodiments, the organ tissue or organ is selected from ovary, cornea, heart, kidney, pancreas, liver, spleen, lung, testicle, bladder, and blood vesicles. In one particular embodiment, the organ tissue or organ is an ovary. Thus the cell culture medium of the present invention is capable of enhancing preservation or maintaining organ tissue or organ.

According to some embodiments, the cell culture medium of the present invention is suitable for growth of plant cells. According to some embodiments, the cell culture medium of the present invention is suitable for growth plant cell culture. According to another embodiment, the cell culture medium of the present invention is suitable for growth plant tissue culture. The term "plant cell culture" refers to plant cells derived from tissue or cells of plants, which are then cultured in a container or recipient. The term "plant tissue culture" include callus tissues (callus), differentiated cultured tissues or a cultured organ tissue. The term "callus" refers to a mass of unorganized parenchymatic cells derived from plant tissue (explants).

According to another embodiment, the cell culture medium of the present invention is suitable for growth of insect cells. According to one embodiment, the insect cells are insect cell culture e.g. insect cell lines. The cell types are as describe hereinabove. In one particular embodiment, the cell lines are selected from Sf 9, Sf 21 and high-five cell lines. According to another embodiment, the cell culture medium of the present invention is suitable for growth insect tissue culture. According to further embodiment, the insect cells are insect organ culture.

According to some embodiments, the cell culture is suspension or adherent cell culture.

In one embodiment, the cell culture medium supplemented with stabilized ACC is capable of enhancing growth of plant cell or tissue culture, or capable of enhancing growth of insect cell, tissue or organ culture.

According to any one of the above embodiments, the cell culture medium of the present invention, suitable to growth of animal, plant or insect cells, tissue or organ cultures may be a natural medium or an artificial medium, supplemented with ACC stabilized by at least one stabilizing agent, as defined in the present invention. According to some embodiments, the medium is a natural medium supplemented with ACC stabilized by at least one stabilizing agent. According to some embodiments, the natural medium comprises biological fluid selected from plasma, serum, lymph, human placental cord serum, and amniotic fluid. According to another embodiment, the natural medium comprises tissue extracts such as extract of liver, spleen, tumors, leucocytes and bone marrow, extract of bovine embryo and chick embryos. According to a further embodiment, the natural medium comprises coagulants or plasma clots. According to some embodiments, the medium is an artificial medium supplemented with ACC stabilized by at least one stabilizing agent. According to one embodiment, the artificial medium is a balanced salt solution. Examples of balanced salt solution are PBS, DPBS, HBSS, EBSS Tyrode's T6, WM1, Pool's P1, Quinn's HTF, and Gardner's G1. According to another embodiment, the artificial medium is a basal medium. According to some embodiments, the medium may be further supplemented as well known in the art. According to one embodiment, the medium is supplemented with serum, e.g. fetal bovine serum. According to a further embodiment, the artificial medium is a complex medium.

The term "basal medium" as used herein refers to a nutrient mixture of inorganic salts, sugars, amino acids, optionally also containing vitamins, organic acids and/or buffers. Basal media together with supplements provide the nutrients necessary to support cell life, growth and reproduction. The choice of basal medium used should be appropriate for the culture.

According to one embodiment, the artificial medium is a serum free medium. According to a further embodiment, the artificial medium is a medium with reduced serum content. According to another embodiment, the artificial medium is a protein-free media.

Examples of the cell media that may be supplemented with ACC stabilized by at least one stabilizer and used according to the present invention are Dulbecco's Modified Eagle's Medium (DMEM), Minimum Essential Medium (EMEM), RPMI 1640 medium (developed at Roswell Park Memorial Institute), and Basal Medium Eagle (BME). Further examples of media according to the present invention are Ham's Nutrient Mixtures such as Ham's F-10, Ham's F-12, DMEM/F-12 (DMEM and Ham's F-12). Other examples are Iscove's Modified Dulbecco's Medium (IMDM), opti-MEM and Glasgow's MEM (GMEM). Examples of media suitable for insect cells growth are IPL-41 Insect Medium, Schneider's Drosophila medium, Grace's Insect medium, Serum-free Insect Media, Sf-900, TC-10, Shields and Sang M3 Insect Medium, TC-100 Insect Medium, TNM-FH Insect Medium and IPL-10. Examples of media suitable for embryos growth are monoculture media such as SAGE 1-Step™ or sequential Media such as Quinns Advantage™ Sequential Media (ORIGIO). Examples of media suitable for plant cell growth are Murashige and Skoog (MS), B5, N6 and Nitsch's medium.

Other examples of media are Modified Medium, NCTC Medium, MegaCell Media, Claycomb, Click's Medium, L-15 Medium, Medium 199, MCDB Media, Ames' Media, BGJb Medium (Fitton-Jackson Modification), Click's Medium, CMRL-1066 Medium, McCoy's 5A Modified Medium, NCTC Medium, Swim's S-77 Medium, Waymouth Medium, William's Medium E and in vitro fertilization media such as Global®, GM501, SSM™, Cleavage K-SICM, Blastocyst K-SIBM, Quinns Advantage®Cleavage, Quinns Advantage®Blastocyst, FERTICUL™IVF Medium, FERTICULT™ G3 Medium, IVC-TWO™, IVC-THREE™, ECM®, MultiBlast®, EmbryoAssist™, BlastAssist™, ISM1, ISM2, G-I TMPLUS, G-2™PLUS, IVF™, and CCM™. Further examples of media are media for sperm separation such as ISolate®, PureCeption™, Multipurpose Handling Medium® (MHM®), media for sperm wash such as Quinns™ Sperm Washing Medium, Multipurpose Handling Medium® (MHM®) or Modified HTF Medium with Gentamicin, medium for sperm capacitation such as Biggers-Whitten-Whittingham (BWW) medium, Ham's-F10 and a modified Tyrode's medium (HSM), and media for maturation which enables the culture of immature oocytes to fully developed embryos suitable for transfer. In other embodiments, the medium is a medium for oocytes maturation such as SAGE™ In-Vitro Maturation Media (IVM) and BO-IVM Oocyte maturation medium, medium for fertilization, medium for embryo development, Media for gamete Handling, medium for Preimplantation genetic diagnosis (PGD) or a medium for embryo or/and gamete maturation, handling and/or cryopreservation. Thus according to one embodiment, the cell culture medium is selected from DMEM, RPMI 1640, MEM, IMDM, L-15 Medium (Leibovitz), MCDB Medium, Medium 199, opti-MEM and DMEM/F-12, Schneider's Drosophila medium, Grace's Insect medium, IPL-41 Insect Medium Sf-900, Serum-free Insect Media, Shields and Sang M3 Insect Medium, TC-100 Insect Medium, TNM-FH Insect Medium, Ham's F-12, Ham's F-10, GMEM, Ames' Medium, Basal Medium Eagle (BME), Claycomb, Click's Medium, Glasgow Minimum Essential Medium (GMEM), MegaCell Media, McCoy's 5A Modified Medium, NCTC Medium, Williams' Medium E, Waymouth Medium, TC-10 and IPL-10 medium. According to another embodiment, the cell culture medium is selected from DMEM, RPMI 1640, MEM, IMDM, opti-MEM, GMEM, Ham's F-12 and DMEM/F-12, Schneider's Drosophila medium, Grace's Insect medium, Sf-900, TC-10, IPL-10 medium, media for sperm separation, wash or maturation such as ISolate®, PureCeption™, Multipurpose Handling Medium® (MHM®), Quinns™ Sperm Washing Medium, Multipurpose Handling Medium® (MHM®), Biggers-Whitten-Whittingham (BWW) medium, Ham's-F10 and a modified Tyrode's medium (HSM), and modified HTF medium with Gentamicin, medium for fertilization, medium for embryo development, and medium for embryo or/and gamete maturation, handling and/or cryopreservation.

According to some embodiments, the cell culture medium supplemented by stabilized ACC of the present invention is suitable for growth of unicellular eukaryotes. According to one embodiments, the unicellular eukaryotes are yeasts such as *Saccharomyces*, more particular *Saccharomyces cerevisiae*. According to one embodiment, the cell culture medium of the present invention suitable for growth of unicellular eukaryotes, e.g. *Saccharomyces cerevisiae*, is selected from yeast extract peptone dextrose (YPD), Yeast extract-peptone-glycerol (YPG) and Yeast extract-peptone-dextrose (YPAD) media. In one embodiment, the cell culture medium supplemented with stabilized ACC is capable of enhancing the growth of yeast.

According some embodiments, the cell culture medium of the present invention is suitable for growth of prokaryotes.

In particular embodiment, the cell culture medium of the present invention is suitable for growth of microorganisms. In some embodiments the microorganisms are microbiome microorganisms. In some embodiments the microorganisms are bacteria. Thus, in particular embodiment, the cell culture medium of the present invention is suitable for growth of bacteria. In some embodiments, the bacteria is *E. coli* or probiotic bacteria such bacteria of *Bifidobacterium* and *Lactobacillus* genera. Additional examples of probiotic bacteria species strains are *Lactobacillus Paracasei, Bifidobacterium Longum, Lactobacillus Johnsonii, Lactobacillus Fermentum, Pediococcus Acidlacti* such as: *Lactobacillus Acidophilus, Lactobacillus Rhamnosus* GG, *Lactobacillus Helveticus, Bifidobacterium Infantis, Bifidobacterium Lactis, Lactobacillus Bulgaricus, Lactobacillus Silivarius, Lactobacillus Plantarum, Lactobacillus Reuteri, Lactobacillus Casei, Bifidobacterum Bifidum, Saccharomyces Boulardii, Streptococcus Thermophilus, Bifidobacterum Breve, Bacillus Coagulans, Lactobacillus Brevis*, According to some embodiments, the medium suitable for growth of bacteria is selected from LB and M9. In one embodiment, the cell culture medium supplemented with stabilized ACC is capable of enhancing the growth of bacteria.

According some embodiments, the cell culture medium of the present invention is suitable for growth of archaea. In one embodiment, the cell culture medium supplemented with stabilized ACC is capable of enhancing the growth of archaea.

According to any one of aspects and embodiments of the present invention, ACC is stabilized by at least one stabilizing agent. The terms "stabilizing agent" and "stabilizer" are used herein interchangeably and refer to any substance that contributes to preserving calcium carbonate in the amorphous state during ACC production, formulating storage and/or use. In certain embodiments, the stabilizing agent is a single agent. In other embodiments, use of several stabilizing agents is encompassed. The terms "stabilized ACC" and "ACC stabilized by at least one stabilizer" may be used in some embodiments, interchangeably.

The stabilizer may comprise a molecule having one or more functional groups selected from, but not limited to, hydroxyl, carboxyl, ester, amine, phosphino, phosphono, phosphate, sulfonyl, sulfate, or sulfino groups. The hydroxy bearing compounds, combined with the hydroxide, optionally also bear other functions like carboxyl, etc. but with the hydroxyl not being esterified.

According to some embodiments, the stabilizer has low toxicity or no toxicity to mammalian cells or organism, and in particular to a human being. According to some embodiments, the stabilizer is of food, nutraceutical or pharmaceutical grade.

In certain embodiments, the ACC stabilizing agent is independently at each occurrence, an organic acid; phosphorylated, phosphonated, sulfated or sulfonated organic compound; phosphoric or sulfuric ester of a hydroxyl carboxylic acid; an organoamine compound; an organic compound comprising a hydroxyl; an organophosphorous compound or a salt thereof; phosphorylated amino acids and derivatives thereof, a bisphosphonate; an organophosphate compound; an organophosphonate compound; organic polyphosphate, an inorganic polyphosphate, an inorganic phosphorous acid, an organic compound having multiple functional groups as defined above; an inorganic phosphate and polyphosphate compound; an organic compound having a polyphosphate chain; an organic surfactant; a bio-essential inorganic ion; saccharides and derivatives thereof, proteins, phosphorylated proteins, natural and synthetic biopolymers and derivatives thereof or any combination thereof. According to some embodiments, the stabilizer may have also a pharmaceutical activity, e.g. bisphosphonate, or ATP.

Thus in one embodiment, the stabilizing agent is selected from the group consisting of polyphosphate such as inorganic polyphosphate, organic acids, phosphorylated, phosphonated, sulfated or sulfonated organic compounds, phosphoric or sulfuric esters of hydroxy carboxylic acids, phosphorylated amino acids, bisphosphonate, organic polyphosphate, saccharides and derivatives thereof, proteins, peptides, phosphorylated proteins, phosphorylated peptides, and any combinations thereof. According to another embodiment, the stabilizing agent is selected from the group consisting of phosphoserine, adenosine triphosphate, adenosine diphosphate, phytic acid, citric acid, etidronic acid, pyrophosphate, polyphosphate, triphosphate, ethanol, hexamethaphosphate, chitin, and any combination thereof.

According to some embodiments, the stabilizer is an organic acid. According to certain embodiments, the organic acid is selected from ascorbic, citric, lactic or acetic acid, oxalic acid, malonic acid, glutaconic acid, succinic acid, maleic acid, lactic acid, glutamic acid, aconitic acid, and optionally include compounds having at least two carboxylic groups optionally having molecular weight not larger than 250 g/mol, such as citric acid, tartaric acid, malic acid, etc. According to one particular embodiment, the stabilizer is citric acid.

In another embodiment, the phosphoric ester of hydroxyl carboxylic acids is a phosphoenolpyruvate. In another embodiment, the phosphoric or sulfuric esters of hydroxyl carboxylic acids comprise amino acids. Examples of such esters are phosphoserine, phosphothreonine, sulfoserine, sulfothreonine and phosphocreatine.

In another embodiment, the stabilizer is a saccharide. According to one embodiment, the saccharides is selected from mono-, di- tri-, oligo-, and polysaccharides like sucrose mannose, glucose, chitosan and chitin. Stabilizer may be in some embodiments polyols like glycerol. According to another embodiment, the stabilizer is an amino acids such as serine or threonine. Each possibility represents a separate embodiment, of the present invention.

Non-limiting examples of natural and synthetic biopolymers and derivatives are polynucleotides and glycoproteins.

Some specific unlimited examples for such ACC stabilizers that were approved for food consumption, found in natural food or in human beings include phytic acid, citric acid, sodium pyrophosphate dibasic, adenosine 5'-monophosphate (AMP) sodium salt, adenosine 5'-diphosphate (ADP) sodium salt and adenosine 5'-triphosphate (ATP) disodium salt hydrate, phosphoserine, phosphorylated amino acids, food grade surfactants, sodium stearoyl lactylate, and combinations thereof.

According to some embodiments, the stabilizer comprises at least one component selected from phosphoric or sulfuric esters of hydroxyl carboxylic acids, such as phosphoenolpyruvate, phosphoserine, phosphothreonine, sulfoserine or sulfothreonine and saccharides, selected from mono-, di-, tri-, oligo- and poly-saccharides, for example, sucrose, mannose, glucose. The hydroxyl bearing compound may further comprise at least one alkali hydroxide, such as sodium hydroxide, potassium hydroxide and the like. The phosphorylated acids may be present in oligopeptides and polypeptides. In other embodiments, of the invention, the stabilizer is an organic acid selected from monocarboxylic acid or multiple carboxylic acid, e.g. dicarboxylic acid or tricarboxylic acid. Each possibility represents a separate embodiment, of the invention. The organic acid may be as defined above.

In some embodiments, of the invention, the ACC stabilizer is selected from phosphorylated amino acids, polyols and combinations thereof. In some embodiments, the stable ACC comprises a phosphorylated compound as a stabilizer wherein the phosphorylation is performed on the hydroxyl group of an organic compound. In some embodiments, the stable ACC comprises a stabilizer selected from the group consisting of citric acid, phosphoserine, phosphothreonine and combinations thereof. The non-limiting examples of stabilizers containing phosphate, phosphite, phosphonate groups and salts or esters thereof include phytic acid, dimethyl phosphate, trimethyl phosphate, sodium pyrophosphate, tetraethyl pyrophosphate, ribulose bisphosphate, etidronic acid and other medical bisphosphonates, 3-phosphoglyceric acid salt, glyceraldehyde 3-phosphate, 1-deoxy-D-xylulose-5-phosphate sodium salt, diethylene triamine pentakis(methylphosphonic acid), nitrilotri(methylphosphonic acid), 5-phospho-D-ribose 1-diphosphate pentasodium salt, adenosine 5'-diphosphate sodium salt, adenosine 5'-triphosphate disodium salt hydrate, α-D-galactosamine 1-phosphate, 2-phospho-L-ascorbic acid trisodium salt, α-D-galactose 1-phosphate dipotassium salt pentahydrate, α-D-galactosamine 1-phosphate, O-phosphorylethanolamine, disodium salt hydrate, 2,3-diphospho-D-glyceric acid pentasodium salt, phospho(enol)pyruvic acid monosodium salt hydrate, D-glyceraldehyde 3-phosphate, sn-glycerol 3-phosphate lithium salt, D-(−)-3-phosphoglyceric acid disodium salt, D-glucose 6-phosphate sodium salt, phosphatidic acid, ibandronate sodium salt, phosphonoacetic acid, DL-2-amino-3-phosphonopropionic acid or combinations thereof. The bio-essential inorganic ions may include, inter alia, Na, K, Mg, Zn, Fe, P, S, N; P or S in the phase of oxides; or N as ammonia or nitro groups.

The stabilizer may further include phosphonate compounds such as, but not limited to bisphosphonates, polyphosphates, such as, but not limited to pyrophosphate or polyphosphonates or organo polyphosphates, such as, but not limited to, adenosine diphosphate (ADP) or adenosine triphosphate (ATP).

Optionally ACC is stabilized by a combination of phosphoserine and citric acid. In another embodiment, the ACC is stabilized by triphosphate and citric acid.

The ACC may be stabilized by more than one stabilizers, e.g. two stabilizers. The stable ACC can comprise more than two stabilizers, wherein one or more stabilizers are added to the ACC during the formation and precipitation of the ACC; hence constituting "internal" stabilizers, and another one or more stabilizers are added at the ACC particle surfaces after their formation; hence, constituting "external" stabilizers. Further examples for stable ACC and the preparation thereof may be found in International Patent Applications Nos. WO 2009/053967, WO 2014/024191 and WO 2016/193982.

In some embodiments, the stabilizing agent is a protein. In one embodiment, the protein is a naturally produced and purified protein. In another embodiment, the protein is synthetically produced protein. In some embodiments, the protein is selected from GAP65, GAP22, GAP21 and GAP12 proteins. In another embodiment, the proteins are selected from CqCDA1, chotinase 2, beta-N-acetylglucosaminidase, GAMP-like, chitin-binding protein, CqCBP, CAP10, GAP 18.2, GAP 02526, CqHc1, CqHc2, CqHc3, CqHc4, CqHc5, CqHc6, CqHc7, cryptocyaninl, cyclophilin, cystatin 1, cycstatin 2, LPS-BP, LEA protein and crystacyanin, optionally said proteins are originated from *C. quadricarinatus*. According to certain embodiments, the proteins are phosphorylated proteins.

In some embodiments, the stabilizing agent is selected from a polyphosphate, phosphorylated amino acids, organic acids, phosphorylated, phosphonated, sulfated or sulfonated organic compounds, phosphoric or sulfuric esters of hydroxy carboxylic acids, bisphosphonate, saccharides, derivatives thereof, proteins, phosphorylated proteins, natural and synthetic biopolymers and derivatives thereof and any combinations thereof. In other embodiments, the stabilizing agent is selected from phosphoserine, triphosphate, adenosine triphosphate, adenosine diphosphate, phytic acid, citric acid, etidronic acid, pyrophosphate, ethanol, hexamethaphosphate, chitin, and any combination thereof.

In some embodiments, the stabilizing agent is selected from organic acids, phosphorylated organic acids, phosphoric or sulfuric esters of hydroxy carboxylic acids, phosphorylated amino acids, bisphosphonate, organic polyphosphate, saccharides, derivatives thereof, proteins and any combinations thereof.

According to some embodiments, the at least one stabilizer is selected from the group consisting of a polyphosphate, bisphosphonate, phosphorylated amino acid, citric acid, and any combination thereof. In some embodiments, more than one stabilizers, e.g. 2, 3 or 4 stabilizers are added.

According to some embodiments, the stabilizer is a polyphosphate or pharmaceutically acceptable salts thereof. According to some embodiments, the polyphosphate is physiologically compatible, water soluble polyphosphate salt selected from the group consisting of sodium, potassium and any other essential cation of polyphosphate. In one embodiment, the polyphosphate is organic or inorganic polyphosphate. The term "polyphosphate" as used herein refers to polymeric esters of $PO_4$. According to some embodiments, the polyphosphate is physiologically compatible water soluble polyphosphate salt selected from the group consisting of sodium and potassium polyphosphate. In some embodiments, the polyphosphate is an inorganic polyphosphate or pharmaceutically acceptable salts thereof. Not-limiting examples of such salt are Na, K, Mg, Mn and Zn. According to some embodiments, the inorganic phosphate comprise 2 to 10 phosphate groups, e.g. 2, 3, 4, 5, 6, 7, 8, 9, or 10 phosphate group. According to some embodiments, the polyphosphate is selected from pyrophosphate, triphosphate, and hexametaphosphate. According to one embodiment, the stabilizer is pyrophosphate or pharmaceutically acceptable salts thereof such as sodium pyrophosphate. According to another embodiment, the stabilizer is triphosphate or pharmaceutically acceptable salts thereof such as sodium triphosphate. The term "triphosphate" and "tripolyphosphate" are used herein interchangeably. According to a further embodiment, the stabilizer is hexametaphosphate or a pharmaceutically acceptable salt thereof such sodium hexametaphosphate.

According to some embodiments, the stabilizer is a bisphosphonate or pharmaceutically acceptable salts thereof. The not-limiting examples of salt are Na, K, Mg, Mn and Zn.

The term "bisphosphonate" as used herein refers to organic compounds having two phosphonate ($PO(OH)_2$) groups. The term further relates to compounds having a backbone of PO3-organic-PO3. Most typical is a series of bisphosphonates that are used as pharmaceuticals for treating osteoporosis. According to some embodiments, the bisphosphonate is selected from the group consisting of etidronic acid, zoledronic acid, medronic acid, alendronic acid and a pharmaceutically acceptable salt thereof. According to some embodiments, the stabilizer is an etidronic acid or a pharmaceutically acceptable salt thereof. According to another embodiment, the stabilizer is a zoledronic acid or a pharmaceutically acceptable salt thereof. According to a further embodiment, the stabilizer is a medronic acid or a pharmaceutically acceptable salt thereof. According to certain embodiments, the stabilizer is alendronic acid or a pharmaceutically acceptable salt thereof.

According to certain embodiments, the stabilizer is a phosphorylated amino acid. According to one embodiment, the phosphorylated amino acid is phosphoserine. According to another embodiment, the phosphorylated amino acid is phosphothreonine.

According to some embodiments, the ACC composition comprises a combination of the stabilizers disclosed above.

According to some embodiments, the stabilizer is polyphosphate or a bisphosphonate as defined hereinabove, and the molar ratio between P atoms of the stabilizer and Ca atoms of the ACC (P:Ca molar ratio) is about 1:90 to 1:1. In one embodiment, the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In certain embodiments, the P:Ca molar ratio is about 1:28 to about 1:3. In other embodiments, the P:Ca molar ratio is about 1:25 to about 1:4. In further embodiment, the P:Ca molar ratio is about 1:20 to about 1:5. In another embodiment, the P:Ca molar ratio is about 1:20 to about 1:6. In a particular embodiment, the P:Ca molar ratio is about 1:15 to about 1:5. In another particular embodiment, the P:Ca molar ratio is about 1:25 to about 1:5. According to some embodiments, such polyphosphate is pyrophosphate, triphosphate, hexametaphosphate or a pharmaceutically acceptable salt thereof. According to another embodiments, the bisphosphonate is alendronic acid, etidronic acid, zoledronic acid or medronic acid and the P:Ca molar ratio is as defined hereinabove.

According to some embodiments, the calcium content (Ca content) stabilized ACC comprising polyphosphate or bisphosphonate is about 1 wt % to about 39 wt %, about 5 wt % to about 39 wt %, about 10% to about 39 wt %, about 15% to about 39 wt %, about 20 wt % to about 38 wt %, about 25 wt % to about 38 wt %, or about 30 to about 38. The terms "Ca content" and "calcium content" is used herein interchangeably and refer to the content of calcium of the ACC in the final composition.

In certain embodiments, the P:Ca molar ratio is about 1:40 to about 1:1, and the Ca content is about 20 wt % to about 39 wt %. In some embodiments, the molar ratio is 1:28 to about 1:3, and the Ca content is about 30 wt % to about 38 wt %. In another embodiment, the molar ratio is 1:25 to about 1:5, and the Ca content is about 30 wt % to about 36 wt %.

According to some embodiments, the stabilizer is selected from the group consisting of a polyphosphate, phosphorylated amino acid, bisphosphonate, citric acid, tartaric acid and any combination thereof. According to one embodiments, the polyphosphate is selected from the group consisting of triphosphate, pyrophosphate, and hexametaphosphate, the phosphorylated amino acid is phosphoserine or phosphothreonine, and the bisphosphonate is selected from the group consisting of alendronate, etidronic acid, zoledronic acid and medronic acid.

According to some embodiments, the stabilized ACC comprises less than 20 wt %, less than 15 wt %, less than 10 wt %, or less than 5 wt % of the stabilizing agent. In some embodiments, the stabilized ACC comprises up to 5 wt % of the stabilizing agent.

According to one embodiment, the average diameter average diameter of the stabilized ACC primary particles is about 10 nm to about 5 µm. According to another embodiment, the average diameter average diameter of the ACC primary particles is about 30 nm to about 400 nm. According to yet another embodiment, the average diameter average diameter of the ACC primary particles is about 30 nm to 350 nm. According to certain embodiments, the average diameter of the ACC primary particles is about 35 nm to 300 nm, 40 nm to about 250 nm, about 45 nm to about 200 nm, about 50 nm to about 150 nm or about 60 nm to about 100 nm. According to still another embodiment, the primary particles of ACC are aggregated and an average diameter average diameter of the aggregates is between 0.5 µm and 300 µm. According to one further embodiment, the diameter of aggregates of the ACC primary particle is about 1 to about 100 µm, about 10 to about 50 µm or about 20 to about 40 µm. According to another embodiment, the average diameter average diameter of the aggregates of the ACC primary particle is between 1 µm and 10 µm.

According to any one of the above embodiments, the final concentration of stabilized ACC in the cell culture medium is about 0.1 to about 20 mM, about 0.5 to about 15 mM, about 1 to about 10 mM, about 2 to about 8 mM, about 3 mM to about 6 mM or about 4 mM to about 5 mM. In more particular embodiment, the stabilized ACC is present in a concentration of 0.5 to about 4 mM, about 1 to about 3 mM, about 1.5 to about 2.5, or about 1, 1.5, 2 or 2.5 mM. According to some embodiments, the concentration of stabilized ACC in the cell culture medium is about 0.0001% w/v to about 1% w/v about 0.0005% w/v to about 0.5% w/v, about 0.001% w/v to about 0.1% w/v, about 0.005% w/v to about 0.05% w/v, about 0.01% w/v to about 0.03% w/v.

According to some more specific embodiments, the present invention provides a cell culture medium supplemented with ACC stabilized by at least one stabilizing agent, wherein the stabilizing agent is selected from polyphosphate such as inorganic polyphosphate, phosphorylated amino acid, bisphosphonate, organic acid and any combination thereof; and the cell culture medium is suitable for growth of (i) muscle, nerve or bone cell or tissue culture, (ii) human or non-human mammal embryos, (iii) stem cells, (iv) gamete cells, or (v) ovaries. According to some embodiments, the stabilizing agent is a phosphoserine. According to another embodiment, the stabilizing agent is a triphosphate. According to yet another embodiment, the stabilizing agent is a combination of phosphoserine with organic acid, such as citric acid. According to a further embodiment, the stabilizing agent is a combination of triphosphate such as sodium triphosphate with organic acid, such as citric acid. According to one embodiment, such cell culture medium is suitable for growth of muscle, nerve or bone cell or tissue cultures. According to more particular embodiment, the cell culture medium is capable of supporting and enhancing growth, e.g. proliferation, maturation, development or differentiation of the cells. According to one embodiment, the cells are nerve cells and more particular damaged nerve cells. Thus according to one embodiment, such cell culture medium is capable of enhancing regeneration of damaged nerve cells. According to another embodiment, the cells are muscle cells, in particular dystrophic muscle cells such as Duchenne muscular dystrophic cells. Thus, according to one embodiment, the cell culture medium is capable of enhancing myotube formation and/or contractility onset. According to another embodiment, such cell culture medium is suitable for growth of human or non-human mammal embryos. In one particular embodiment, the cell culture medium is suitable for growth of human embryos. In even more particular embodiment, the cell culture medium is capable of enhancing development of human embryos. According to another embodiment, such cell culture medium is suitable for growth of human or non-human mammal gamete cells. In one particular embodiment, the cell culture medium is suitable for maturation of human gamete cells. In even more particular embodiment, the cell culture medium is capable of enhancing maturation of human gamete cells. According to another embodiment, the cell culture medium is capable of maturation of human sperm, e.g. enhancing sperm motility, enhancing sperm progressive motility, increasing sperm count, and any combination thereof. According to further embodiment, such cell media culture is suitable for growth of stem cells, and in particular human stem cells. According to some embodiments, the stem cells are selected from embryonic, chorionic, amniotic, hematopoietic, mesenchymal, neural, glial, adult and induced pluripotent stem cells. According to one embodiment, such cell culture medium is suitable for proliferation and/or differentiation of stem cells. According to one particular embodiment, such cell culture medium is capable of enhancing differentiation of stem cells such as MBA13 to osteoblasts. According to some embodiments the final concentration of stabilized ACC in the cell culture medium is about 0.1 to about 8 mM, about 0.5 to about 6 mM, about 1 to about 5 mM, or about 2 to about 4 mM. According to one embodiment, the cell culture medium supplemented with stabilized ACC is capable of enhancing the growth parameters, e.g. proliferation, maturation, development or differentiation of the cells by about 10% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%.

According to some embodiments, the present invention provides a cell culture medium such as cleavage, monoculture or sequential medium supplemented with ACC stabilized by at least one stabilizing agent, wherein the agent is phosphoserine or sodium triphosphate, optionally in combination with citric acid, the final concentration of stabilized ACC in the cell culture medium is about 0.1 to about 8 mM, about 0.5 to about 6 mM, about 1 to about 5 mM, or about 2 to about 4 mM, and the cell culture medium is capable of enhancing growth such as development of human embryos.

According to some embodiments, the present invention provides a cell culture medium such as media for sperm separation, wash or maturation such as ISolate®, PureCeption™, Multipurpose Handling Medium® (MHM®), Quinns™ Sperm Washing Medium, Multipurpose Handling Medium® (MHM®) and Modified HTF Medium with Gentamicin, supplemented with ACC stabilized by at least one stabilizing agent, wherein the agent is phosphoserine or sodium triphosphate, optionally in combination with citric acid, the final concentration of stabilized ACC in the cell culture medium is about 0.1 to about 8 mM, about 0.5 to about 6 mM, about 1 to about 5 mM, or about 2 to about 4 mM, and the cell culture medium is capable of enhancing maturation of sperm cells, e.g. enhancing sperm motility, enhancing sperm progressive motility, increasing sperm count, and any combination thereof.

According to other embodiments, the present invention provides a cell culture medium supplemented with ACC stabilized by at least one stabilizing agent, wherein the agent is phosphoserine, etidronic acid or sodium triphosphate, optionally in combination with citric acid, and the cell culture medium is capable of enhancing regeneration of nerve cells.

According to other embodiments, the present invention provides a cell culture medium such as DMEM/F12 or DMEM/F12 optionally supplemented with horse serum (HS), L-Glutamine, Gentamycine, and Insulin, wherein said medium is further supplemented with ACC stabilized by phosphoserine, etidronic acid or sodium triphosphate, optionally in combination with citric acid, wherein the final concentration of stabilized ACC in the cell culture medium is about 0.1 to about 8 mM, about 0.5 to about 6 mM, about 1 to about 5 mM, or about 2 to about 4 mM and said cell culture medium is capable of enhancing myotube formation and/or the onset of contractility in skeletal muscle cell e.g. in case of Duchenne muscular dystrophy.

According to other embodiments, the present invention provides a cell culture medium supplemented with ACC stabilized by phosphoserine, etidronic acid or sodium triphosphate, optionally in combination with citric acid, and said cell culture medium is capable of enhancing differentiation of stem cells, in particular differentiation of MBA13 to osteoblasts, wherein the final concentration of stabilized ACC in the cell culture medium is about 0.1 to about 8 mM, about 0.5 to about 6 mM, about 1 to about 5 mM, or about 2 to about 4 mM.

According to other embodiments, the present invention provides a cell culture medium such as DMEM/F12 or DMEM/F12 with 10% fetal bovine serum (FBS), 2 mM glutamine, 25 µg/mL gentamicin and 0.3-0.5% NVR-Gel, wherein said medium is further supplemented with ACC stabilized by phosphoserine, etidronic acid or sodium triphosphate, optionally in combination with citric acid, wherein the final concentration of stabilized ACC in the cell culture medium is about 0.1 to about 8 mM, about 0.5 to about 6 mM, about 1 to about 5 mM, or about 2 to about 4 mM and said cell culture medium is capable of enhancing preservation of ovaries.

According to another aspect, the present invention provides amorphous calcium carbonate (ACC) stabilized by at least one stabilizing agent, for use as a supplement to a cell culture medium. The terms "supplement" and "cell culture medium supplement" are used herein interchangeably and refer to one or multiple components for addition to cell culture media. In one particular embodiment, the term refers to stabilized ACC added or intended to be added to a cell culture medium. According to one embodiment, the stabilized ACC is added to the medium during the preparation of the medium. According to another embodiment, the ACC is added to the medium prior use.

According to one embodiment, the stabilized ACC is for use as a supplement to a cell culture medium suitable for growing a biological culture.

According to some embodiments, the stabilized ACC of the present invention when added to the cell culture media enhances the growth of cells. Therefore, in one embodiment, the stabilized ACC for use as a supplement to cell culture medium is capable of enhancing the growth of cells. In one embodiment, the stabilized ACC used as a supplement to a cell culture medium enhances proliferation, maturation, propagation, regeneration, development and/or differentiation of cells, tissues and organs. According to one embodiment, the ACC for use as a supplement the cell culture medium of the present invention, is capable of enhancing differentiation of stem cells. According to another embodiment, such ACC for use as a supplement the cell culture medium is capable of enhancing proliferation of cells. According to yet another embodiment, ACC for use as a supplement to cell culture medium is capable of enhancing maturation, e.g. of gametes, or enhancing development of cells, e.g. of embryos. According to certain embodiments, ACC for use as a supplement to cell culture medium is capable of enhancing regeneration of cells.

According to one embodiment, the cell culture medium supplemented with stabilized ACC is capable of enhancing the growth parameters, e.g. proliferation, maturation, development or differentiation of the cells by about 10% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%.

According to some embodiments, the cell culture medium supplement may be added to any known cell culture medium. According to some embodiments, the media is as defined hereinabove. According to one embodiment, the cell culture medium is selected from a natural medium and artificial medium. According to one embodiment, the media is suitable for growth any biological culture, e.g. cell culture, tissue culture, organ culture, unicellular eukaryotes or microorganisms such as bacteria. According to one embodiment, the cell culture medium is suitable for growth of a culture selected from a culture of animal, plant or insect cells, tissues and/or organs. According to another embodiment, the cell culture medium is suitable for growth of bacteria or yeast.

According so some embodiments, the culture of animal cells is selected from a cell culture, tissue culture, organ culture, stem cells, gametes, embryos and an organ of human or non-human mammal. According to other embodiments, the mammal is a non-human mammal, e.g. livestock animals such as cattle, pigs, sheep, goats, horses, mules, asses, buffalo, or camels; a domestic pet e.g. a cat or dog; a rodent such as a mouse, rat, guinea pig or hamster; a lagomorpha such as a rabbit; or a primate such as a monkey (e.g. macaques) or an ape (e.g. chimpanzee). According to some embodiments, the stabilized ACC is for use as a supplement to cell culture suitable for growth of a primary or secondary culture. According to some embodiments, the stabilized ACC is capable of enhancing growth of said cell line. According to some embodiments, the stabilized ACC is for use as a supplement to cell culture medium suitable for growth of a mammal tissue culture. According to some embodiments, the stabilized ACC is for use as a supplement to cell culture medium suitable for growth of stem cells. According to another embodiment, the stem cells are human or non-human mammal stem cells.

According to some embodiments, the stabilized ACC is for use as a supplement to cell culture medium suitable for growth of embryos. According to one embodiment, the cell culture medium of the present invention is suitable for maturation and development of the embryos. According to another embodiment, stabilized ACC for use as a supplement to cell culture medium is capable of enhancing the development of embryos. According to one embodiment, the embryos are human embryos. According to another embodiment, the embryos are non-human mammal embryos.

According to some embodiments, the stabilized ACC is for use as a supplement to cell culture medium suitable for growth of gametes. According to one embodiment, the cell culture medium of the present invention is suitable for maturation or preservation of gamete. According to another embodiment, stabilized ACC for use as a supplement to cell culture medium is capable of enhancing the maturation or preservation of gametes, e.g. maturation or preservation of sperm or oocytes.

According to another embodiment, stabilized ACC for use as a supplement to cell culture medium is capable of enhancing cryopreservation of embryos or gametes, as describe hereinabove According to some embodiments, enhancing maturation of sperm is selected from enhancing sperm motility, enhancing sperm progressive motility, increasing sperm count, and any combination thereof. According to one embodiment, the sperm is human sperm. According to another embodiment, the sperm is a non-human mammal sperm. According to some embodiments, the stabilized ACC is for use as a supplement to cell culture medium suitable for growth of organ culture or organ. According to some embodiments, the organ tissue or organ is selected from ovary, cornea, heart, kidney, pancreas, liver, spleen, lung, testicle, bladder, and blood vesicles. In one particular embodiment, the organ tissue or organ is an ovary.

According to some embodiments, the stabilized ACC is for use as a supplement to cell culture medium suitable for growth of plant or insect cells.

According to some embodiments, the stabilized ACC is for use as a supplement to cell culture medium suitable to growth of animal, plant or insect cells and being a natural medium selected from biological fluids, tissue extracts and clots; or an artificial medium selected from a balanced salt solution, basal medium and complex medium.

According to some embodiments, the stabilized ACC is for use as a supplement to the cell medium selected from DMEM, RPMI 1640, MEM, IMDM, L-15 Medium (Leibovitz), MCDB Medium, Medium 199, opti-MEM and DMEM/F-12, Schneider's Drosophila medium, Grace's Insect medium, IPL-41 Insect Medium Sf-900, Serum-free Insect Media, Shields and Sang M3 Insect Medium, TC-100 Insect Medium, TNM-FH Insect Medium, Ham's F-12, Ham's F-10, GMEM, Ames' Medium, Basal Medium Eagle (BME), Claycomb, Click's Medium, Glasgow Minimum Essential Medium (GMEM), MegaCell Media, McCoy's 5A Modified Medium, NCTC Medium, Williams' Medium E, Waymouth Medium, TC-10 and IPL-10 medium. According to one embodiment, the stabilized ACC is for use as a supplement to the cell medium selected from Monoculture Media such as Quinn's Advantage™ (SAGE) medium 1-Step™, Sequential Media such as Quinn's Advantage™, Sequential Media (ORIGIO), MEDICULT, universal IVM, DMEM, RPMI 1640, MEM, IMDM, opti-MEM, GMEM, Ham's F-, DMEM/F-12, Schneider's Drosophila medium, Grace's Insect medium, Sf-900, TC-10, IPL-10, B5, N6 and Nitsch's medium. According to some embodiments, the stabilized ACC is for use as a supplement to the cell medium selected from media for sperm, media for sperm or maturation such as ISolate®, PureCeption™, Multipurpose Handling Medium® (MHM®), Quinns™ Sperm Washing Medium, Multipurpose Handling Medium® (MHM®) and Modified HTF Medium with Gentamicin, medium. medium for fertilization, medium for embryo development, and medium for embryo or/and gamete maturation, handling and/or cryopreservation.

According to these embodiments, the ACC for use as a supplement to cell culture medium is capable of enhancing growth cell culture, tissue culture or organ culture when added to cell culture medium.

According to some embodiments, the stabilized ACC is for use as a supplement to cell culture media suitable for growth of unicellular eukaryotes. According to one embodiments, the unicellular eukaryotes are yeasts such as *Saccharomyces*, more particular *Saccharomyces cerevisiae*. According to one embodiment, the stabilized ACC is for use as a supplement to YPD, YPG or YPAD media.

According to some embodiments, the stabilized ACC is for use as a supplement to cell culture medium suitable for growth of prokaryotes, e.g. bacteria. In some embodiments, the bacteria is *E. coli* or probiotic bacteria such bacteria of *Bifidobacterium* and *Lactobacillus* genera. According to one embodiments, the stabilized ACC is for use as a supplement to LB and M9 media.

According to these embodiments, the ACC for use as a supplement to cell culture medium is capable of enhancing growth of said yeast or said bacteria when added to cell culture medium.

According to some embodiments, the stabilized ACC is for use as a supplement to cell culture medium suitable for growth of archaea.

According to some embodiments, the stabilizer is selected from the group consisting of a polyphosphate such as triphosphate, phosphorylated amino acid such as phosphoserine, bisphosphonate, citric acid, and any combination thereof such as combination of triphosphate and citric acid or combination of phosphoserine and citric acid.

According to some embodiments, stabilized ACC for use as a supplement to cell culture medium stays stable in amorphous phase in a dry form for a period of at least 7 days, at least one month, at least 3 months, at least 6 months, or at least one year. In other embodiments, the stabilized ACC stays stable in amorphous phase when dispersed in a cell culture medium for at least one hour, for a period of at least 4, 6, 8, 12 or 24 hours, at least 7 days, or at least one month.

According to any one of the above embodiments, the stabilized ACC for use as a supplement for cell culture medium may be formulated as a solid, liquid or semi-liquid from. According to some embodiments, the stabilized ACC for use of the present invention is formulated in a solid form e.g. powder, tablets, capsules, or granules. In one particular embodiment, the stabilized ACC for use as a supplement is formulated as a powder. According to some embodiments, the stabilized ACC for use as a supplement is formulated as a liquid or semi-liquid form. According to one embodiment, the liquid form is a suspension or emulsion and the semi-liquid form is a gel or viscous suspension such as colloidal suspensions. In one specific embodiment, the stabilized ACC is formulated as a suspension. Therefore in one embodiment, the stabilized ACC for use as a supplement to cell culture medium is added to a cell culture medium either during the preparation of a cell culture medium or prior to use of that media, as a powder or as a suspension. According to one even more specific embodiment, the stabilized ACC is added as a freshly prepared suspension.

According to one embodiment, the average diameter of the stabilized ACC primary particles is about 10 nm to about 5 µm. According to another embodiment, the average diameter of the ACC primary particles is about 30 nm to about 400 nm. According to yet another embodiment, the average diameter of the ACC primary particles is about 30 nm to 350 nm.

According to certain embodiments, the average diameter of the ACC primary particles is about 35 nm to 300 nm, 40 nm to about 250 nm, about 45 nm to about 200 nm, about 50 nm to about 150 nm or about 60 nm to about 100 nm. According to still another embodiment, the primary particles of ACC are aggregated and an average diameter of the aggregates is between 0.5 µm and 300 µm. According to one further embodiment, the diameter of aggregates of the ACC primary particle is about 1 to about 100 µm, about 10 to about 50 µm or about 20 to about 40 µm. According to another embodiment, the average diameter of the aggregates of the ACC primary particle is between 1 μm and 10 μm.

According to any one of the above embodiments, the ACC for use as a supplement to the cell culture medium is added to a cell culture medium at the final concentration of about 0.1 to about 20 mM, about 0.5 to about 15 mM, about 1 to about 10 mM, about 2 to about 8 mM, about 3 mM to about 6 mM or about 4 mM to about 5 mM. In more particular embodiment, the stabilized ACC is present in a concentration of 0.5 to about 4 mM, about 1 to about 3 mM, about 1.5 to about 2.5, or about 1, 1.5, 2 or 2.5 mM According to some more specific embodiments, the present invention provides ACC stabilized by at least one stabilizing agent selected from polyphosphate such as organic polyphosphate, phosphorylated amino acid, bisphosphonate, organic acid and any combination thereof for use as a supplement to a cell culture medium suitable for growth of (i) muscle, nerve or bone cell or tissue cultures, (ii) human or non-human mammal embryos, (iii) stem cells, (iv) gametes, or (v) ovaries. According to some embodiments, the stabilizing agent is a phosphoserine. According to another embodiment, the stabilizing agent is a triphosphate. According to yet another embodiment, the stabilizing agent is a combination of phosphoserine with organic acid, such as citric acid. According to further embodiment, the stabilizing agent is a combination of triphosphate such as sodium triphosphate with organic acid, such as citric acid. According to one embodiment, such cell culture medium is suitable for growth of muscle, nerve or bone cell or tissue culture. According to one embodiment, the stabilized ACC supplementing said cell culture medium is capable of enhancing growth, e.g. proliferation, development, maturation or differentiation of the cells. According to one embodiment, the cells are nerve cells and more particular damaged nerve cells. According to one embodiment, the stabilized ACC for use as a supplement to cell culture medium is capable of enhancing regeneration of damaged nerve cells. According to another embodiment, the cells are muscle cells, in particular dystrophic muscle cells such as Duchenne muscular dystrophic cells. According to one embodiment, the stabilized ACC for use as a supplement to cell culture medium is capable of enhancing myotube formation and and/or the onset of contractility of muscle cells. According to one embodiment, the stabilized ACC for use as a supplement to cell culture medium is capable of enhancing development of human embryos. According to one embodiment, the stabilized ACC for use as a supplement to cell culture medium is capable of enhancing maturation or preservation of gamete, and in particular sperm. According to another embodiment, stabilized ACC for use as a supplement to cell culture medium is capable of enhancing cryopreservation of embryos or gametes, as describe hereinabove. According to one embodiment, the stabilized ACC for use as a supplement to cell culture medium is capable of enhancing sperm motility, enhancing sperm progressive motility, increasing sperm count, and any combination thereof. According to further embodiment, the stabilized ACC for use as a supplement is capable of enhancing the growth, e.g. proliferation, expansion and/or differentiation, of stem cells, and in particular human stem cells. According to some embodiments, the stem cells are selected from embryonic, chorionic, amniotic, hematopoietic, mesenchymal, neural, glial, adult and induced pluripotent stem cells. According to one embodiment, the cell culture medium supplemented with stabilized ACC is capable of enhancing the growth parameters, e.g. proliferation, maturation, development or differentiation of the cells by about 100% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%.

According to some embodiments, the present invention provides stabilized ACC for use as a supplement to cleavage, monoculture or sequential medium wherein the stabilizing agent is phosphoserine or sodium triphosphate, optionally in combination with citric acid, and said stabilized ACC is capable of enhancing development of human embryos.

According to some embodiments, the present invention provides stabilized ACC for use as a supplement to cell culture medium, wherein the agent is phosphoserine, etidronic acid or sodium triphosphate, optionally in combination with citric acid, and said stabilized ACC is capable of enhancing regeneration of nerve cells.

According to some embodiments, the present invention provides stabilized ACC for use as a supplement to DMEM/F12 or DMEM/F12 optionally supplemented with horse serum (HS), L-Glutamine, Gentamycine, and Insulin, wherein the stabilizing agent is selected from phosphoserine, etidronic acid or sodium triphosphate, optionally in combination with citric acid, and said stabilized ACC is capable of enhancing myotube formation and/or the onset of contractility in skeletal muscle cell e.g. in case of Duchenne muscular dystrophy.

According to some embodiments, the present invention provides ACC stabilized by phosphoserine, etidronic acid or sodium triphosphate, optionally in combination with citric acid, for use as a supplement to a cell culture medium, and thereby being capable of enhancing differentiation of stem cells, in particular differentiation of MBA13 to osteoblasts.

According to some embodiments, the present invention provides ACC stabilized by phosphoserine, etidronic acid or sodium triphosphate, optionally in combination with citric acid, for use as a supplement to media for sperm separation, wash or maturation such as ISolate®, PureCeption™, Multipurpose Handling Medium® (MHM®), Quinns™ Sperm Washing Medium, Multipurpose Handling Medium® (MHM®). Modified HTF Medium with Gentamicin, and thereby being capable of enhancing maturation of sperm cells, e.g. enhancing sperm motility, enhancing sperm progressive motility, increasing sperm count, and any combination thereof.

the present invention provides ACC stabilized by phosphoserine, etidronic acid or sodium triphosphate, optionally in combination with citric acid, for use as a supplement to a medium such as DMEM/F12 or DMEM/F12 with 10% fetal bovine serum (FBS), 2 mM glutamine, 25 μg/mL gentamicin and 0.3-0.5% NVR-Gel, thereby enhancing preservation of ovaries.

According to some embodiments, the final concentration of stabilized ACC in the cell culture media is about 0.1 to about 8 mM, about 0.5 to about 6 mM, about 1 to about 5 mM, or about 2 to about 4 mM.

According to yet another aspect, the present invention provides a cell culture medium supplement comprising amorphous calcium carbonate (ACC) stabilized by at least one stabilizing agent.

According to one embodiment, the cell culture medium supplement comprising ACC stabilized the stabilized ACC is added to the medium during the preparation of the medium. According to another embodiment, the supplement is added to the medium prior use.

According to some embodiments, the cell culture medium supplement is a solid supplement. According to other embodiments, the supplement is a liquid or semi-liquid supplement.

According to any one of the above embodiments, the ACC is stabilized by at least one stabilizing agent as defined hereinabove. According to some embodiments, the stabilizer is selected from the group consisting of a polyphosphate such as triphosphate, phosphorylated amino acid such as phosphoserine, bisphosphonate, citric acid, and any combination thereof such as combination of triphosphate and citric acid or combination of phosphoserine and citric acid.

The cell culture medium supplement of the present invention comprising stabilized ACC may be added to any cell culture medium described hereinabove. In one embodiment, the cell culture medium supplement comprising stabilized ACC may be added to a cell culture medium suitable for growing a biological culture, e.g. culture of cell, tissue culture, organ culture or organs. The cells may be eukaryotic or prokaryotic. In particular the cell culture medium refers to medium suitable for growth eukaryotic cell culture, tissue culture or organ. According to some embodiments, the cell culture is suspension or adherent cell culture. In some particular embodiments, the medium may be a complete medium, a basal medium, a basal medium supplemented with cell culture medium supplement, medium with various amounts of serum or chemically defined medium.

According to some embodiments the cell culture medium supplement comprising stabilized ACC is capable of enhancing the growth of cells or tissues. Thus in one embodiment, cell culture medium supplement comprising stabilized ACC is capable of enhancing proliferation, maturation, propagation, regeneration, development and/or differentiation of cells, tissues and organs. According to one embodiment, the supplement is capable of enhancing differentiation of stem cells. According to another embodiment, the supplement is capable of enhancing proliferation of a culture of cells. According to yet another embodiment, supplement is capable of enhancing maturation and/or development of cells or tissues. According to certain embodiments, the supplement is capable of enhancing regeneration of cell. According to some embodiments, the cell are eukaryote cells. According to one embodiments, the eukaryote cells are animal, plant, and insect cells. According to a further embodiment, the culture of animal cells is selected from a cell culture, tissue culture, organ culture, stem cells, gametes, embryos and an organ of human or non-human mammal. According to some embodiments the mammal is human, and the culture of human cells is selected from a human cell, tissue culture, and organ culture. According to other embodiments, the mammal is a non-human mammal. According to some embodiments, the cell culture, either human or non-human mammal cell culture is selected from a cell culture of nerve, muscle, epithelial, bone, adipose, stem cells, gametes, and blood cell. According to one embodiment, the cell culture medium supplemented with stabilized ACC is capable of enhancing the growth parameters, e.g. proliferation, maturation, development or differentiation of the cells by about 10% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%.

According to some embodiments, the cell culture medium supplement comprising stabilized ACC may be added to a the cell culture medium suitable for growth of yeast and said cell culture medium is selected from YPD, YPG and YPAD.

According to some embodiments, the cell culture medium supplement comprising stabilized ACC may be added to a the cell culture medium suitable for growth of prokaryotes, said medium is selected from LB and M9.

According to some embodiments, the cell culture medium supplement comprising stabilized ACC is capable of enhancing the growth of yeast and bacteria.

According to some more specific embodiments, the present invention provides a cell culture medium supplement comprising ACC stabilized by at least one stabilizing agent, wherein the agent is selected from phosphorylated amino acid, polyphosphate, bisphosphonate, organic acid and any combination thereof. According to some embodiments, the supplement is added to a cell culture medium suitable for growth of (i) muscle, nerve or bone cell or tissue cultures, (ii) human or non-human mammal embryos, (iii) stem cells, (iv) gametes, or (v) ovaries. According to some embodiments, the stabilizing agent is a phosphoserine. According to another embodiment, the stabilizing agent is a triphosphate. According to yet another embodiment, the stabilizing agent is a combination of phosphoserine with organic acid, such as citric acid. According to further embodiment, the stabilizing agent is a combination of triphosphate such as sodium triphosphate with organic acid, such as citric acid. According to more particular embodiment, the cell culture medium supplement is capable of enhancing growth, e.g. proliferation, differentiation, development or maturation of the cells. According to one embodiment, such cell culture medium supplement is capable of enhancing regeneration of damaged nerve cells. According to another embodiment, such cell culture medium supplement is capable of enhancing myotube formation and/or promoting the onset of contractility of the myotubes. According to a further embodiment, such cell culture medium supplement is capable of enhancing development of embryos such as human embryos. According to a further embodiment, such cell culture medium supplement is capable of enhancing maturation or preservation of gametes and in particular of sperm. According to one particular embodiment, such cell culture medium supplement is capable of enhancing cryopreservation of embryos or gametes, as describe hereinabove. According to one embodiment, such cell culture medium is suitable for proliferation and differentiation of stem cells. According to some embodiments, the stem cells are selected from embryonic, hematopoietic, mesenchymal, neural, glial, adult and induced pluripotent stem cells. According to another embodiment, such cell culture medium supplement is capable of enhancing differentiation of stem cells. According to one particular embodiment, such cell culture medium supplement is capable of enhancing differentiation of stem cells such as MBA13 to osteoblasts. According to one embodiment, the cell culture medium supplemented with stabilized ACC is capable of enhancing the growth parameters, e.g. proliferation, maturation, development or differentiation of the cells by about 10% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%.

According to some embodiments, the present invention provides a cell culture medium supplement comprising ACC stabilized by at least one stabilizing agent selected from phosphoserine, etidronic acid or sodium triphosphate, optionally in combination with citric acid. According to one embodiment, the supplement is added to cleavage, monoculture or sequential medium therefore enhancing development of human embryos. According to one embodiment, the supplement is added to a media for sperm separation, wash or maturation such as ISolate®, PureCeption™, Multipurpose Handling Medium® (MHM®), Quinns™ Sperm Washing Medium, Multipurpose Handling Medium® (MHM®) or Modified HTF Medium with Gentamicin, therefore enhancing maturation or preservation of gametes and in particular sperm. According to another embodiment, such supplement is added to a cell culture medium suitable for growth of nerve cells, therefore enhancing regeneration of nerve cells. According to a further embodiment, the supplement is added to DMEM/F12 medium or DMEM/F12 medium optionally further supplemented with horse serum (HS), L-Glutamine, Gentamycine, and Insulin, thereby enhancing myotube formation in skeletal muscle cell e.g. in case of Duchenne muscular dystrophy. According to yet another embodiment, the supplement is added to a cell culture medium suitable for growth of stem cell, thereby enhancing differentiation of stem cells, in particular differentiation of MBA13 to osteoblasts. According to other embodiments, the supplement is added to medium such as DMEM/F12 or DMEM/F12 with 10% fetal bovine serum (FBS), 2 mM glutamine, 25 μg/mL gentamicin and 0.3-0.5% NVR-Gel, thereby enhancing preservation of ovaries. According to some embodiments, the final concentration of stabilized ACC in the cell culture media is about 0.1 to about 8 mM, about 0.5 to about 6 mM, about 1 to about 5 mM, or about 2 to about 4 mM.

According to any one of the above embodiments, the term "comprise" has the meaning of "consist", therefore according to such embodiment, the cell culture medium supplement consists of ACC stabilized by at least one stabilizer.

According to a further aspect, the present invention provides amorphous calcium carbonate (ACC) stabilized by at least one stabilizer and formulated as a supplement for cell culture medium.

According to certain aspects, the present invention provides a method for enhancing growth of a biological culture, said method comprises exposing said culture to ACC stabilized by at least one stabilizer. According to one embodiment, the biological culture is selected from eukaryote cells, tissue or organ and prokaryote cells.

According to other embodiments, the method comprises enhancing the growth, e.g. enhancing the proliferation, maturation, propagation, regeneration, differentiation and/or development of the biological culture such as cells, tissues and organs.

According to one embodiment, the culture of cells is selected from animal, plant or insect cell culture. According to another embodiment, the tissue culture is selected form animal, plant or insect tissue culture. According to a further embodiment, the organ culture is selected from animal, plant or insect organ culture. According to some embodiments, the animal is a human or non-human mammal. According to certain embodiments, the non-human mammal is selected from livestock animals such as cattle, pigs, sheep, goats, horses, mules, donkeys, buffalo, or camels; a domestic pet e.g. a cat or dog; a rodent such as a mouse, rat, guinea pig or hamster; a lagomorpha such as a rabbit; and primates such as a monkey (e.g. macaques) or an ape (e.g. chimpanzee).

According to some embodiments, the mammal cell culture, either human or non-human mammal cell culture is selected from a cell culture of a nerve, muscle, epithelial, bone, adipose, stem cells, gametes and blood cell. According to one embodiment, the tissue culture is selected from epithelial, connective, muscular and nervous tissue culture. According to some more particular embodiments, the tissue culture is selected from kidney, hepatic, glandular, brain, bone, ocular and muscle tissue culture. According to some embodiments, the organ tissue or organ is selected from ovary, cornea, heart, kidney, pancreas, liver, spleen, lung, testicle, bladder, and blood vesicles. In one particular embodiment, the organ tissue or organ is an ovary.

According to one embodiment, the present invention provides a method for enhancing growth of muscle cells. According to another embodiments, enhancing growth of muscle cells comprises enhancing myotubes formation. According to some embodiments, the method comprises also reducing the time to the onset of spontaneous contractile activity of said myotubes. The time to the onset of spontaneous contractile activity is defined as a time needed to myoblasts to fuse and start spontaneously contracting. In one embodiment, the myocytes formed from said myoblasts are selected from skeletal myocytes or cardiac myocytes. In more particular embodiment, myocytes are skeletal myocytes. According to some embodiments, the method comprises enhancing myotube formation and/or the onset of contractility in skeletal muscle cell e.g. in case of Duchenne muscular dystrophy.

According to other embodiments, the method comprises enhancing growth of nerve cells. In one embodiment, enhancing growth of nerve cells comprises enhancing and acceleration nerve cells regeneration. Thus in one embodiment, the method comprises enhancing regrowth of axonal and dendritic neuronal fibers, of the peripheral and the central nervous system, and/or sprouting from damaged neuronal fibers.

According to some embodiments, the method comprises enhancing the maturation or preservation of gamete, e.g. enhancing in vitro maturation or preservation of sperm or oocyte. According to some embodiments, the gamete is selected from human gamete of non-human mammalian gamete. According to one embodiment, the gamete is sperm. Thus, in one embodiment, the present invention provides a method of enhancing maturation or ameliorating the quality of sperm said method comprises exposing said culture to ACC stabilized by at least one stabilizer.

According to one embodiments, ameliorating the quality of sperm is selected from the group consisting of enhancing sperm motility, enhancing sperm progressive motility, increasing sperm count, and any combination thereof.

According to some embodiments, increasing sperm count comprises increasing the sperm count in motility or progressive motility procedure. According to one embodiments, the motility or progressive motility procedure is a swim up procedure.

According to any one of the above embodiments, the sperm is a sperm of a human or non-human mammal. According to some embodiments the non-human mammal is selected from the group consisting of livestock animals, domestic pets, rodents, wild animals and primate.

In one embodiment, the livestock animals is selected from cattle, pigs, sheep, goats, horses, mules, asses, buffalo, and camels. In some other embodiments, the domestic pet is a cat or dog, the rodent is rat, mice guinea pig or hamster, the lagomorpha is a rabbit, and the primate is monkey such as macaques or ape embryo such as chimpanzee.

According to another embodiment, the sperm is a sperm of a non-mammal animal. According some embodiments, the non-mammal animal is selected from the group consisting fish, insects and birds.

According to one embodiment, the sperm is human sperm. According to other embodiments, the method comprises enhancing in vitro embryo development.

According to some embodiments, the method comprises enhancing stem cells differentiation and/or proliferation. According to some embodiments, the stem cells are selected from embryonic, chorionic, amniotic, hematopoietic, mesenchymal, neural, glial, adult and induced pluripotent stem cells. According to one embodiment, the method comprises enhancing differentiation of stem cells such as MBA13 to osteoblasts.

According to one embodiment, the cell culture medium supplemented with stabilized ACC is capable of enhancing the growth parameters, e.g. proliferation, maturation, development or differentiation of the cells by about 10% to about 600%, about 20% to about 500%, about 30% to about 400%, about 40% to about 300%, about 50 to about 200, about 60% to about 150% or about 70% to about 100%. According to some embodiments, the growth parameters are enhanced by about 100% to about 500%, about 120% to about 400%, about 150% to about 300%.

According to some embodiments, the culture of cells is a culture of bacteria or yeast, thus according to such embodiments, the method comprises enhancing the growth of yeast or bacteria. In some embodiments, the bacteria is *E. coli* or probiotic bacteria such bacteria of *Bifidobacterium* and *Lactobacillus* genera.

According to any one of the above embodiments, exposing cells to ACC stabilized by at least one stabilizing agent comprising adding said ACC to a cell culture medium. The terms "exposing to" and "contacting with" are used herein interchangeably are refer to placing or transferring cells to a medium comprising the component of interest, such as stabilized ACC or adding the component, e.g. stabilized ACC to a medium in which the cells are grown or cultured. The cell media may be any know media in the art. According to some embodiments, the media as defined hereinabove. According to one embodiment, the cell culture medium is selected from a natural medium and artificial medium. According to some embodiments, the natural medium comprises biological fluid selected from plasma, serum, lymph, human placental cord serum, and amniotic fluid. According to another embodiment, the natural medium comprises tissue extracts such as extract of liver, spleen, tumors, leucocytes and bone marrow, extract of bovine embryo and chick embryos. According to a further embodiment, the natural medium comprises coagulants or plasma clots. According to some embodiments, the medium is an artificial medium supplemented with ACC stabilized by at least one stabilizing agent. According to one embodiment, the artificial medium is a balanced salt solution. Examples of balanced salt solution are PBS, DPBS, HBSS, EBSS Tyrode's T6, WM1, Pool's P1, Quinn's HTF, and Gardner's G1. According to another embodiment, the artificial medium is a basal medium. According to some embodiments, the medium may be further supplemented as well known in the art. According to one embodiment, the medium is supplemented with serum, e.g. fetal bovine serum. According to a further embodiment, the artificial medium is a complex medium.

According to one embodiment, the artificial medium is a serum free medium. According to a further embodiment, the artificial medium is a medium with reduced serum content. According to another embodiment, the artificial medium is a protein-free media.

According to one embodiment, the method comprises adding stabilized ACC to a cell culture medium selected from DMEM, EMEM, RPMI 1640 medium, Basal Medium Eagle (BME), Ham's F-10, Ham's F-12, DMEM/F-12, IMDM, opti-MEM, GMEM, IPL-41 Insect Medium, Schneider's Drosophila medium, Grace's Insect medium, Serum-free Insect Media, Sf-900, TC-10, Shields and Sang M3 Insect Medium, TC-100 Insect Medium, TNM-FH Insect Medium, IPL-10, Monoculture Media such as Quinn's Advantage™ (SAGE) medium 1-Step™ or Sequential Media such as Quinns Quinn's Advantage™ cleavage medium, Murashige and Skoog (MS), B5, N6, Nitsch's medium, NCTC Medium, MegaCell Media, Claycomb, Click's Medium, L-15 Medium, Medium 199, MCDB Media, Ames' Media, BGJb Medium, Click's Medium, CMRL-1066 Medium, McCoy's 5A Modified Medium, NCTC Medium, Swim's S-77 Medium, Waymouth Medium, William's Medium E, in vitro maturation media, Menezo's B2 and B3 media, Behr's Blastocyst Medium, Gardner's G2, universal IVM (ORIGIO) and sequential media for embryo growth. According to one embodiment, the method comprises adding stabilized ACC to a cell culture medium selected from Media for sperm separation, Media for sperm wash and Media for maturation, such as ISolate®, PureCeption™, Multipurpose Handling Medium® (MHM®), Quinns™ Sperm Washing Medium, Multipurpose Handling Medium® (MHM®). Modified HTF Medium with Gentamicin. According to one embodiment, the method comprises adding stabilized ACC to a cell culture medium selected from medium for fertilization, medium for embryo development, or medium for embryo or/and gamete maturation, handling and/or cryopreservation.

In some embodiments the cells are grown as stationary or immobilized cultures on a carrier such as Cytodex 1 or 3, Cytopore 2, polystyrene, gelatin, dextran, polyacrylamide or other substitutes carriers.

According to some embodiments, the cell culture medium is suitable for growth of unicellular eukaryotes. According to one embodiments, the unicellular eukaryotes are yeasts such as *Saccharomyces*, more particular *Saccharomyces cerevisiae*. According to one embodiment, the method comprises adding stabilized ACC to a cell culture medium suitable for growth of unicellular eukaryotes, e.g. *Saccharomyces cerevisiae*, said cell culture medium is selected from yeast extract peptone dextrose (YPD), Yeast extract-peptone-glycerol (YPG) and Yeast extract-peptone-dextrose (YPAD) media.

According some embodiments, the cell culture medium is suitable for growth of prokaryotes, e.g. the bacteria is *E. coli* or probiotic bacteria such bacteria of *Bifidobacterium* and *Lactobacillus* genera. According to one embodiment, the method comprises adding stabilized ACC to a medium is suitable for growth of bacteria such as LB or M9.

According to any one of the above embodiments, the stabilized ACC is added to a cell culture medium to the According to any one of the above embodiments, the final concentration of about 0.1 to about 20 mM, about 0.5 to about 15 mM, about 1 to about 10 mM, about 2 to about 8 mM, about 3 mM to about 6 mM or about 4 mM to about 5 mM. In more particular embodiment, the stabilized ACC is present in a concentration of 0.5 to about 4 mM, about 1 to about 3 mM, about 1.5 to about 2.5, or about 1, 1.5, 2 or 2.5 mM.

According to one embodiment, the ACC is formulated in a form of a solid, liquid or semi-liquid. In one particular embodiment, the stabilized ACC is added in a form of a suspension. In yet another embodiment, the suspension is freshly prepared suspension.

According to any one of the above embodiments, the ACC is stabilized by at least one stabilizing agent defined hereinabove. In certain embodiments, the ACC stabilizing agent is independently at each occurrence, an organic acid; phosphorylated, phosphonated, sulfated or sulfonated organic compound; phosphoric or sulfuric ester of a hydroxyl carboxylic acid; an organoamine compound; an organic compound comprising a hydroxyl; an organophosphorous compound or a salt thereof; phosphorylated amino acids and derivatives thereof, a bisphosphonate; an organophosphate compound; an organophosphonate compound; organic polyphosphate, an inorganic polyphosphate, an inorganic phosphorous acid, an organic compound having multiple functional groups as defined above; an inorganic phosphate and polyphosphate compound; an organic compound having a polyphosphate chain; an organic surfactant; a bio-essential inorganic ion; saccharides and derivatives thereof, proteins, phosphorylated proteins, natural and synthetic biopolymers and derivatives thereof or any combination thereof. According to another embodiment, the stabilizing agent is selected from the group consisting of phosphoserine, adenosine triphosphate, adenosine diphosphate, phytic acid, citric acid, etidronic acid, pyrophosphate, polyphosphate, triphosphate, ethanol, hexamethaphosphate, chitin, and any combination thereof. The compound are as defined hereinabove. According to some embodiments, ACC is stabilized by more than one stabilizing agent, e.g. by 2 or 3 stabilizing agents.

According to some embodiments, the stabilizer is selected from the group consisting of a polyphosphate such as triphosphate, phosphorylated amino acid such as phosphoserine, bisphosphonate, citric acid, and any combination thereof such as combination of triphosphate and citric acid or combination of phosphoserine and citric acid.

According to another aspect, the present invention provides a method of preparation of a cell culture medium comprising amorphous calcium carbonate (ACC) stabilized by at least one stabilizer, said method comprises adding the stabilized ACC to a cell culture medium.

According to certain aspects, the present invention provides a kit comprising amorphous calcium carbonate (ACC) stabilized by at least one stabilizer and instruction for use of said ACC in combination with a cell culture medium. According to one embodiment, the stabilized ACC is ACC for use as a cell culture medium supplement. According to one embodiment, the present invention provides a kit comprising calcium chloride, sodium carbonate, at least one stabilizing agent and instruction for preparing stabilized ACC from said calcium chloride, sodium carbonate, at least one stabilizing agent and instruction for use of said stabilized ACC in combination with a cell culture medium. According to one embodiment, calcium chloride, sodium carbonate, and/or at least one stabilizing agent is present as an aqueous solution.

According another embodiment, the kit comprises cell culture medium supplement comprising ACC stabilized by at least one stabilizer and instructions for use of said supplement in combination with a cell culture medium. According to one embodiment, the cell culture medium supplement consistes of ACC stabilized by at least one stabilizer.

According to any one of the above embodiments, the kit further comprises a cell culture medium, as defined hereinabove. Therefore, in one embodiment, the kit comprises ACC stabilized by at least one stabilizer, a cell culture medium and instructions for use. In other embodiments, the kit comprises culture medium supplement comprising ACC stabilized by at least one stabilizer, medium and instructions for use.

The ACC stabilized by at least one stabilizer and the cell culture medium are as described hereinabove.

According to some embodiments, the stabilizer is selected from the group consisting of a polyphosphate such as triphosphate, phosphorylated amino acid such as phosphoserine, bisphosphonate, citric acid, and any combination thereof such as combination of triphosphate and citric acid or combination of phosphoserine and citric acid.

According to some embodiments, the ACC composition comprises a combination of the stabilizers disclosed above.

According to any one of the above embodiments, the stabilized ACC may be formulated as a solid, liquid or semi-liquid formulation. Thus in one embodiment, the stabilized ACC for use as a supplement of a cell culture medium is formulated as a solid, liquid or semi-liquid. According to some embodiments, the stabilized ACC is formulated in a solid form e.g. powder, tablets, capsules, or granules. Thus in one particular embodiment, the stabilized ACC for use as a supplement to a cell culture is formulated as a powder. According to other embodiments, the stabilized ACC for use as a supplement is formulated as a liquid or semi-liquid. According to one embodiment, the liquid form is a suspension or emulsion and the semi-liquid form is a gel or colloid. In one specific embodiment, the stabilized ACC is formulated as a suspension. Therefore in one embodiment, the stabilized ACC formulated as powder or as a suspension is added to a cell culture medium prior to use of that media. According to one even more specific embodiment, the stabilized ACC is added as a freshly prepared suspension.

The kit of the present invention may further comprise a cell culture medium. The cell culture media are well known in the art and any medium may be used. In some embodiments, the cell culture medium is suitable for growing a biological culture, said culture is selected from a culture of cells, tissue culture, organ culture or organs. The culture of cells may be a culture of eukaryotic or prokaryotic cells. In particular the cell culture medium refers to medium suitable for growth eukaryotic cell culture, tissue culture or organ. In some particular embodiments, the medium may be a complete medium, a basal medium, a basal medium supplemented with cell culture medium supplement, medium with various amounts of serum or chemically defined medium.

According to some embodiments, the cell culture medium is selected from DMEM, RPMI 1640, MEM, IMDM, L-15 Medium (Leibovitz), MCDB Medium, Medium 199, opti-MEM and DMEM/F-12, Schneider's Drosophila medium, Grace's Insect medium, IPL-41 Insect Medium Sf-900, Serum-free Insect Media, Shields and Sang M3 Insect Medium, TC-100 Insect Medium, TNM-FH Insect Medium, Ham's F-12, Ham's F-10, GMEM, Ames' Medium, Basal Medium Eagle (BME), Claycomb, Click's Medium, Glasgow Minimum Essential Medium (GMEM), MegaCell Media, McCoy's 5A Modified Medium, NCTC Medium, Williams' Medium E, Waymouth Medium, TC-10 and IPL-10 medium. In one particular embodiment, the cell culture medium is selected from Monoculture Media such as Quinn's Advantage™ (SAGE) medium 1-Step™, Sequential Media such as Quinn's Advantage™ cleavage medium, MEDICULT, universal IVM, DMEM, RPMI 1640, MEM, IMDM, opti-MEM, GMEM, Ham's F-, DMEM/F-12, Schneider's Drosophila medium, Grace's Insect medium, Sf-900, TC-10, IPL-10, B5, N6, or Nitsch's medium. Further examples of media are media for sperm separation such as ISolate®, PureCeption™, Multipurpose Handling Medium® (MHM®) and media for sperm wash such as Quinns™ Sperm Washing Medium, Multipurpose Handling Medium® (MHM®) and Modified HTF Medium with Gentamicin—HEPES. Other embodiments are the medium is a medium for oocytes maturation such as SAGE™ In-Vitro Maturation Media (IVM) and BO-IVM Oocyte maturation medium According to further embodiment, the cell culture medium is selected from medium for fertilization, medium for embryo development, and medium for embryo or/and gamete maturation, handling and/or cryopreservation.

According to some embodiments, the cell culture medium is suitable for growth of yeasts and said cell culture medium is selected from YPD, YPG and YPAD.

According to some embodiments, the cell culture medium is suitable for growth of prokaryotes, said medium is selected from LB and M9.

According to one embodiment, the present invention provides a kit comprising calcium chloride, sodium carbonate, at least one stabilizing agent and instruction for preparing stabilized ACC and instruction for use of said ACC in combination with a cell culture medium. According to some embodiments, calcium chloride and sodium carbonate are present as water solutions. According to one embodiment, at least one stabilizing agent is present as one or two separate solutions. According to one embodiment, the instructions for preparing ACC comprise instructions for mixing the solution comprising calcium chloride and at least one stabilizer with sodium carbonate solution and further adding a solution comprising at least one stabilizing agent.

According to some embodiments, of the present invention, the terms "capable of enhancing" and "enhances" in some embodiments are used interchangeably In any one of the above embodiments, the term "comprising" includes the meaning of "consisting" and may be substituted by it.

As used herein, the term "about", when referring to a measurable value such as an amount, a temporal duration, and the like, is meant to encompass variations of +/−10%, or +/−5%, +/−1%, or even +/−0.1% from the specified value.

Having now generally described the invention, the same will be more readily understood through reference to the following examples, which are provided by way of illustration and are not intended to be limiting of the present invention.

EXAMPLES

Example 1. Effects of ACC on SC-DRG Co-Cultures

Methods
Culture Medium
The culture medium was composed of: 90% Dulbecco's modified eagle medium-nutrient mixture F-12(DMEM-F12) calcium depleted (medium without calcium ions, (special preparation), 10% heat-inactivated fetal bovine serum (FBS), 6 g/L D-glucose, 2 mM glutamine, 25 µg/mL gentamicin and 0.05 ng/mL insulin-like growth factor 1 (IGF-I) (all purchased from Biological-Industries, Israel).
NVR-Gel as a Substrate for Neuronal Cultivation
Neural and Vascular Reconstruction Gel (NVR-Gel, NVR Labs proprietary) is composed of two main components: high molecular hyaluronic acid (HA, $3\times10^6$ Da, BTG, Israel) and laminin (Sigma). For neuronal cell cultivation, NVR-Gel of 1% was diluted with culture medium to a final concentration of 0.3-0.5%. The gel has the texture of a viscous liquid, it adheres easily and successfully the embedded cells or explants to the plastic or glass substratum, and enabled nerve fiber outgrowth in a 3D pattern.

Preparation of Neuronal Tissue Cultures
All the experiments were carried out and authorized by the local ethics committee recognized by the Israeli authorities for animal experimentation. Stationary organotypic cultures of dorsal root ganglia (DRG) and spinal cord (SC) as well as cultures of dissociated brain cells were prepared from rat fetuses (15 days of gestation, Lewis inbred, Harlan, Israel). Immediately after dissection, the isolated tissues were cut with a Macwain tissue chopper into small slices (of 400 µm thickness). In these studies, two tissue culture strategies were used. In the first method, tissue slices were seeded directly in 12 well-culture plates containing 1 mL culture medium containing 0.3%-0.5% NVR-Gel. In the second method, the tissue slices were further dissociated with a trypsin-EDTA solution for 30 min, and washed with a culture medium. Subsequently, the dissociated cells were added to a suspension of chitosan powder or gastrolith powder (micro carriers, MCs) and incubated in suspension at 37° C. for 4 days. The formed floating cells/MCs aggregates were then collected and seeded in 12 well-culture plates containing 1 mL of culture medium containing 0.3%-0.5% NVR-gel.

$Ca^{2+}$ Supplement Source
$Ca^{2+}$ source (listed below) at final concentration of 1 or 2 mM was added once to the gel at the seeding stage and then to the nutrient medium at each consecutive feeding. Calcium source were as following: ACC-Etidronic Acid (ACC—ET) (fresh suspension); ACC-Phosphoserine (ACC-PS) (fresh suspension); Gastrolith (dissolved with 0.1 M HCl and then neutralized with NaOH 1M); gastrolith powder; CCC—Aqueous suspension of crystalline calcium carbonate (commercial nanoparticles powder); and $CaCl_2$ solution—control.

The cultures were monitored by daily phase contrast microscopic observations starting from 24 hours after setting the cultures onward.

Suspensions of fresh ACC preparations consisted of particles forming a stable suspension. The gastrolith is a natural ACC isolated from crabs, and can be purchased only as a dry powder. In this form, its other characteristic components (such as calcium ions and proteins) are not available to the cells. In order to increase their bioavailability, the gastrolith powder was dissolved in 0.1 M HCl (which mimics the acidity which exists in the stomach) and then neutralized with 1M NaOH.

Immunofluorescent Staining of Neuronal Cultures
After removal of the culture medium, the dorsal root ganglia (DRG) cultures were washed with phosphate buffered salt solution (PBS) and fixed in 4% paraformaldehyde for 15 min, and then washed again with PBS. The fixed cells were permeabilized with 0.1% of Triton X-100 in PBS and then immuno-blocked (to avoid non-specific staining) with a 1% bovine serum albumin (BSA) in PBS for 1 h at room temperature. The specimens were then incubated with rabbit anti-neurofilament antibodies (NF, Novus Biologicals, 1:500) to visualize the neurite outgrowth. The primary antibodies were diluted in 0.1% BSA and 0.05% Tween-20 in PBS (diluents buffer) and incubated with the specimens overnight at 4° C. After rinsing with 0.05% Tween-20 in PBS (wash buffer), the DRG specimens were incubated for 1 h at room temperature with the secondary antibodies Alexa-Fluor-594-conjugated donkey anti-rabbit IgG (Jackson ImmunoResearch, USA, 1:800 in a diluent buffer). Finally, the samples were rinsed again with wash buffer, and mounted with mounting medium (Immco Diagnostic, USA). All of the images were observed with an Olympus IX70 microscope.

Results

The effect of various calcium preparations was examined in SC-DRG co-cultures. In general, the cultures contained 400 micron SC slices with attached or separated slices of DRG. It can be said that all of the examined ACC preparations (ACC-ET, ACC-PS, and gastrolith) enhanced significantly neuronal fiber regeneration in comparison to CCC and the $CaCl_2$. Table 1 shows the portion of explants (out of 6) which exhibited nerve fiber sprouting after 4 days of cultivation in the presence of the various calcium preparations ($Ca^{2+}$ concentration of 2 mM) or in the presence of stabilizers alone (the stabilizer was added at the concentration of 0.05% to each well (from a stock solution of 5%)). It can be seen that the most intensive sprouting was observed in cultures which were exposed to ACC-ET (100% of explants), followed by ACC-PS and Gastrolith (66.6% of explants). The CCC and $CaCl_2$ induced neuronal sprouting only from 50% of the explants, and the stabilizers alone even a lower percentage (0-33%) During the establishment of the cultures (after the first week of cultivation) the regenerated nerve fibers became longer, thicker and ramified, until the formation of neuronal networks, mainly in cultures exposed to the various ACC preparations (FIG. 1).

TABLE 1

The effect of ACC preparations on early nerve fiber sprouting from SC-DRG co-cultures.

| Type of calcium preparation | Cultures with axonal regeneration (%) |
| --- | --- |
| ACC-ET (fresh suspension) | 100 |
| ACC-PS (fresh suspension) | 66.6 |
| Gastrolith | 66.6 |
| CCC (crystalline calcium carbonate) | 50 |
| $CaCl_2$ aqueous solution (control) | 50 |
| ET | 33.3 |
| PS | 0 |

Example 2. Effects of ACC on Brain Cultures

Figure 2:
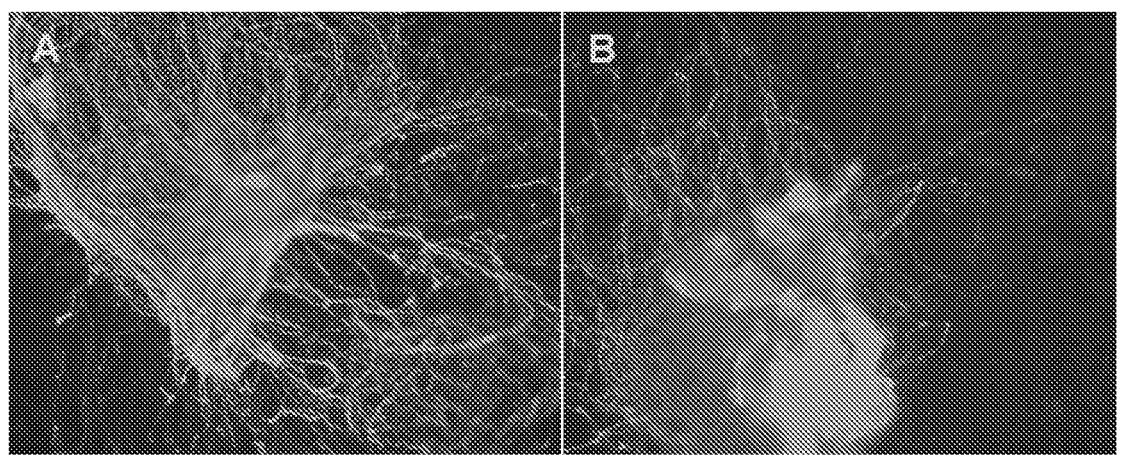
FIG. 2 shows the effect of (A) ACC-stabilized by Etidronic Acid and (B) $CaCl_2$ solution (control) on neuronal sprouting from brain cells cultured on chitosan microcarriers (MCs). Immunofluorescent staining of nerve fibers (anti neurofilament antibody) grown from brain cells-chitosan MCs aggregates, after 30 days in culture in the presence of 2 mM of either ACC-Etidronic Acid or $CaCl_2$) is presented.

The effect of ACC was studied on cultures of brain cells-MCs aggregates seeded in gel after 4 days in suspension (see methods part of Example 1). The results are presented in FIG. 2 and show that the ACC enhanced nerve fibers regeneration, significantly more than the calcium chloride. This is especially notable when comparing the number and the length of nerve fibers between the two treatments.

Example 3—Effects of ACC Preparations on Healthy Skeletal Muscle Cells

Methods

Preparation of Skeletal Muscle Cultures

Stationary skeletal muscle cultures were prepared from healthy 1 day new born rat (Sprague Dawley, Harlan, Israel). The muscle tissue was dissected from posterior legs and was thoroughly minced. Digestion was performed with Trypsin-EDTA while gentle trituration. After 30 min the supernatant, containing dissociated cells, was collected and a fresh Trypsin-EDTA was added. This procedure was repeated two more times. Then, all supernatants were pooled, centrifuged, and the cell pellet was re-suspended in Proliferation Medium. Cells were seeded in a Gelatin coated 12 wells culture plates, $1\times10^5$ cells/well containing 1 mL of Proliferation Medium. Two days later, the medium was changed to Fusion Medium, which was then changed twice a week. The cultures were monitored by daily phase contrast microscopic observations from 24 hours after setting the cultures and onward. At predetermined days, cultures were fixed in methanol for 20 minutes and then stained with Giemsa in order to evaluate the number of myotubes formed with time in cultures.

Culture Plates Coating with Gelatin

Stock solution of 1% porcine gelatin in water, was sterilized by autoclave. Once cooled, 500 µl of the solution were added to each well of the 12-wells culture plat. After incubation for 20 min at room temperature, the excess solution was removed, and the cells were seeded.

Proliferation Medium

For the proliferation stage, cells were cultured in: DMEM/F12 (containing 1 mM $Ca^{2+}$)+10% FBS, 25 µg/mL Gentamycin, and 2 mM L-Glutamine.

Fusion Medium

For the fusion stage the Proliferation Medium was changed with Fusion Medium, which was prepared as following: DMEM/F12 (containing 1 mM Ca2+), 2% horse serum (HS), 2 mM L-Glutamine, 25 µg/mL Gentamycin, and 4 units/100 mL Insulin (all purchased from Biological-Industries, Israel).

List of Tested Calcium Preparations

The fusion medium was enriched with the various calcium preparations listed in Table 2, at $Ca^{2+}$ concentration of 1 mM (since the medium already contained 1 mM of calcium ions, the final concentration of $Ca^{2+}$ was 2 mM). Control cultures were grown without further added calcium, or cultures enriched with free (soluble) stabilizer. The experiment was blinded by marking the various calcium preparations with arbitrary numerals only.

The components were added in one of the following ways: (i) aqueous suspensions of dry material; (ii) aqueous suspension of fresh material (before drying), or (iii) dissolved with HCl (to mimic the acidity which exists in the stomach. After dissolving was accomplished, the formed solutions were neutralized with 1M NaOH).

TABLE 2

List of tested materials

| Added Substance | Total calcium concentration (mM) including 1 mM $Ca^{2+}$ ions of the medium |
| --- | --- |
| ACC-Etidronic Acid (ACC- ET) | 2 |
| ACC-Pyrophosphate (ACC-PyP) | 2 |
| ACC-Phospho serine (ACC-PS) | 2 |
| ACC- Adenosine triphosphate (ACC-ATP) | 2 |
| ACC- Adenosine diphosphate (ACC-ADP) | 2 |
| ACC-Phytic acid | 2 |
| ACC-Citric acid | 2 |
| Crystalline calcium carbonate (CCC) (commercial available powder) | 2 |
| $CaCl_2$ aqueous solution | 2 |
| ET | 1 |
| PyP | 1 |
| PS | 1 |
| ATP | 1 |
| ADP | 1 |
| Phytic acid | 1 |
| Citric acid | 1 |
| Control | 1 |

Results
Effect of Dry ACC on Healthy Skeletal Muscle

Figure 3:
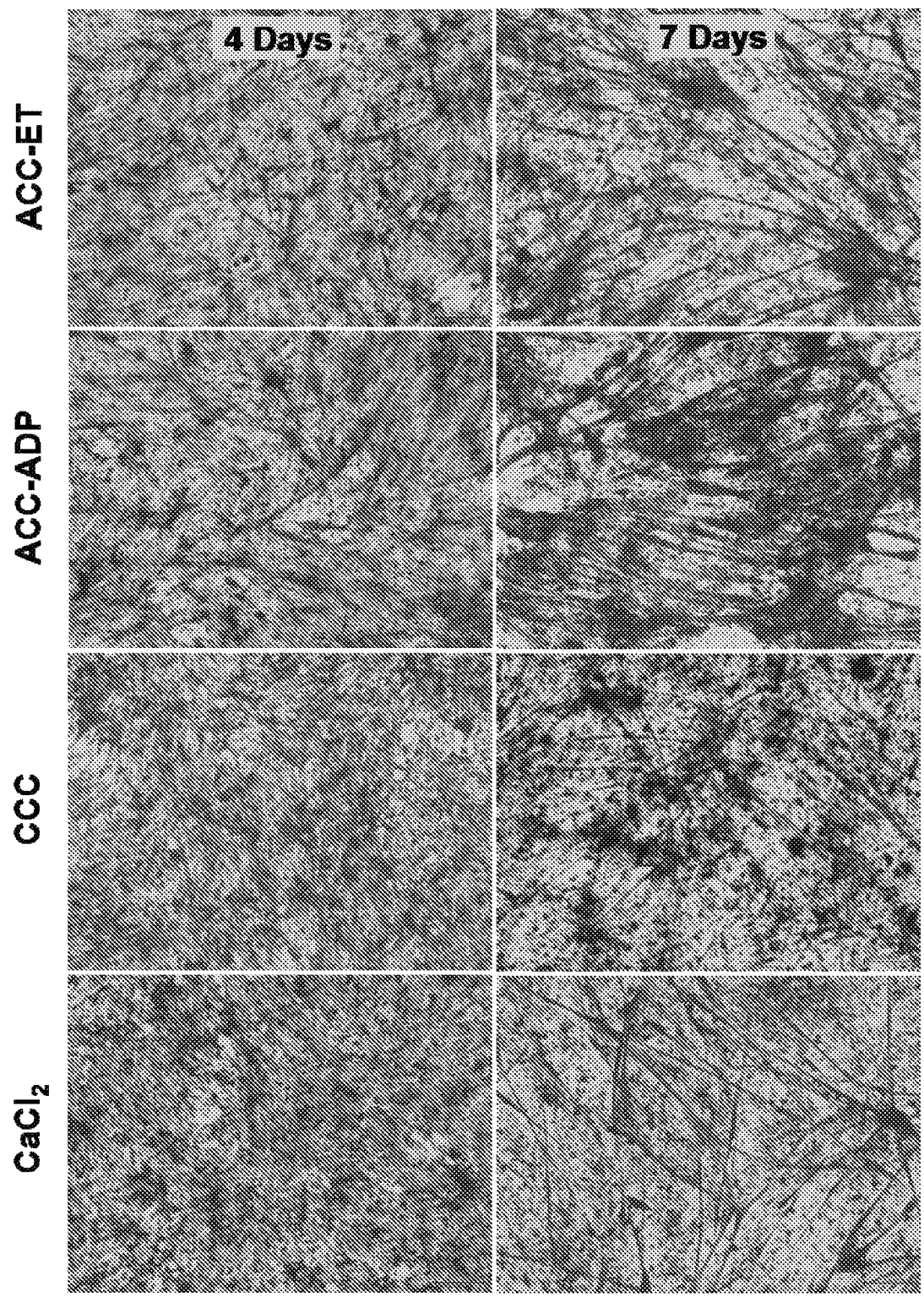
FIG. 3 shows the effect of ACC on formation of myotubes in healthy skeletal muscle cultures. Original magnification ×40. Skeletal muscle cultures were exposed to the following calcium compounds (final $Ca^{2+}$ concentration of 2 mM): ACC-Etidronic Acid; ACC-ADP; Gastrolith; crystalline calcium carbonate (CCC); and $CaCl_2$ solution (control). Cultures were fixed after 4 and 7 days and stained with Giemsa. Enhancement of myotubes formation by skeletal muscle cultures was observed in ACC treated cells.

In the first stage, dry ACC powder was used. The powder (listed in Table 2 according to the stabilizers used in their preparation) were suspended in water, and then added to the culture media in the concentration of 1 mM. Since the medium already contained 1 mM of calcium ions, then the final concentration of $Ca^{2+}$ was 2 mM. The results, some of which are shown in FIG. 3 (left hand side), revealed that cultures which were exposed to ACC exhibited early formation of many myotubes already within 4 days of cultivation, with no significant differences between the different ACC preparations. In control cultures, which were exposed to added CCC or $CaCl_2$, myotubes formation was observed later. After 7 days, the cultures that were treated with ACC exhibited numerous long and thick muscle fibers, while in cultures treated with CCC and $CaCl_2$), fewer, thinner and shorter muscle fibers were developed (FIG. 3; right hand side).

It is also noted, that in cultures exposed to ACC preparations, muscle contractions were observed already on day 7 after seeding, while in cultures exposed to added CCC or $CaCl_2$ muscle contractions appeared only after 10 days or more.

It was concluded from the above in vitro results that all ACC preparations enhance myotubes formation and early muscle contractility of the healthy striated muscle cultures.

Example 4—Evaluating the Effect of ACC on Duchenne Muscular Dystrophy Muscle Cell Line—In Vitro Studies Methods
Mdx Cells Preparation The influence of the different calcium preparations was investigated on the mdx cell line (Duchenne muscular dystrophy model), which was kindly provided by Prof. (Emeritus) David Yaffe from the Weizmann Institute of Science, Israel.

Cells from the Mdx cell line were seeded in a Gelatin coated 12 wells culture plate, $3 \times 10^4$ cells/well containing 1 mL of Proliferation Medium. Two days later (~66% confluence), the medium was changed to Fusion Medium which was changed twice a week. The various calcium preparations were separately added to the Fusion Medium according to the treatment described in Table 3. Cultures were enriched with the various calcium preparations, at $Ca^{2+}$ concentration of 1 mM. Since the medium already contained 1 mM of calcium ions, then the final concentration of Ca2+ was of 2 mM

TABLE 3

Calcium sources

| Treatment | Calcium source (2 mM) |
| --- | --- |
| Control | $CaCl_2$ |
| ACC-ET | Amorphous Calcium Carbonate-Etidronic Acid |
| ACC-PS | Amorphous Calcium Carbonate-Phospho Serine |

The effects of the tested calcium preparations on cell proliferation, fusion to form myotubes and muscle contraction were monitored by daily phase contrast microscopic observation. At predetermined days, cultures were fixed in methanol for 20 minutes and then stained with Giemsa in order to evaluate the number of myotubes formed with time in cultures.

Creatine Kinase (CK) Analysis in Muscle Tissue Culture

In muscle cell cultures, CK is an indicator of myotubes formation and CK level increases (in tissue culture plates) in direct correlation with the progression of myotubes formation in muscle cultures. At predetermined days, cells were collected from culture wells (using a rubber policeman) and kept in 1 mL PBS (without $Ca^{2+}$) at −70° C. until analyzed. For CK measurement cell samples were thawed and physically lysed using a sonicator, to release the CK from muscle myotubes. CK concentration was determined using Creatine Kinase Activity Assay Kit (CK-NAC REAGENT SET, CURTISS, CHEM-INDEX INC, Hialeah, FL, USA).

Results

Figure 4:
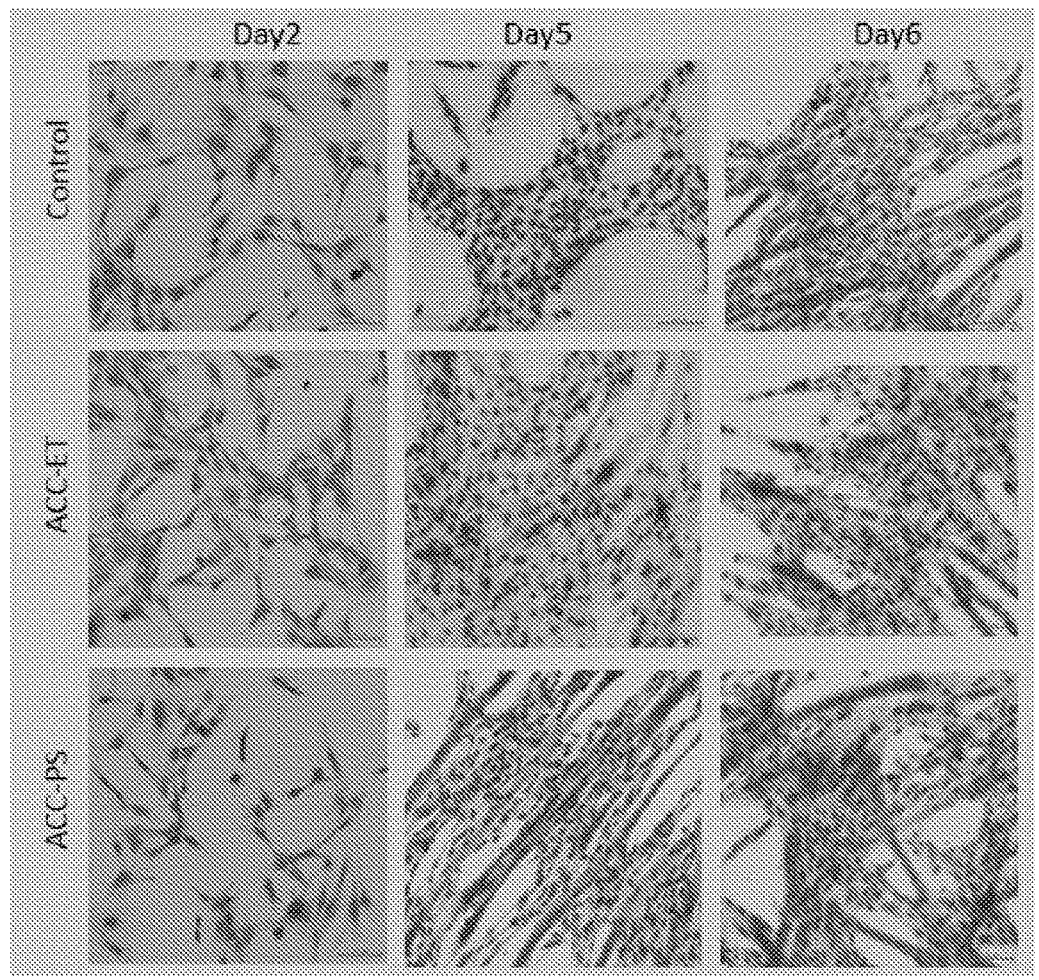
FIG. 4 shows the effect of ACC in the culture medium on early formation of myotubes in mdx cell line cultures. Giemsa staining of the cultures that were exposed to medium containing $CaCl_2$), ACC-ET and ACC-phosphoserine (ACC-PS) is shown. Original magnification ×100.
Figure 5:
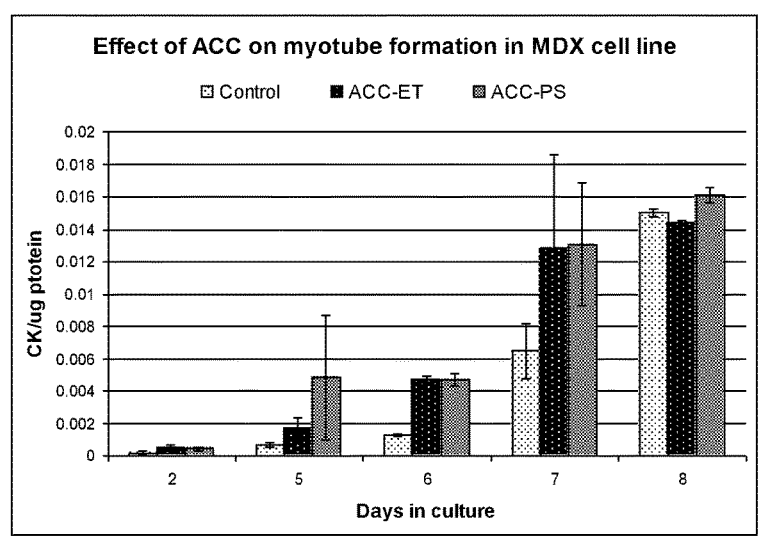
FIG. 5 shows the creatinine kinase (CK) levels as measured in mdx muscle cell line exposed to two ACC preparations (ACC-ET and ACC-PS) versus $CaCl_2$).

The results of the above experiments are presented in FIGS. 4 and 5. As it can be clearly seen, addition of ACC enhanced cell fusion and formation of myotubes better than the addition of a conventional calcium ion source ($CaCl_2$)). This surprising result was demonstrated in both biochemical (CK activity) and morphological (microscopy) analysis (FIGS. 4 and 5). Moreover, the cultures exposed to ACC preparations, muscle contractions were observed already on day 7 after seeding, while in the controls it appeared only after 10 days or more. Therefore, it is concluded that ACC supplementation has a potential to treat DMD patients.

Example 5—The Effect of Calcium Sources on Primary Mdx Mice Cells

Methods
Extraction of Primary Cells

Thigh muscles were removed from the posterior legs of newborn (one day old) mdx mice under sterile conditions, and washed in PBS to remove excess of blood cells. The muscles were minced into small fragments. For enzymatic dissociation, the muscle fragments were placed in a bicker containing trypsin-EDTA solution (0.25 mM). To ensure cell separation, the mixture was placed on a stirrer, at room temperature, at gentle stirring for 20 min. The soup was collected and centrifuged at 300×g for 5 min. The pellet was re-suspended in DMEM containing FBS. The trypsinization steps were repeated for 3 more cycles. All supernatants were combined into one tube. Cell separation was determined visually (using phase contrast microscopy). Cells density was determined by using hemocytometer.

Cells were plated in a 12 wells plate in the concentration of $2 \times 10^5$ cells/well. The medium used was DMEM/F12 W/O $Ca^{2+}$ with the addition of 15% FBS and, 2 mM L-Glutamine Gentamicin (25 µg/ml). Calcium was separately added to the medium according to the treatment as describes in Table 4. At day 2 (~66% confluence) the medium was changed to fusion medium (DMEM/F12 without $Ca^{2+}$ with the addition of 10% HS, Insulin (4 units/100 ml) and Gentamicin (25 µg/ml)). Medium was changed every 3 days.

TABLE 4

Calcium sources used in primary cells study

| Treatment | Calcium source (2 mM) |
| --- | --- |
| Control | $CaCl_2$ |
| ACC-PP | Amorphous Calcium Carbonate stabilized by Polyphosphate |
| ACC-PS | Amorphous Calcium Carbonate stabilized by Phosphoserine |

Cell proliferation and fusion were qualitatively daily monitored. Cultures were fixed at days 2, 3, 4, 5 and 7 and stained with Giemsa, or using Myosin antibody.

Results

Figure 6:
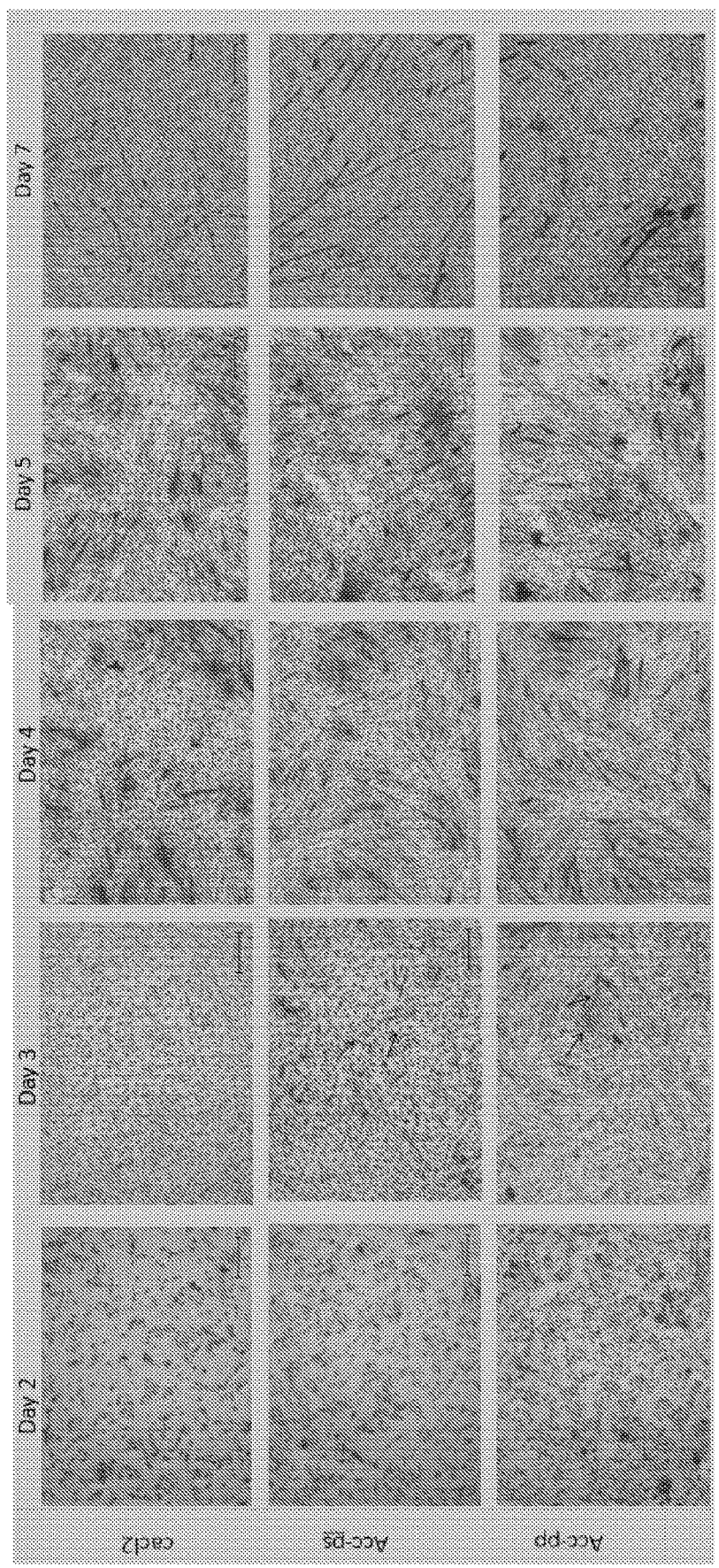
FIG. 6 shows the effect of ACC (ACC-PS, ACC-PP vs. control ($CaCl_2$)) on the formation of myotubes in mdx mice primary cultures (Giemsa staining; original magnification ×50).
Figure 7:
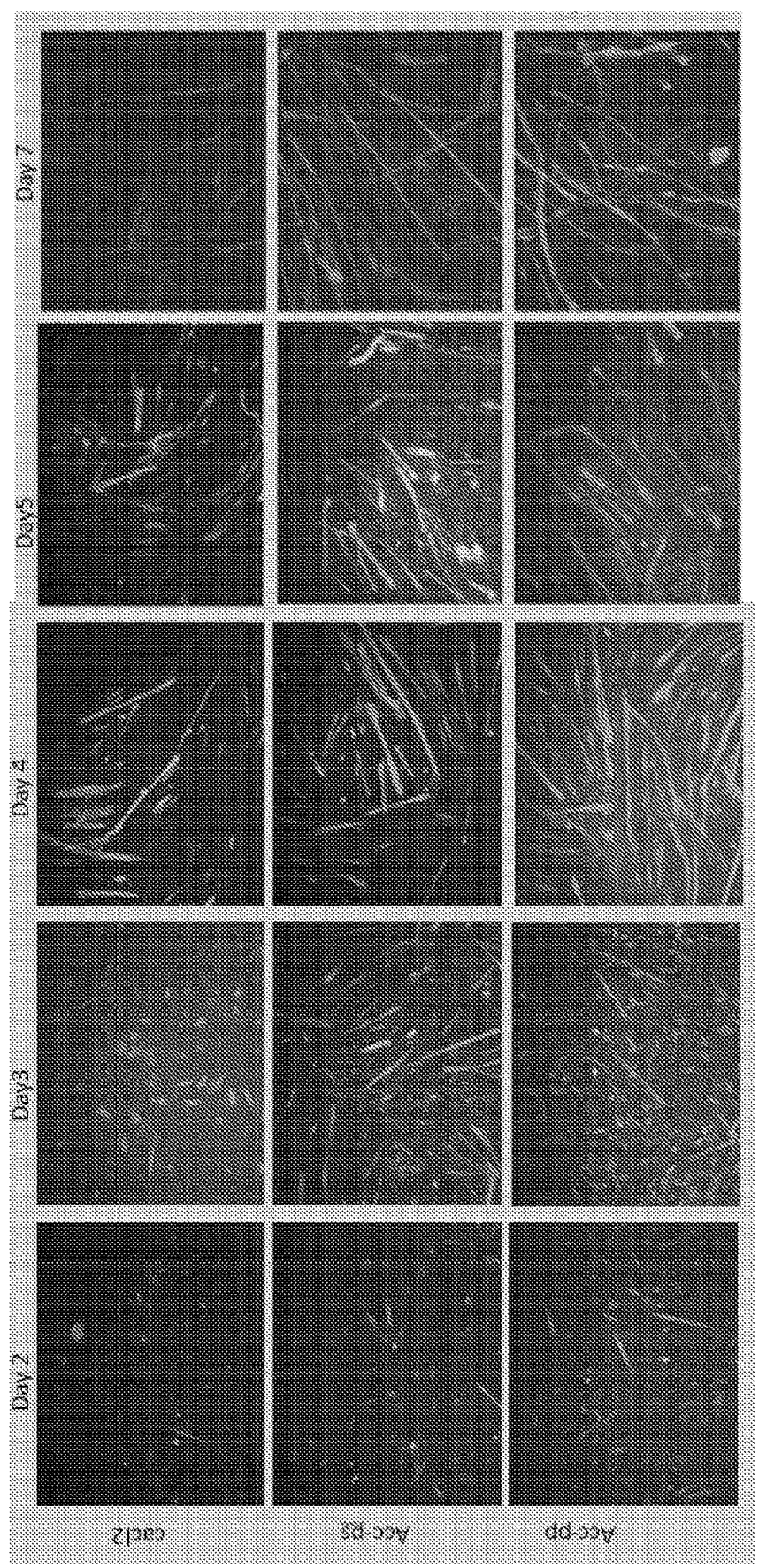
FIG. 7 shows the effect of ACC on formation of myotubes in mdx mice primary cultures demonstrated by myosin immunostaining; control ($CaCl_2$)); ACC-PS, ACC-polyphosphate (ACC-PP). Original magnification ×100.

The results are presented on FIGS. 6 and 7. The beneficial effect of ACC formulations was demonstrated by myotubes formation, specifically at early time points, days 3 and 4 compared to control. Differences in the formed myotubes became indistinguishable at days 5 and 7. There was a high correlation between the Giemsa staining and the staining for myosin.

Enhancement of Embryonic Development in ACC Supplemented Media

Example 6

Materials and Methods:

CBA male mice were bred with BL C57 female mice. The mice were kept on a 12 hours photoperiod schedule with unlimited water and food supply. About 6 to 8 weeks after receiving offspring, each female mouse was injected IP with 5IU of pregnant mare serum gonadotropin (PMSG).

After 48 hours each female mouse was injected IP with 5IU human chorionic gonadotropin (hCG). Male mice proven to be fertile were then put together with the superovulated females. The next morning the female mice were examined for the presence of copulatory plugs. Females that had copulatory plugs were euthanized after 24 hours (approximately 36 hours post-coitus) and embryos at 2 cell stage were retrieved from the oviducts as following: the oviducts were dissected in Quinn's Advantage cleavage media (SAGE, Origio, Denmark) and the embryos were transferred to 20 µL drops with Quinn's Advantage cleavage media (SAGE, Origio, Denmark) overlaid with mineral oil and cultured at 37.0° C. under 5% $CO_2$ and atmospheric oxygen. The collected embryos continued to grow, i.e. in-vitro culture (IVC), until blastocyst/hatching stage. To test the effect of amorphous calcium carbonate, the Quinn's Advantage cleavage media ("cleavage media" hereinafter) was supplemented with different additives, i.e. amorphous calcium carbonate stabilized by polyphosphate (ACC-PP), crystalline calcium carbonate (CCC), polyphosphate (PP), phosphoserine (PS) or sodium carbonate ($NaCO_3$). All supplements were added as a freshly prepared suspension; the preparation of the ACC supplements were performed under aseptic conditions. Untreated cleavage media (without addition of any additive) was used as a control (identified as Cont Q). The embryos were evaluated every day by microscope observation for a detection of the following stages: 2 cells, compactions stage, blastocysts formation and hatching stage. The fraction (in percent) of the embryos reached each stage was calculated (the number of 2 cells embryos was set as 100%).

Results

Embryos development in the cleavage media supplemented with 1.7 mM of amorphous calcium carbonate stabilized with PP (ACC-PP) was compared to a control (Cont Q—development in untreated media). The number of embryos at each developmental stage and their portion of the initial number of embryos (the latter is presented in parentheses) are presented in Table 5.

TABLE 5

Comparison between the embryos grown in the untreated cleavage media and media supplemented with ACC-PP

|  | 2 Cell/d1 | Comp/d2 | Blast/d3 | Hatch/d4 |
|---|---|---|---|---|
| Cont Q | 12 | 2 (16.6) | 10 (83.3) | 8 (66.6) |
| ACC-PP | 40 | 17 (42.5) | 40 (100) | 32 (80) |

Example 7

Embryo development in the cleavage media supplemented with 1.7 mM of either ACC-PP or calcium chloride ($CaCl_2$)) was tested in two separate tests (A and B). In Test A the embryos were grown until the blastocyst stage and in Test B, until the hatching stage. The number of embryos at each developmental stage and their portion of the initial number of embryos (in parentheses) are presented in Table 6 (Test A) or Table 7 (Test B).

TABLE 6

Test A: comparison between embryos grown in cleavage media supplemented with 1.7 mM of either $CaCl_2$ or ACC-PP

|  | 2 Cell/d1 | Comp/d2 | Blast/d3 |
|---|---|---|---|
| $CaCl_2$ | 25 | 16 (64) | 16 (64) |
| ACC-PP | 26 | 24 (92.3) | 22 (84.6) |

TABLE 7

Test B: comparison between embryos grown in cleavage media supplemented with 1.7 mM of either $CaCl_2$ or ACC-PP

|  | 2 Cell/d1 | Comp/d2 | Blast/d3 | Hatch/d4 |
|---|---|---|---|---|
| $CaCl_2$ | 27 | 20 (70) | 20 (74) | 11 (40.7) |
| ACC | 23 | 23 (100) | 23 (100) | 23 (100) |

Example 8

Embryo development in the cleavage media supplemented with 1.7 mM $CaCl_2$), 1.7 mM ACC-PP or 0.85 mM ACC-PP (half of the initial concentration of ACC-PP, identified as ACC-PP0.85). The number of embryos at each developmental stage and their portion of the initial number of embryos (in parentheses) are presented in Table 8.

TABLE 8

Comparison between embryos grown in cleavage media supplemented with 1.7 mM $CaCl_2$, 1.7 mM or 0.85 mM ACC-PP.

|  | 2 Cell/d1 | Comp/d2 | Blast/d3 | Hatch/d4 |
|---|---|---|---|---|
| $CaCl_2$ | 10 | 3 (30) | 8 (80) | 3 (30) |
| ACC | 11 | 7 (63.6) | 9 (81.8) | 7 (63.6) |
| ACC-PP0.85 | 11 | 8 (72.7) | 9 (81.8) | 8 (72.7) |

Example 9

Embryos development in the cleavage media supplemented with 1.7 mM $CaCl_2$), 1.7 mM or 0.85 mM ACC-PP (ACC-PP0.85) were tested and compared to the development in the untreated media. The number of embryos at each developmental stage and their portion of the initial number of embryos (in parentheses) are presented in Table 9.

TABLE 9

Comparison between embryos grown in the untreated cleavage media and media supplemented with 1.7 mM $CaCl_2$, 1.7 mM or 0.85 mM ACC-PP.

|  | 2 Cell/d1 | Comp/d2 | Blast/d3 | Hatch/d4 |
|---|---|---|---|---|
| Cont Q | 42 | 30 (71.4) | 38 (90.4) | 15 (35.7) |
| $CaCl_2$ | 30 | 16 (53.3) | 24 (80) | 13 (43.3) |
| ACC-PP | 30 | 23 (76.6) | 27 (90) | 12 (40) |
| ACC-PP0.85 | 30 | 21 (70) | 30 (100) | 24 (80) |

Example 10

In this experiment 4 female mice aged 5 months old were euthanized. The embryos from each mouse were collected as described in materials and methods, however the embryos were not pooled together the embryos from each oviduct of each mice were either grown in the cleavage media supplemented with 1.7 mM $CaCl_2$) or 1.7 mM ACC-PP grown separately in the culture. This way we could also evaluate the differences between the mice since the embryos from each female were siblings. The number of embryos at each developmental stage and their portion of the initial number of embryos (in parentheses) are presented in Table 10.

TABLE 10

Comparison between embryos from 4 female mice grown separately in cleavage media supplemented with 1.7 mM of either $CaCl_2$ or ACC-PP.

| Mouse # | $CaCl_2$ Total embr. | ACC-PP Total embr. | $CaCl_2$ 2Cell/d1 | $CaCl_2$ irreg/d1 | ACC-PP 2Cell/d1 | ACC-PP irreg/d1 | $CaCl_2$ 8Cell/d2 | $CaCl_2$ comp/d2 | ACC-PP 8Cell/d2 | ACC-PP comp/d2 | $CaCl_2$ Blast/d3 | ACC-PP Blast/d3 | $CaCl_2$ Hatch/d4 | ACC-PP Hatch/d4 |
|---|---|---|---|---|---|---|---|---|---|---|---|---|---|---|
| 1 | 12 | 11 | 3 | 9 | 3 | 8 | 2 | 1 | 0 | 3 | 1 (8.3) | 3 (27.3) | 0 (0) | 2 (18.2) |
| 2 | 9 | 13 | 3 | 6 | 4 | 9 | 0 | 3 | 0 | 5 | 2 (22.2) | 5 (38.5) | 0 (0) | 4 (30.8) |
| 3 | 10 | 10 | 7 | 3 | 3 | 7 | 0 | 6 | 0 | 4 | 5 (50) | 4 (40) | 3 (30) | 3 (30) |
| 4 | 18 | 17 | 14 | 4 | 13 | 4 | 4 | 10 | 2 | 12 | 12 (66.7) | 14 (82.3) | 7 (41.2) | 12 (70.6) |

Example 11

In this experiment, 7 female mice aged 6 months old were euthanized. From each mouse the embryos were collected as described in materials and methods, however from mouse no. 1 and 2 the embryos were not pooled together but rather grown separately, as in Example 5. The embryos from mouse no. 1 were either grown in untreated cleavage media or medium supplemented with 2.6 mM ACC-PP (ACC-PP2.6). The embryos from mouse no. 2 were grown in the cleavage media supplemented with 1.3 mM or 0.6 mM of ACC-PP (identified as ACC-PP 1.3 and ACC-PP0.6, respectively). Embryos from mice no. 3-7 all were pooled together and grown with 1.6 mM of polyphosphate (PP). In addition, the diameters and volumes of the blastocysts were calculated. The number of embryos at each developmental stage and their portion of the initial number of embryos (in parentheses) are presented in Table 11.

TABLE 11

Comparison between sibling embryos grown in untreated cleavage media or media supplemented with ACC-PP at different concentrations. The pooled embryos from mice No. 3-7 were grown in the media supplemented with polyphosphate.

|  | Mouse 1 | | Mouse 2 | | |
|---|---|---|---|---|---|
| Additive | Cont Q | ACC-PP2.6 | ACC-PP1.3 | ACC-PP0.6 | Mice 3-7 PP |
| Total # | 17 | 19 | 18 | 13 | 37 |
| 8 cell/d2 | 7 | 3 | 7 | 4 | 9 |
| comp/d2 | 10 | 16 | 11 | 8 | 20 |
| Blast/d3 | 17 (100) | 19 (100) | 18 (100) | 13 (100) | 20 (54.1) |
| Hatch/d4 | 11 (64.7) | 19 (100) | 17 (94.4) | 6 (46.2) | 17 (45.9) |

It was found that the hatched blastocysts that were grown with 2.6 mM of ACC-PP had 28% bigger diameter and 2 times bigger volume than the control.

Example 12

In this experiment, 7 female mice aged 6 months old were euthanized. The embryos from each mouse were collected as described in materials and methods (Example 6). The embryos were pooled together and divided into 5 groups that were grown in the untreated cleavage medium (Cont Q), or in the medium supplemented with 2.6 mM, 1.3 mM, 0.6 mM ACC-PP (identified as ACC-PP2.6, ACC-PP1.3 and ACC-PP0.6, respectively), or 1.6 mM of polyphosphate (PP). The number of embryos at each developmental stage and their portion of the initial number of embryos (in parentheses) are presented in Table 12.

TABLE 12

Comparison between the embryos grown in the untreated cleavage media or media supplemented with 2.6 mM, 1.3 mM or 0.6 mM ACC-PP or with 1.6 mM PP.

|  | Cont Q | ACC-PP2.6 | ACC-PP1.3 | ACC-PP0.6 | PP |
|---|---|---|---|---|---|
| Total # | 42 | 20 | 31 | 21 | 36 |
| 8 cell/d2 | 19 | 5 | 7 | 5 | 6 |
| comp/d2 | 25 | 15 | 24 | 16 | 30 |
| Blast/d3 | 35 (83.33) | 20 (100) | 26 (83.87) | 3 (14.28) | 34 (94.44) |
| Hatch/d4 | 16 (38.09) | 19 (95) | 15 (48.38) | 18 (85.7) | 16 (44.44) |

Example 13

In this experiment, 6 female mice aged 6 months old were euthanized. The embryos from each mouse were collected as described in materials and methods. The embryos were pooled together and were divided into 3 groups: one served as control (Cont Q), and in two other groups the embryos were grown in the cleavage media supplemented with 3.3 mM of ACC-PP (ACC-PP3.3) or with 3.3 mM of commercially available nanometric crystalline calcium carbonate (CCC). All the three media were prepared under aseptic conditions. The number of embryos at each developmental stage and their portion of the initial number of embryos (in parentheses) are presented in Table 13.

TABLE 13

Comparison between the embryos grown in the untreated cleavage media or media supplemented 3.3 mM ACC-PP or 3.3 mM CCC.

|  | Cont Q | ACC-PP 3.3 | CCC |
|---|---|---|---|
| Total # | 18 | 45 | 17 |
| 8 cell/d2 | 10 | 0 | 3 |
| comp/d2 | 8 | 45 | 14 |
| Blast/d3 | 18 (100) | 45 (100) | 17 (100) |
| Hatch/d4 | 14 (77.7) | 42 (93.3) | 14 (82.35) |

Example 14

In this experiment, 6 female mice aged 7 months old were euthanized. From each mouse the embryos were collected as described in materials and methods (Example 6). The embryos were pooled together and were grown in the cleavage media supplemented with 1.7 mM $CaCl_2$), 1.7 mM ACC-PP, 0.8 mM of ACC-PP (ACC-PP0.8) or 1.7 mM of phosphoserine (PS). The number of embryos at each developmental stage and their portion of the initial number of embryos (in parentheses) are presented in Table 14.

TABLE 14

Comparison between the embryos grown in the cleavage medium supplemented with 1.7 mM $CaCl_2$, 1.7 mM, 0.8 mM ACC-PP or 1.7 mM of PS.

|  | $CaCl_2$ | ACC-PP | ACC-PP 0.8 | PS |
|---|---|---|---|---|
| Total # | 11 | 15 | 14 | 13 |
| 8 cell/d2 | 6 | 1 | 3 | 5 |
| comp/d2 | 5 | 14 | 11 | 8 |
| Blast/d3 | 10 (90.90) | 14 (93.3) | 14 (100) | 12 (92.3) |
| Hatch/d4 | 4 (36.36) | 13 (86.6) | 11 (78.57) | 10 (76.9) |

It can be seen that in that particular experiment adding calcium chloride had a negative effect on embryonic development resulting in a lower percentages of blastocysts and hatched blastocysts.

Example 15

In this experiment 6 female mice aged 6 months old were euthanized. The embryos from each mouse were collected as described in materials and methods (Example 6), however the embryos from mouse no. 1 and 2 were not pooled together but rather grown separately as a sibling experiment (see Example 10). The embryos from female no. 1 were grown in the untreated cleavage media or in the media supplemented with 1.7 mM nanometric crystalline calcium carbonate (CCC). The embryos from mouse no. 2 were grown in the media supplemented with 1.7 mM ACC-PP or with 1.7 mM of sodium carbonate ($NaCO_3$). All the embryos from mice no. 3-6 were pooled together and grown in the untreated media or media supplemented with 1.7 mM $NaCO_3$ or 1.7 mM ACC-PP. In addition, the diameter and volume of the blastocysts were calculated (see Table 15).

TABLE 15

A development assessment of sibling embryos taken from two mice and of pooled embryos grown in differently supplemented cleavage media.

|  | Mouse 1 | | | Mouse 2 | | Mice 3-6 | |
|---|---|---|---|---|---|---|---|
| Additive | Cont Q | CCC | ACC-PP | $NaCO_3$ | Cont Q | $NaCO_3$ | ACC-PP |
| Total # | 20 | 24 | 12 | 16 | 20 | 10 | 19 |
| 8 cell/d2 | 14 | 14 | 3 | 6 | 14 | 2 | 17 |
| comp/d2 | 6 | 6 | 8 | 8 | 6 | 7 | 8 |
| degenerative | 0 | 1 | 1 | 2 | 0 | 1 | 0 |
| early Blast/d3 | 11 | 8 | 2 | 14 | 12 | 0 | 2 |
| Blast/d3 | 9 | 12 | 9 | 2 | 8 | 0 | 17 |
| Blast/d4 | 6 | 5 | 0 | 0 | 6 | 0 | 0 |
| Hatch/d4 | 14 (70) | 15 (62.5) | 11 (91.6) | 2 (12.5) | 14 (70) | 0 (0) | 19 (100) |

It can be seen that adding sodium carbonate resulted with very poor embryonic development compared to control or to the addition of ACC-PP. It was also found that the hutched embryos that were grown in the cleavage media substituted with 2.6 mM of ACC-PP had a 28% bigger diameter and ×2 times a bigger volume than the control.

Example 16. Preparation of 10% TP-1% Citric Acid ACC (ACC Stabilized with 10% Triphosphate and 1% Citric Acid) Formulated as Cell Culture Medium Supplement 36 ml of 3% Calcium chloride solution were mixed with 4 ml of 0.27% Citric Acid solution and with 10 ml of 0.5406% Triphosphate solution. Then 40 ml of 1.9485% Sodium carbonate solution was added to precipitate ACC. 10 ml of the stabilizing solution containing 0.5406% triphosphate was added to the ACC suspension creating stabilized ACC suspension. The obtained suspension was used as a supplement to Quinn's™ cleavage medium or to Quinn's™ 1-Step medium. The suspension was added to the final concentration of ACC of 1.7 or 3.4 mM. Alternatively, the suspension is filtered using a Buchner funnel, the cake is washed with water and the cake is further dried, e.g. in the oven. The powder is added to the cleavage medium to the final concentration of 1.7 or 3.4 mM.

Example 17

In this experiment 4 female mice aged 6-8 weeks old were euthanized. The embryos from each mouse were collected as described in materials and methods. The stabilized ACC (ACC stabilized with 10% triphosphate and 1% citric acid) was prepared as described in Example 16. The embryos from each female were separated and were grown one part in the untreated SAGE 1-Step™ medium and the second part in the SAGE 1-Step™ medium supplemented with 1.7 mM ACC-PP or 3.4 mM ACC-PP. As can be seen from FIG. 8 addition of stabilized ACC had a positive effect on the embryonic development resulting in a higher percentages of blastocysts and hatched blastocysts especially with the 3.4 mM ACC. It has been surprisingly found that embryos that were grown in cleavage medium supplemented with stabilized ACC showed a rapid cleavage and higher hatching rate.

Example 18. Preparation of ACC Formulated as Cell Culture Medium Supplement

Compositions of ACC stabilized by different stabilizers (triphosphate (TP), hexametaphosphate (HMP), pyrophosphate (Pyr), phosphoserine (PS), Etidronic acid (ET), Zoledronic acid (ZA); or Medronic acid (MA) were prepared) were prepared. In a typical procedure, a calcium solutions (300 ml of water, 24 g of calcium chloride and a stabilizer) and a carbonate solution (200 ml of water and 17.3 g of sodium carbonate) were mixed together to precipitate ACC. A stabilizer solution (100 ml of water and stabilizer; the content of the stabilizers in the calcium and stabilizer solution is presented in Table 16) was added to the ACC suspension creating stabilized ACC suspension. The suspension may be used as a supplement. The ACC was then filtered using a Buchner funnel, and the cake was washed with water. The suspension was dried to obtain a powder. The powder may be added as a cell culture medium supplement or resuspended in an aqueous medium and added as a suspension.

On day 2, when more than 80% cell confluence was achieved (~48 h) the medium was changed to MSCgo rapid osteogenic medium (cat #05-442-1B) containing factors that promote osteoblastic differentiation. Following medium change, rows A-C were supplemented with additional 1 mM calcium (total 2.488 mM calcium) originated from Amorphous Calcium Carbonate (ACC) stabilized by 10% Triphosphate+1% citric acid; rows D-F were supplemented with additional 1 mM calcium (total 2.488 mM calcium) originated from calcium chloride; Row G in the plate was treated with MSCgo medium (total 1.488 mM calcium). Row H of the plate was treated with MSC NutriStem® XF nutrient basal medium+ supplement mix (total 1.488 mM calcium).

On day 4, medium was exchanged with fresh preparations of ACC.

In parallel, a control plate was also seeded with MDX cell lines originated from damaged muscles of MDX mice. The staining of these cell was used to set the background staining of cells intrinsic calcium and also to eliminate the possibility that calcium deposition of the ACC treatment is stained. Prior seeding, wells were coated with gelatin, which is used as a standard substrate for MDX cells attachment. MDX Cells were seeded on a 24 well plate in a concentration of $3\times10^4$ cells/well. Seeding day is defined as "Day 0".

TABLE 16

The content of the stabilizers in different ACC composition

| | | | | | Composition | | | |
|---|---|---|---|---|---|---|---|---|
| Stabilizer in: | 1% TP | 2% TP/ HMP/Pyr | 3% TP/ HMP/Pyr | 4% TP/ HMP/Pyr | 5% TP/ HMP/Pyr/ PS/ET/ ZA/MA | 6% TP/ HMP/Pyr/ PS/ | 10% TP/ HMP/Pyr/ PS/ET/ ZA/MA | 15% TP/ HMP/Pyr/ PS |
| Calcium solution (g) | 0.12 | 0.24 | 0.36 | 0.48 | 0.6 | 0.72 | 1.2 | 1.8 |
| Stabilizing solution (g) | 0.12 | 0.24 | 0.36 | 0.48 | 0.6 | 0.72 | 1.2 | 1.8 |

In other examples the compositions were prepared as described above, with addition of citric acid to calcium solutions so as to obtain 1% citric acid in the final composition. The suspension is used per se as a culture medium supplement. Alternatively, the suspension was further washed with water and dried so as to obtain a powder. The powder may be added to any cell culture medium or be resuspended in aqueous medium.

Example 19. Growth of MBA13 Stem Cells (Bone Marrow Stromal Cells) to Osteoblasts Material and Methods Two days following thawing, MBA-13 cells (received from Prof. Dov Zipori, Weizmann Institute of Science) were re-suspended in recombinant trypsin solution and seeded on a 96 wells plate, (Day "0") in a concentration of $1\times10^4$ cells/well using MSC Nutristem® XF basal medium (Biological Industries, cat #05-200-1A) supplemented with Mesenchymal stem cells (MSC) supplement mix medium (Biological Industries cat #05-201-06) in a ratio of 50 ml:300 μl. Rows A-H of columns 1-4 of the 96 plate were pre-coated with MCS attachment solution diluted in PBS (without $Ca^{2+}$, $Mg^{2+}$), in a ratio of 1:100 for cells seeding. Rows A-H of Columns 5-8 of the 96 plate were pre-coated with Gelatin 0.1% for 30 minutes at room temperature.

On day 2, the medium in the wells was replaced with the following:

Columns 1 and 2 were treated with Spinal Cord (SC) medium that is prepared in-house (the medium comprises 0.6 wt % D-glucose, 2 mM L-glutamine, Gentamicin 25 μg/ml, B27, N2, BSA 0.1 mg/ml, Hepes, 10% FBS, DMEM/F12 and IGF-I, 50 ng/ml)+1 mM calcium originated from ACC (total calcium concentration of 2 mM); columns 3 and 4 were treated with SC medium+1 mM originated from $CaCl_2$; Columns 5 and 6 were treated with SC medium. Both types of cells (MBA13 and MDX) were cultured up to 10 days.

Fixation (with 4% Paraformaldehyde for 20 minutes) of few wells from each type was performed on the 5th, 7th and 10th day following medium exchange, that are Days 7, 9 and 12 of the study.

Once the cells were fixated, two types of staining reagents were used to stain extracellular calcium or bone deposition in order to estimate osteoblasts functionality: (i) Alizarin red (Sigma A55333) and (ii) Alkaline Phosphatase (DAKO BCIP/NBT substrate system K0598) as following:

Alizarin red staining procedure—pH was adjusted to 4.2. Cells were washed twice with PBS and fixed with cold methanol for 5 minutes and then washed again with PBS. Alizarin solution in a concentration of 2% was used for 15-20 minutes. Following staining incubation, the samples were washed with water 2-3 times to remove unspecific staining.

Alkaline Phosphatase staining—cells were washed 1 or 2 times with PBS and then fixed with 4% paraformaldehyde for 20 min. Then, washed 3 times with PBS and following removal of PBS remnants, 3 drops of BCIP/NBT kit solution was used to cover the cells including one empty well without any cells as control to quantify the assay. Incubation of the Alkaline phosphatase kit was performed for 1 hour and then rinsed with distilled water.

Results

The results of cells that were cultured for 10 days and stained by both Alizarin and Alkaline phosphatase are provided. Observation performed prior to 10 days hardly detected any calcium deposition in both staining methods.

Cells condition was observed under a light microscope (without fixation) at two time points, days 2 and 4. On both observations, cells that were seeded on wells pre-coated with MSC attachment solution were not in a good condition; the cells became rounded. In contrast, cells that were seeded on wells pre-coated with gelatin were in a good condition. Nevertheless, it was decided to continue with both types of pre-coating. The following results and staining procedures refers to cells grown in Gelatin that was used as attachment substrate.

In Alizarin Red staining, calcium deposits are detected by an orange red color.

Figure 9:
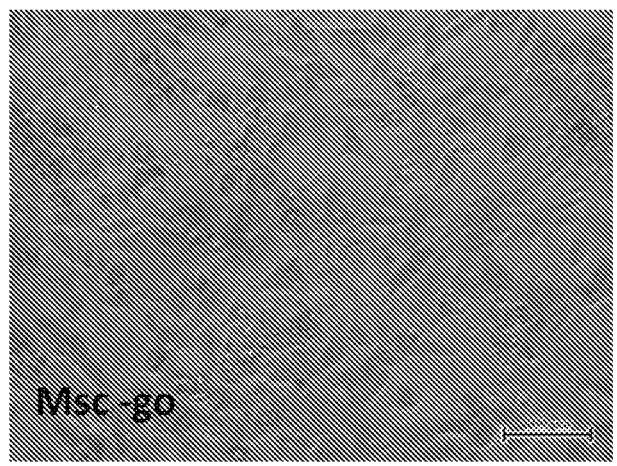
FIG. 9 shows Alizarin red staining of osteoblasts following 10 days in culture as a function of various medium treatments. The media was supplemented with additional 1 mM $Ca^{2+}$ from: A—ACC, B—$CaCl_2$), or C—control, no $Ca^{2+}$ addition.

Alizarin Red staining demonstrated a very strong signal in osteoblast cell samples that were supplemented with ACC compared to those supplemented with $CaCl_2$), which demonstrated a weak signal only, (FIG. 9). In addition to the signal, it can be seen in the figure that large plaques of calcium deposition are stained which are not observed in any of the controls treatments.

The Alizarin Red staining of cells grown in MSCgo rapid medium also demonstrated some staining of calcium deposition but the size of the deposition and its amount is significantly lower, and resembles the morphology and amount observed for cells supplemented within $CaCl_2$). Calcium deposition was not seen at cells grown in MSC NutriStem+ supplements (MSC sup; data not shown). MSC NutriStem+ sup medium is normally used to induce cells proliferation rather than differentiation. Indeed the number of cells observed is large but no calcium deposition is observed.

This observation suggests that ACC treatment enhances MBA13 cells differentiation into osteoblasts and raises the cells calcium deposition, i.e. enhances their functionality.

Another independent marker for osteoblast differentiation is the alkaline phosphatase. This enzyme is expressed maximally when the matrix maturation phase of cells occurs. Alkaline phosphatase staining was used as a complementary method to detect osteoblasts differentiation and functionality so as to verify the result obtained by the Alizarin staining.

Figure 10:
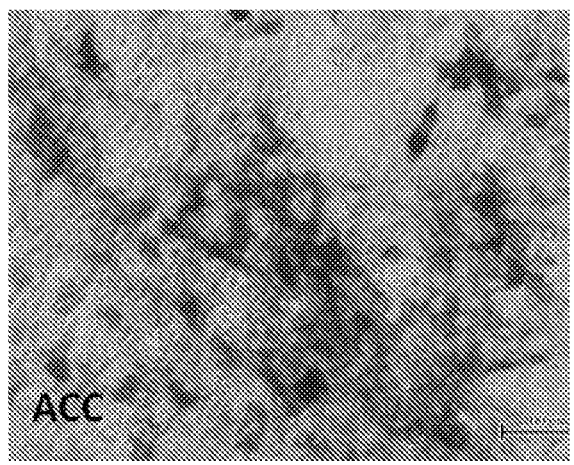
FIG. 10 shows Alkaline phosphatase staining of osteoblasts following 10 days in culture as a function of various medium treatments. The media c was supplemented with additional 1 mM $Ca^{2+}$ from: A—ACC, B—$CaCl_2$), or C—control, no $Ca^{2+}$ addition.
Figure 10:
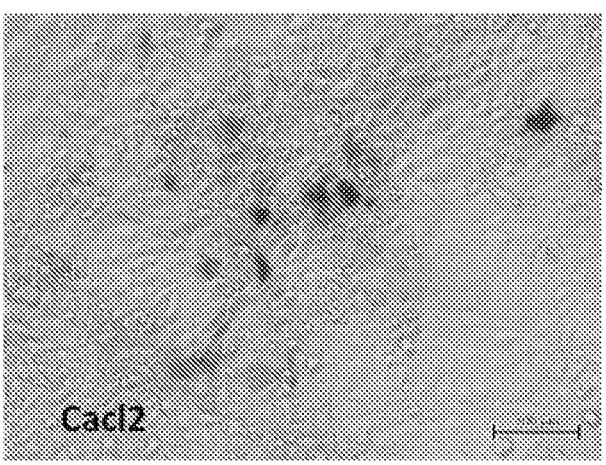
Figure 10:
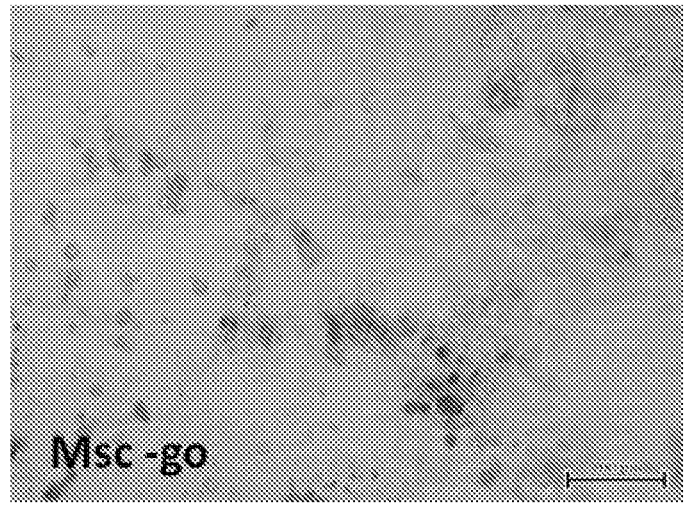

The alkaline phosphatase staining is shown in black color and the results are presented on FIG. 10. MBA13 cells that were treated with ACC demonstrated an intense signal in comparison to the other treatments. Indeed, Alkaline phosphatase staining support that osteoblasts differentiation is better in cultures treated with ACC.

Figure 11:
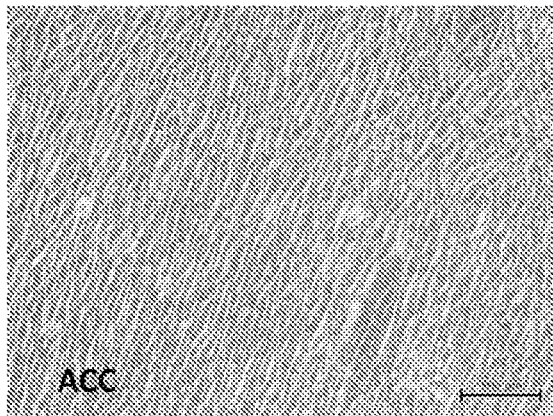
FIG. 11 shows Alizarin red staining (A-C) and Alkaline phosphatase (D-F) of mdx cell lines grown in media with different sources of additional 1 mM $Ca^{2+}$ added: A and D—ACC, B and E—$CaCl_2$, or C and F—control (without additional supplement with calcium).
Figure 11:
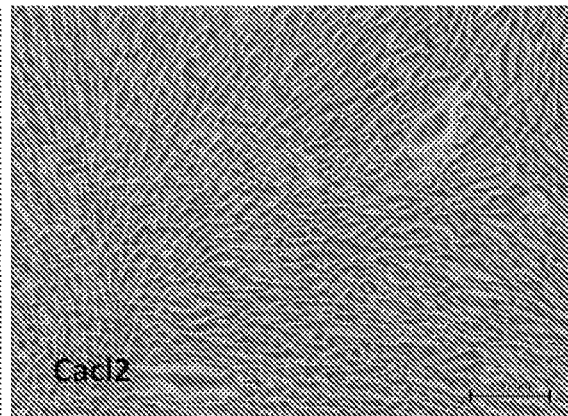
Figure 11:
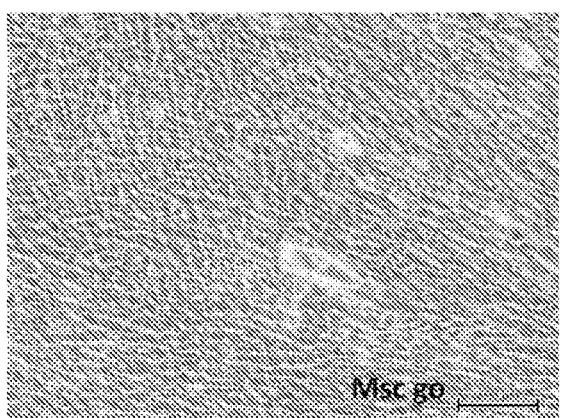
Figure 11:
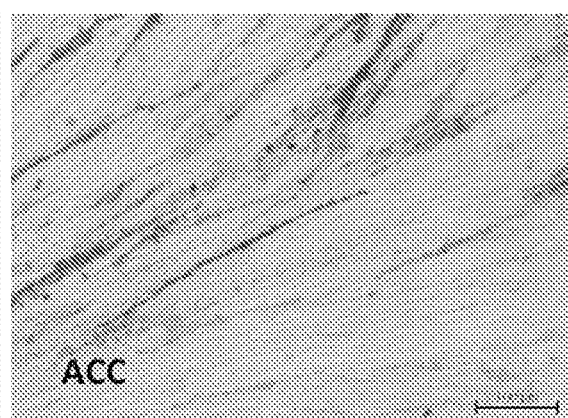
Figure 11:
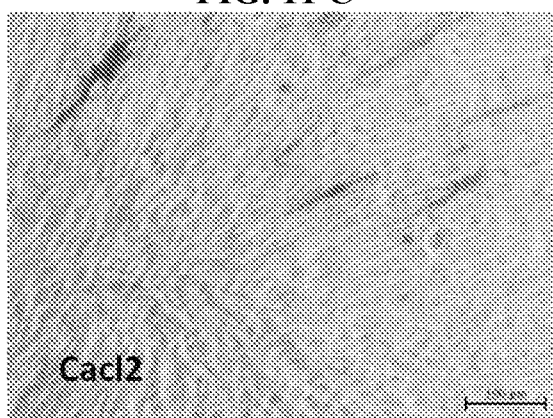
Figure 11:
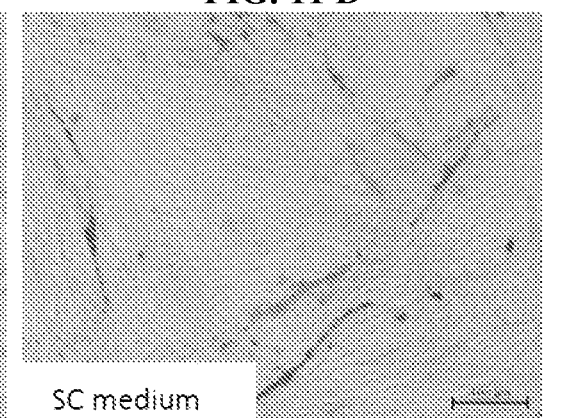

Alizarin staining of MDX cells treated with ACC enriched medium 10 days following seeding demonstrated no major differences in the staining among the treatments (see FIG. 11 A-C). These results support that Alizarin Red staining of osteoblasts is due to calcium deposition by the osteoblast and not due to ACC deposition caused by the treatment itself (i.e. it is not an experimental artifact).

The staining of Alkaline phosphatase of MDX cell lines (FIG. 11 D-E) demonstrated that there was no bone formation occurred. Interestingly, in Alkaline phosphatase stain enhanced myotubes formation was observed in ACC treated cells in comparison to cells grown in $CaCl_2$ supplemented medium or control.

Conclusions

Both independent staining, Alizarin Red and Alkaline phosphatase following the 10 days of seeding at different medium showed substantial stronger staining of the osteoblast cells deposition that were grown in medium supplemented with ACC in comparison to the controls used.

While large calcium deposition plaques were observed when cells grown in the presence of ACC, such deposition was not observed for cells grown in medium supplemented with $CaC_{12}$. Stronger signal might indicate on a larger functionality, since the staining demonstrated more plaque deposition. The result obtained by the MDX cells staining suggests that the plaques are not originated from the ACC addition but are a direct result of the osteoblast functionally.

Example 20—ACC for Enhancement Sperm Motility

Materials and Methods

ACC Suspension Preparation 36 ml of 3% Calcium chloride solution was mixed with 4 ml of 0.3% Citric Acid solution and with 10 ml of 0.5% Triphosphate solution. Then 40 ml of 2% Sodium carbonate solution was added to precipitate ACC. 10 ml of the stabilizing solution containing 0.5% triphosphate was added to the ACC suspension creating stabilized ACC suspension. The elemental calcium concentration of the obtained suspension was 75 mM.

Sperm Collection

Sperm were collected 3 times from the same ram (exp. 1) or twice from 3 rams (exp. 2 & 3) and evaluated to concentration and motility at room temperature. The sperm was diluted to concentration of 50 million sperm/ml in Synthetic Oviduct fluid (SOF) comprising: 107.70 mM NaCl, 7.16 mM KCl, 1.19 mM KH2PO4, 1.71 mM $CaCl_2$), 0.49 mM MgCl2, 25.07 mM NaHCO3, 3.30 mM Na lactate, and 1.50 mM glucose (10) in Milli-Q water. The osmolarity should be 270 mOsmol and the pH 7.55.

Sperm was then evaluated for motility using CASA (The riogenology, 2014, Volume 81, Issue 1, Pages 5-17) and cooled to 4° C. at 1° C./min.

Swim Up Procedure

Swim up procedure was performed at 38° C., the raw sperm (10 μl) was placed in eppendroph 1 ml vial and incubated for about 1 hour in SOF medium which was inserted in 0.25 ml straws (CBS, France). After 40-60 minutes the sperm which entered the straw were placed on a slide and evaluated by CASA.

Results

The motility of the freshly collected sperm was tested as described in materials and methods section with or without addition of amorphous calcium carbonate. The results are presented in Table 17.

TABLE 17

The motility assessment of sperm with and without the addition
of ACC suspension 34 μl/ml (2.6 mM of elemental Ca).

|  | % motility | % progressive motility |
|---|---|---|
| Control | 96 ± 1.15 | 55.3 ± 1.15 |
| ACC (34 μl/ml: 2.6 mM elemental Ca) | 95 ± 1 | 70.6 ± 3.2 |

It can be seen that sperm supplemented with ACC had much higher progressive motility than untreated sperm.

Example 21. Effect of ACC on Sperm Motility in a Swim Up Experiment

To evaluate the effect of ACC on sperm motility, a standard swim up experiment was performed in the presence of 17 μl/ml and 34 μl/ml of ACC suspension (1.3 and 2.6 mM of elemental Ca, respectively). The viable spermatozoa was counted after one hour and the results are summarized in Table 18.

TABLE 18

Effect of ACC on sperm motility in a swim up experiment
(concentration in million/ml)

| ACC concentration | Sperm concentration (×10⁶/ml) | | |
|---|---|---|---|
| (elemental calcium concentration) | exp 1 | exp 2 | exp 3 |
| control | 142 ± 7.3 | 97 ± 15 | 207 ± 12 |
| ACC 17 μl/ml (1.3 mM elemental Ca) | 523 ± 5.7 | 186 ± 14 | |
| ACC 34 μl/ml 1.3 mM elemental Ca) | | | 1463 ± 400 |

It can be clearly seen that addition of ACC significantly increased the number of viable spermatozoa in all experiments. In the samples supplemented with ACC, the number of viable spermatozoa was between 2 to 7 times higher than in the untreated samples.

Example 22. Effect of ACC Concentration on Sperm Motility in Swim-Up Experiment The effect of ACC concentration of the motility of sperm was tested by a swim-up experiment using 3 different samples for each ACC concentrations. The results are summarized in Table 19.

TABLE 19

Effect of ACC concentration on sperm motility in swim up experiment
(concentration in million/ml)

| ACC concentration (elemental calcium concentration) | Sperm concentration (×10⁶) |
|---|---|
| Control | 45.5 |
| ACC 8 μl/ml (0.6 mM elemental Ca) | 102, 77, 89 |
| ACC 17 μl/ml (1.3 mM elemental Ca) | 179, 170, 174 |
| ACC 34 μl/ml (2.6 mM elemental Ca) | 196, 200, 198 |
| ACC 60 μl/ml (4.6 mM elemental Ca)) | 182, 205, 193 |

It has been noted that the addition of 17 μl/ml ACC suspension to the synthetic oviduct fluid (SOF) solution and incubation at 38 C for 1 hour increased the concentration of motile sperm by at least 3 folds. Interestingly, higher concentration of ACC did not reduce the concentration of motile sperm after swim-up. It was concluded that ACC enhanced the concentration of sperm after swim-up procedure and did not have any bi-phasic effect for ionic calcium. Any ACC concentration above the minimum effective dose increases motility.

Example 23. ACC Preserves Ovaries In Vitro

Material and Methods

Ovaries were collected from mice (6 weeks old) cut to 0.4 mm×0.4 mm pieces. The ovaries were culture in 12 well plates. The culture medium was composed of: 90% Dulbecco's modified eagle medium-nutrient mixture F-12(DMEM-F12) calcium depleted (medium without calcium ions, special preparation), 10% fetal bovine serum (FBS), 2 mM glutamine, 25 μg/mL gentamicin and 0.3-0.5% NVR-Gel with or without stabilized 3.4 mM ACC-PP. After 48 h of culturing, 5IU of pregnant mare's serum gonadotrophin (PMSG) were added into the culture dish.

Results

Figure 12A:
FIG. 12 shows effect of stabilized ACC of in vitro cultured ovaries (A) in which granulosa cells surrounding the oocytes were intact versus control (B) (no ACC in the medium) in which non intact granulosa cells and oocyte at the Germinal Vesicles stage was observed.
Figure 12B:
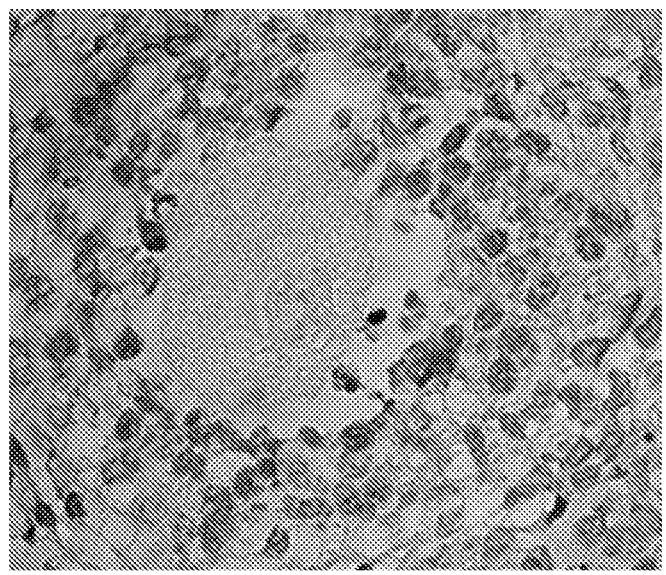

It can be seen on FIG. 12, that secondary follicles were developed after 2 weeks of in vitro culturing in the presence of stabilized ACC, and granulosa cells surrounding the oocytes were intact. On the contrary, secondary follicles in the control group show non-intact granulosa cells and Germinal vesicles oocyte. Much more follicles were observed in the ACC group, implying that addition of the ACC in the culture medium allows faster and better growth of follicles and improved preservation of ovaries.

Although the present invention has been described herein above by way of preferred embodiments thereof, it can be modified, without departing from the spirit and nature of the subject invention as defined in the appended claims.

The invention claimed is:

1. A cell culture medium, wherein the cell culture medium is supplemented with amorphous calcium carbonate (ACC) stabilized by at least one stabilizing agent selected from the group consisting of an inorganic polyphosphate comprising 2 to 10 phosphate groups and bisphosphonate, wherein said cell culture medium enhances the growth of a biological culture, and wherein a molar ratio between P atoms of the at least one stabilizer and Ca atoms of the ACC (P:Ca molar ratio) is at least 1:90.

2. The cell culture medium of claim 1, wherein said growth of a biological culture is selected from at least one of a proliferation of the biological culture, a maturation of the biological culture, a propagation of the biological culture, a regeneration of the biological culture, a cryopreservation of the biological culture, or a differentiation of the biological culture.

3. The cell culture medium of claim 1, wherein the biological culture is selected from a culture of eukaryote or a culture prokaryote cells.

4. The cell culture medium of claim 3, wherein the culture of eukaryote cells is selected from the group consisting of a culture of animal, plant, and insect cells.

5. The cell culture medium of claim 4, wherein at least one of:

the culture of animal cells is selected from the group consisting of a cell culture, a tissue culture, an organ culture, stem cells, gametes, embryos, an organ of human mammal, and an organ of a non-human mammal;

the cell culture is a primary cell culture or a cell line selected from a finite and continuous cell line; or the culture of plant cells is selected from the group consisting of a plant cell and tissue culture; and the culture of insect cells is selected from the group consisting of an insect cell, tissue and organ culture.

6. The cell culture medium of claim 5, wherein the mammal cell culture is selected from the group consisting of a nerve cell culture, a muscle cell culture, an epithelial cell culture, a bone cell culture, an adipose cell culture, a stem cell culture, and a blood cell culture.

7. The cell culture medium of claim 5, wherein at least one of:
the cell line is selected from the group consisting of FM3, HeLa, 293, A-549, ALC, CHO, HB54, HL60, COS-7, HEK293, VERO, BHK, CV1, MDCK, 3T3, C127 MRC-5, BAE-1, SH-SY5Y, L-929, HEP G2, NSO, U937, NAMALWA, WEHI 231, YAC 1, and U 266B1 cell line;
said mammal tissue culture is selected from the group consisting of an epithelial, a connective, a muscular, and a nervous tissue culture;
the stem cells are selected from the group consisting of embryonic, chorionic, amniotic, hematopoietic, mesenchymal, neural, NOM, glial, adult and induced pluripotent stem cells;
the embryos are human embryos or non-human mammal embryos selected from the group consisting of livestock animal, pet and rodent embryos;
said organ culture or said organ is an ovary, and/or said gametes cells are selected from oocytes or sperm cells; or
the culture of eukaryote cells is a culture of yeasts and said cell culture medium is selected from the group consisting of YPD, YPG, and YPAD.

8. The cell culture medium of claim 7, wherein:
the epithelial tissue culture is selected from the group consisting of skin, stomach and intestinal lining, kidney, and glands tissue culture;
the muscular tissue culture is selected from the group consisting of smooth, skeletal, and cardiac muscle tissue culture; and
the nervous tissue culture is selected from the group consisting of brain, spinal cord, and nerves tissue.

9. The cell culture medium of claim 4, wherein the medium is a natural medium selected from biological fluids, tissue extracts and clots; an artificial medium selected from a balanced salt solution, basal medium, complex medium, and/or serum free medium.

10. The cell culture medium of claim 9, wherein the cell medium is selected from the group consisting of DMEM/F-12, cleavage medium, DMEM, RPMI 1640, MEM, IMDM, L-15 Medium (Leibovitz), MCDB Medium, Medium 199, opti-MEM, Schneider's Drosophila medium, Grace's Insect medium, IPL-41 Insect Medium Sf-900, Serum-free Insect Media, Shields and Sang M3 Insect Medium, TC-100 Insect Medium, TNM-FH Insect Medium, Ham's F-12, Ham's F-10, GMEM, Ames' Medium, Basal Medium Eagle (BME), Claycomb, Click's Medium, Glasgow Minimum Essential Medium (GMEM), MegaCell Media, McCoy's 5A Modified Medium, NCTC Medium, Williams' Medium E, Waymouth Medium, TC-10 IPL-10 medium, medium for sperm separation, wash or maturation, medium for fertilization, for embryo development, and medium for embryo and/or gamete cryopreservation.

11. The cell culture medium of claim 1, wherein an average diameter of the stabilized ACC primary particles is about 10 nm to about 500 nm.

12. The cell culture medium of claim 1, wherein the at least one stabilizing agent is selected from the group consisting of triphosphate, etidronic acid, pyrophosphate, hexamethaphosphate, and any combination thereof.

13. The cell culture medium of claim 1, wherein the cell culture medium enhances the growth of (i) muscle, nerve or bone cell or tissue culture, (ii) human or non-human mammal embryos, (iii) stem cells, (iv) gametes; or (v) ovaries.

14. The cell culture medium of claim 13, wherein the cell culture medium enhances (i) nerve cells regeneration, (ii) muscle cells formation, (iii) stem cells differentiation, (iv) oocytes or sperm cells maturation, (v) embryos development, or (vi) embryo or gamete cryopreservation.

15. The cell culture medium of claim 1, wherein a final concentration of the stabilized ACC in the cell culture medium is about 1 to about 10 mM.

16. A kit comprising:
(i) amorphous calcium carbonate (ACC) formulated as a supplement for cell culture medium, wherein said ACC is stabilized by at least one stabilizing agent;
(ii) a cell culture medium supplement including amorphous calcium carbonate (ACC) stabilized by at least one stabilizing agent; or
(iii) calcium chloride, sodium carbonate, at least one stabilizer, and instruction for preparing a stabilized ACC from said calcium chloride, sodium carbonate, and at least one stabilizer; and
instructions for use of said stabilized ACC or said supplement in combination with a cell culture medium,
wherein the at least one stabilizing agent is selected from the group consisting of an inorganic polyphosphate comprising 2 to 10 phosphate groups and bisphosphonate, wherein a molar ratio between P atoms of the at least one stabilizer and Ca atoms of the ACC (P:Ca molar ratio) is at least 1:90.

17. The kit of claim 16, further comprising a cell culture medium.

18. A cell culture medium, wherein the cell culture medium is supplemented with amorphous calcium carbonate (ACC) stabilized by at least one stabilizing agent selected from the group consisting of an inorganic polyphosphate comprising 2 to 10 phosphate groups, bisphosphonate, and any combinations thereof, wherein a molar ratio between P atoms of the at least one stabilizer and Ca atoms of the ACC (P:Ca molar ratio) is at least 1:90, and wherein said cell culture medium enhances the growth of a biological culture, wherein the biological culture is a mammal cell culture selected from the group consisting of a stem cell culture, oocytes and sperm cells, embryos, a nerve cell culture, a muscle cell culture, an epithelial cell culture, a bone cell culture, an adipose cell culture, and a blood cell culture.

19. The cell culture medium of claim 18, wherein a final concentration of stabilized ACC in the cell culture medium is about 0.1 to about 20 mM.

* * * * *